United States Patent
Norchi et al.

(10) Patent No.: US 9,339,476 B2
(45) Date of Patent: May 17, 2016

(54) IMPLANTABLE MESHES FOR CONTROLLING THE MOVEMENT OF FLUIDS

(71) Applicant: Arch Biosurgery, Inc., Cambridge, MA (US)

(72) Inventors: Terrence Norchi, Natick, MA (US); Steven Kates, Needham, MA (US); Rutledge Ellis-Behnke, Myrtle Beach, SC (US)

(73) Assignee: Arch Biosurgery, Inc., Cambridge, MA (US)

(*) Notice: Subject to any disclaimer, the term of this patent is extended or adjusted under 35 U.S.C. 154(b) by 0 days.

(21) Appl. No.: 14/466,699

(22) Filed: Aug. 22, 2014

(65) Prior Publication Data

US 2015/0056263 A1 Feb. 26, 2015

Related U.S. Application Data

(60) Provisional application No. 61/868,674, filed on Aug. 22, 2013.

(51) Int. Cl.
| | |
|---|---|
| *A61K 9/70* | (2006.01) |
| *A61L 15/32* | (2006.01) |
| *A61L 27/22* | (2006.01) |
| *A61L 27/50* | (2006.01) |
| *A61L 27/58* | (2006.01) |
| *A61L 31/14* | (2006.01) |
| *A61L 31/04* | (2006.01) |
| *A61L 26/00* | (2006.01) |
| *A61K 38/02* | (2006.01) |

(52) U.S. Cl.
CPC .................. *A61K 9/7007* (2013.01); *A61K 9/70* (2013.01); *A61K 38/02* (2013.01); *A61L 15/32* (2013.01); *A61L 26/0028* (2013.01); *A61L 26/0047* (2013.01); *A61L 27/22* (2013.01); *A61L 27/227* (2013.01); *A61L 31/043* (2013.01); *A61L 31/047* (2013.01); *A61L 31/14* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson | |
| 4,272,398 A | 6/1981 | Jaffe | |
| 4,636,208 A | 1/1987 | Rath | |
| 4,861,627 A | 8/1989 | Mathiowitz | |
| 5,180,375 A | 1/1993 | Feibus | |
| 5,192,302 A | 3/1993 | Kensey | |
| 5,222,974 A | 6/1993 | Kensey | |
| 5,645,565 A | 7/1997 | Rudd | |
| 5,670,483 A | 9/1997 | Zhang | |
| 5,762,846 A | 6/1998 | Blankenbeckler | |
| 5,955,343 A | 9/1999 | Holmes | |
| 6,333,194 B1 | 12/2001 | Levy | |
| 6,368,877 B1 | 4/2002 | Zhang | |
| 6,548,630 B1 | 4/2003 | Zhang | |
| 6,663,655 B2 | 12/2003 | Ginn | |
| 6,711,879 B2 | 3/2004 | Korteweg | |
| 6,800,116 B2 | 10/2004 | Stevens | |
| 6,800,481 B1 | 10/2004 | Holmes | |
| 6,844,324 B1 | 1/2005 | Zhang | |
| 6,953,656 B2 | 10/2005 | Jacobson | |
| 6,953,659 B2 | 10/2005 | Jacobson | |
| 7,098,028 B2 | 8/2006 | Holmes | |
| 7,179,784 B2 | 2/2007 | Zhang | |
| 7,390,526 B2 * | 6/2008 | Stupp | A61L 27/32 427/2.26 |
| 7,449,180 B2 | 11/2008 | Kisiday | |
| 7,700,721 B2 | 4/2010 | Boden | |
| 7,704,740 B2 | 4/2010 | Schindler | |
| 8,039,258 B2 | 10/2011 | Harris | |
| 8,512,728 B2 | 8/2013 | Ladet | |
| 8,568,637 B2 | 10/2013 | Gazit | |
| 2002/0072074 A1 | 6/2002 | Zhang | |
| 2002/0160471 A1 | 10/2002 | Kisiday | |
| 2003/0176335 A1 | 9/2003 | Zhang | |
| 2004/0011201 A1 | 1/2004 | Stevens | |
| 2004/0023414 A1 | 2/2004 | Zhang | |
| 2004/0087013 A1 | 5/2004 | Holmes | |

(Continued)

FOREIGN PATENT DOCUMENTS

| | | |
|---|---|---|
| WO | 9509659 | 4/1995 |
| WO | 98158967 | 12/1998 |

(Continued)

OTHER PUBLICATIONS

Ellis-Behnke et al. Nano hemostat solution: immediate hemostasis at the nanoscale. Nanomedicine: Nanotechnology, Biology, and Medicine. 2006, vol. 2, pp. 207-215.*

Ahmad, et al., "A novel hybrid system for the fabrication of a fibrous mesh with micro-inclusions", Carbohydr Polym.,89(1):222-9 (2012).

Brun, et al., "Electrospun scaffolds of self-assembling peptides with poly (ethylene oxide) for bone tissue engineering", Acta Biomater., 7:2526-32 (2011).

Caplan, et al., "Control of self-assembling oligopeptide matrix formation through systematic variation of amino acid sequence", Biomaterials, 23(1):219-27 (2002).

(Continued)

*Primary Examiner* — Jeffrey E Russel
(74) *Attorney, Agent, or Firm* — Pabst Patent Group LLP

(57) ABSTRACT

Meshes for use to control the movement of bodily fluids, such as blood, are described herein. The mesh can be partially or completely biodegradable or non-biodegradable. In one embodiment, the mesh is formed from one or more self-assembling peptides. The peptides can be in the form of fibers, such as nanofibers. The peptides can be assembled prior to formation of the mesh or after the mesh has been formed but before it is applied. Alternatively, the mesh can be prepared from unassembled peptides, which assemble at the time of application. The peptides can assemble upon contact with bodily fluids (e.g., blood) or can be contacted with an ionic solution to initiate assembly.

18 Claims, No Drawings

(56) References Cited

U.S. PATENT DOCUMENTS

| | | |
|---|---|---|
| 2004/0204561 A1 | 10/2004 | Ellison |
| 2004/0242469 A1 | 12/2004 | Lee |
| 2005/0287186 A1 | 12/2005 | Ellis-Behnke et al. |
| 2006/0019309 A1 | 1/2006 | Zhang |
| 2006/0025524 A1 | 2/2006 | Schneider |
| 2006/0084607 A1 | 4/2006 | Spirio |
| 2006/0088510 A1 | 4/2006 | Lee |
| 2006/0148703 A1 | 7/2006 | Lee |
| 2006/0199778 A1 | 9/2006 | Ellis-Behnke et al. |
| 2006/0211615 A1 | 9/2006 | Zhang |
| 2007/0099840 A1* | 5/2007 | Ulijn et al. .............. 514/17 |
| 2007/0203062 A1* | 8/2007 | Ellis-Behnke et al. ........ 514/12 |
| 2007/0287741 A1 | 12/2007 | Herzberg |
| 2008/0032934 A1 | 2/2008 | Ellis-Behnke et al. |
| 2008/0091233 A1 | 4/2008 | Ellis-Behnke et al. |
| 2008/0274979 A1* | 11/2008 | Ellis-Behnke et al. ........ 514/14 |
| 2009/0111734 A1 | 4/2009 | Ellis-Behnke et al. |
| 2011/0002880 A1* | 1/2011 | Takamura et al. ........... 424/85.2 |
| 2011/0201541 A1* | 8/2011 | Takamura et al. ............ 514/1.1 |
| 2012/0085262 A1 | 4/2012 | Klimov |
| 2013/0095060 A1* | 4/2013 | Hsieh et al. ................. 424/85.1 |
| 2014/0093473 A1* | 4/2014 | Hauser et al. .............. 424/78.17 |
| 2015/0218252 A1* | 8/2015 | Ingber .................... C07K 14/78 514/773 |

FOREIGN PATENT DOCUMENTS

| | | |
|---|---|---|
| WO | 99052574 | 10/1999 |
| WO | 02062969 | 8/2002 |
| WO | 03006043 | 1/2003 |
| WO | 03084980 | 10/2003 |
| WO | 03096972 | 11/2003 |
| WO | 2004007532 | 1/2004 |
| WO | 2005014615 | 2/2005 |
| WO | 2005123760 | 12/2005 |
| WO | WO 2006014570 A2 * | 2/2006 |
| WO | 2006036826 | 4/2006 |
| WO | WO 2006116524 A1 * | 11/2006 |
| WO | 2007142757 | 12/2007 |
| WO | 2008113030 | 9/2008 |
| WO | 2008134544 | 11/2008 |

OTHER PUBLICATIONS

Caplan, et al., "Self-assembly of a beta-sheet protein governed by relief of electrostatic repulsion relative to van der Waals attraction", Biomacromolecules, 1:627-31 (2000).

Frechet, "Dendrimers and supramolecular chemistry", PNAS, 99(8):4782-7 (2002).

Holmes, et al., "Extensive neurite outgrowth and active synapse formation on self-assembling peptide scaffolds", PNAS, 97(12):6728-33 (2000).

Khadka and Hayne, "Protein- and peptide-based electrospun nanofibers in medical biomaterials", Nanomedicine, 8:1242-62 (2012).

Leon, et al., "Mechanical properties of a self-assembling oligopeptide matrix", J. Biomater. Sci Polym Ed., 9:297-312 (1998).

Ma, et al., "Supramolecular polymer chemistry: self-assembling dendrimers using the DDA.AAD (GC-like) hydrogen bonding motif", J. Am. Chem. Soc., 124(46):13757-69 (2002).

Nguyen and Lee, "The effect of cross-linking on the microstructure, mechanical properties and biocompatibility of electrospun polycaprolactone-gelatin/PLGA-gelatin/PLGA-chitosan hybrid composite", Sci. Technol. Adv. Mater., 13:035002 (2012).

Zhang, et al., "Self-complementary oligopeptide matrices support mammalian cell attachment", Biomaterials, 16:1385-93 (1995).

Zhang, et al., "Spontaneous assembly of a self-complementary oligopeptide to form a stable macroscopic membrane", PNAS, 90:3334-8 (1993).

Zimmerman, et al., "Self-assembling dendrimers", Science, 271(5252):1095-8 (1996).

Adler, "Self-assembling gel stops bleeding in seconds", New Scientist Tech,1(3):117 (Oct. 10, 2006).

AlertNet, "Researches study liquid as tool to stop bleeding", www.alertnet.org, pp. 1, (Oct. 10, 2006).

Ball, "Brain Knitting", materials@nature.com, pp. 1-2 (2006).

Bansal, "Scientists develop liquid that could revolutionize bleeding control", All Headline News, pp. 1 (2006).

Barone, "Nanoliquid stops bleeding practically in a nanosecond", Discover Magazine, pp. 1 (Feb. 25, 2007), accessed Dec. 22, 2007.

BBC News, "Liquid to seal open wounds fast", www.newsvote.bbc.co.uk, pp. 1-3, (Oct. 14, 2006), accessed 07-101-2009.

Benita, "Characterization of drug-loaded poly(d,l-lactide) microspheres", J. Pharm. Sci., 73(12):1721-4 (1984).

Bokhari, "The enhancement of osteoblast growth and differentiation in vitro on a peptide hydrogel-polyHIPE polymerhybrid material", Biomaterials, 26(251:5198-208 (2005).

Bullis, "Nanohealing", Technology Review, pp. 1.3 (Mar./Apr. 2007).

Chen, et al., "A hybrid silk/RADA-Based fibrous scaffold with triple hierarch for ligament regeneration", Tissue Eng, 18(13-14):1399-409 (2012).

Christie, "The nano-knitters", Popular Science, pp. 1, accessed Aug. 11, 2006.

Conform, definition from http://www.merriam-webster.com/dictionary/conform, pp. 1-2. accessed Aug. 4, 2009.

Crowston, "New Optic Nerve? International Glaucoma Review", The Journal for the Glaucoma Society, (Meeting) Reports, pp. 1.2, (IGR 9.1 Jun. 2007).

Dahlberg, "Surgical discovery promising", The Sacramento Bee, pp. 1-3 (Oct. 10, 2006), accessed (Oct. 10, 2006).

Daily India, "Study: Biodegradable liquids halt bleeding", www.dailyindia.com; pp. 1, accessed. (Oct. 10, 2006).

Deutschlandfunk, "Liquid plaster", www.dradio.de; pp. 1.2, (Oct. 11, 2006), accessed (Oct. 12, 2006).

EJ, "Closing the cns gap", ACS Chemical Biology, 1(3):117, (2006).

Ellis-Behnke, "Crystal clear surgery with self-assembling molecules that act as a bio barrier in the brain and intetstine", Nanomedicine: Nanotechnology Biology and Medicine 1(3):269-270 (2005).

Ellis-Behnke, "Molecular repair of the brain using self-assembling peptides", Chien. Oggi, 24(4) 42-45 (2006).

Ellis-Behnke, "Molecular Restoration of the Body: Nano neuro knitting for brain repair", JEAAM & BAAMJ, 4:35-37(2006).

Ellis-Behnke, "Nano neuro knitting: peptide nanofiber scaffold for brain repair and axon regeneration with functional return of vision", Proc. Natl. Acad. Sci. U.S.A. Mar. 28, 2006 103(13):5054-9 (2006). Epub Mar. 20, 2006. Erratum in: Proc. Natl. Acad. Sci. U.S.A. May 9, 2006;103(19):7530.

Ellis-Behnke, "Using nanotechnology to design potential therapies for CNS regeneration", Curr. Pharm. Des.,13(24):2519#2D(2007).

Endometriosis, Merck Manual Professional, pp. 1-5, www.merck.com accessed Aug. 4, 2009.

Fox News, "New peptide salve could replace adhesive bandages", www.foxnews.com, pp. 1, (Oct. 10, 2006), accessed Oct. 10, 2006.

Genove, "The effect of functionalized self-assembling peptide scaffolds on human aortic endothelial cell function", Biomaterials, 26(16):3341-51 (2005).

Gibian, "Study: Biodegradable liquids halt bleeding", United Press International,Oct. 10, 2006.

Gill, "Pour-on nanotechnology stops bleeding in seconds", Chemistry World, pp. 1-2, (2006).

Guo, "Reknitting the injured spinal cord by self-assembling peptide nanofiber scaffold", Nanomedicine, 3(4):311-21 (2007).

Hampton, "Healing power found in nano knitting", JAMA, 3:297(1):31 (2007).

Hartgerink, "Nanomedicine: New material stops bleeding in a hurry", Nature Nanomedicine, 1(3): 166-167 (2006).

Hill, "A field guide to foldamers", Chem. Rev., 101(12):3893-4012 (2001).

Intestinal Obstruction, Merck Manual Professional, pp. 1-4. www.merck.com accessed Aug. 4, 2009.

Iran Daily, "Brain-healing bridges", www.iran-daily.com, pp. 1-2, accessed Apr. 25, 2006.

Keloid and Hypertrophic Scar: Treatment & Medication, from, http://emedicine.medscape.comlarticle11057599-treatment, pp. 1-16, accessed Aug. 4, 2009.

(56) References Cited

OTHER PUBLICATIONS

Keloids, Merc Manual Professional, pp. 1, www.merck.com access Aug. 4, 2009.

Kendhale, "Isotactic N-alkyl acrylamide oligomers assume self-assembled sheet structure: first unequivocal evidence from crystal structure", Chem Comm. (Comb), 26:2756-2758 (2006).

Knudsen, "Nanosolution halts bleeding", Technology Review, accessed Oct. 10, 2006.

Marks, "Optic nerve regrown", New Scientist on www.stemcellschina.com, (Mar. 15, 2006), updated Jun. 26, 2006, accessed Aug. 11, 2006.

Mathiowitz, "Morphology of polyanhydride microsphere delivery systems", Scanning Microscopy, 4(2):329-340 (1990).

Mathiowitz, "Novel microcapsules for delivery systems", Reactive Polymers, 6:275-83 (1987).

Mathiowitz, "Polyanhydride microspheres. IV: Morphology and characterization of systems made by spray drying", J. Appl. Polymer Sci, 45:125-134 (1992).

Mathiowitz, "Polyanhydride microspheres as drug carriers. II. microencapsulation by solvent removal", J. Appl. Polymer Sci., 35, 755-774 (1988).

Mathiowitz and Langer, "Polyanhydride microspheres as drug carriers I. Hot-melt microencapsulation", J. Controlled Release,5(1):13-22 (1987).

Mishra, et al., "Ultrasmall natural peptides self-assemble to strong temperature-resistant helical fibers in scaffolds suitable for tissue engineering", Nano Today, 6(3):232-9 (2011).

MIT News, "MIT material stops bleeding in seconds", www.web.mit.edu, pp. 1.2, Oct. 10, 2006, accessed Jul. 10, 2009.

Mumbai Mirror, "New solution to stop bleeding", www.mumbaimirror.com; pp. 1 accessed Oct. 17, 2006.

Nano China, "Stopping bleeding", www.nanochina.cn, pp. 1-3, (Oct. 27, 2006), accessed Nov. 11, 2006.

Narmoneva, "Self-assembling short oligopeptides and the promotion of angiogenesis", Biomaterials, 26(23):4837-46(2005).

Newindpress, "New nano-gel that stops bleeding within seconds", www.newindpress.com, pp. 1, accessed Oct. 11, 2006.

News in Science, "Liquid stops bleeding during surgery", Reuters, pp. 1-2, accessed Oct. 10, 2006.

Palmer, "Peptide soup halts blood loss", Science NOW Daily News, pp. 1, Oct. 10, 2006.

Penland, "Recently discovered by researchers, a new liquid can stop bleeding faster than you can slap on a band-aid", Discover Magazine, Oct. 19, 2006.

Residue, definition from http://dictionary.reference.comlbrowselresidue, pp. 1-4. accessed Jul. 13, 2009.

Sawhney, "Bioerodible hydrogels based on photopolymerized poly-ethylene glycol)-co-poly(ahydroxy acid) diacrylatemacromers", Macromolecules, 26(4):581-587 (1993).

Schneider, "Behavioral testing and preliminary analysis of the hamster visual system", Nat. Protoc., 1(4):1898-905(2006).

Science, Engineering and Technology, "Nanomaterial stops bleeding in seconds", www.scenta.co.uk, pp. 1-2, accessed Oct. 10, 2006.

Scientific American, "Protein gel stops bleeding in unknown way", www.sciam.com, pp. 1-2, accessed Oct. 10, 2006.

Teather, "Differential induction of c-Jun and Fos-like proteins in rat hippocampus and dorsal striatum after training in two water maze tasks", Neurobiol Learn Mem., 84(2):75-84 (2005).

Thomas, "Nano neuro knitting repairs injured brain", Lancet Neurol., 5(5):386 (2006).

Trafton, "New material halts bleeding", MIT Tech Talk, 51(5): 1-3 (2006).

Tu and Tirrell, "Bottom-up design of biomimetic assemblies", Adv. Drug Deliv. Rev., 56(11):1537-63 (2004).

Tubal Dysfunction and Pelvic Lesions, Merck Manual Professional, pp. 1.2, www.merck.com accessed Aug. 4, 2009.

What's Next in Science & Technology, "Biodegradable liquids can stop bleeding almost instantly could significantly impactmedicine", (Oct. 10, 2006), accessed Oct. 15, 2006.

Wilson, "Nano neuro-kit", Drug Discovery & Development, accessed Sep. 22, 2006.

Yung, "Scientists discover new way to control bleeding", The Standard, pp. 1.2, (Oct. 11, 2006), accessed Oct. 10, 2006.

Zhang, "Designer self-assembling peptide nanofiber scaffolds for#s=s#tissue cell cultures", Semin. Cancer Biol., 15(5):413-20 (2005).

Davis, et al., "Injectable self-assembling peptide nanofibers create intramyocardial microenvironments for endothelial cells", Circulation, 111(4):442-50 (2005).

Moore, et al., "A field guide to foldamers", Chem. Rev., 101(12), 3893-4012 (2001).

Scrivener, "Bleeding? Here\s a simple solution", Toronto Star, (Oct. 15, 2006).

Zhang, et al., "Peptide self-assembly in functional polymer science and engineering", Reactive & Functional Polymers, 41, 91-102 (1999).

\* cited by examiner

IMPLANTABLE MESHES FOR CONTROLLING THE MOVEMENT OF FLUIDS

CROSS-REFERENCE TO RELATED APPLICATIONS

This application claims priority to U.S. Ser. No. 61/868,674, filed on Aug. 22, 2013, which is incorporated herein in its entirety.

REFERENCE TO SEQUENCE LISTING

The Sequence Listing submitted Aug. 22, 2014 as a text file named "CNS_106_ST25.txt," created on Aug. 19, 2014, and having a size of 100,000 bytes is hereby incorporated by reference pursuant to 37 C.F.R. §1.52(e)(5).

FIELD OF THE INVENTION

This invention is in the field of surgical meshes, particularly meshes which control (e.g., prevent) the movement of bodily fluids, composed of self-assembling peptides.

BACKGROUND OF THE INVENTION

The undesirable movement of bodily fluids such as blood as a result of injury, disease or during surgery is often a major concern. Substantial loss of blood can cause multiple problems for the patient and the presence of blood or other bodily fluids in undesirable locations can be detrimental to normal tissue or interfere with the surgeon's ability to view the operative field. Often surgery is delayed while blood is removed and the bleeding is brought under control. Bleeding can be problematic even during minimally invasive surgery (e.g., laparoscopic surgery). In some instances, surgeons must convert these preferred procedures into traditional open surgeries if bleeding cannot be adequately controlled.

Options for minimizing or controlling the movement of bodily fluids in any of these settings are limited and typically include the application of pressure, either directly to a vessel or to the body external to the vessel. Pressure must be maintained until the bleeding is under control. Other physical methods include the use of clamps, clips, plugs, sponges, or sutures. These devices have limited efficacy, and they can be cumbersome to apply, particularly if there are many small bleeding vessels. Use of heat to coagulate blood and cauterize bleeding vessels is widely used during surgery, but it is a destructive process that can result in damage to tissue.

Surgical meshes made from nanostructures have been developed as a means to provide mechanical support during surgical procedures. Meshes formed of woven and non-woven scaffolds including a variety of natural and non-natural polymers are described in U.S. Pat. Nos. 8,568,637; 7,700,721; 8,039,258; 7,704,740; 5,762,846; 8,512,728; as well as Dhan, et al., *Nanomedicine: Nanotechnology, Biology, and Medicine*, 8, pp. 1242-1262 (2012); Nguyen and Lee, *Sci. Technol. Adv. Mater.*, 13, 035002 (11 pp) (2012); Ahmad, et al., *Carbohydrate Polymers*, V89 (1), pp. 222-229 (2012); and Brun, et al., *Acta Biomaterialia*, 7, pp. 2526-2532 (2011).

However, there remains a need for surgical meshes that can be used for mechanical support and at same time provide a barrier to the movement of bodily fluids.

It is therefore an object of the present invention to provide compositions for preventing the movement of bodily fluids.

It is another object of the present invention to provide methods and compositions for providing tissue-type specific hemostatic meshes.

It is still a further object of the present invention to provide methods and compositions for tissue integration and attachment.

SUMMARY OF THE INVENTION

It has been established that surgical meshes including one or more self-assembling peptides can prevent the movement of bodily fluids and provide mechanical support for surgical procedures.

Meshes for use to control the movement of bodily fluids, such as blood, are described herein. In one embodiment, the mesh is formed from one or more self-assembling peptides. The peptides can be in the form of fibers, such as nanofibers. The peptides can be assembled prior to formation of the mesh or after the mesh has been formed but before it is applied. Alternatively, the mesh can be prepared from unassembled peptides, which assemble at the time of application. The peptides can assemble upon contact with bodily fluids (e.g., blood) or can be contacted with an ionic solution to initiate assembly.

In some embodiments the self-assembling peptides have a sequence of amino acid residues conforming to one or more of the following formulas:

$$((Xaa^{neu}\text{-}Xaa^{+})_x(Xaa^{neu}\text{-}Xaa^{-})_y)_n;$$

$$((Xaa^{neu}\text{-}Xaa^{-})_x(Xaa^{neu}\text{-}Xaa^{+})_y)_n;$$

$$((Xaa^{+}\text{-}Xaa^{neu})_x(Xaa^{-}\text{-}Xaa^{neu})_y)_n;\text{ and}$$

$$((Xaa^{-}\text{-}Xaa^{neu})_x(Xaa^{+}\text{-}Xaa^{neu})_y)_n,$$

where $Xaa^{neu}$ represents an amino acid residue having a neutral charge, $Xaa^{+}$ represents an amino acid residue having a positive charge, $Xaa^{-}$ represents an amino acid residue having a negative charge, x and y are integers having a value of 1, 2, 3, or 4, independently, and n is an integer having a value of 1-5.

In certain embodiments all of the self-assembling peptides in the mesh are of the same size and have the same amino acid sequence. In other embodiments, meshes can include two or more different self-assembling peptides, having different sizes and sequences. The meshes can also include other polymers and can be partly biodegradable, fully biodegradable, or non-biodegradable. Meshes can include a scaffold or support material. In one embodiment the support material is an adhesive bandage.

Meshes including one or more self-assembling peptides and one or more additional active or biological agents, such as live cells, therapeutic agents, prophylactic agents, and/or diagnostic agents are also provided. The additional active agents can be antimicrobial agents, hemostatic agents, desiccants, pH-adjusting agents, growth factors, cytokines, or combinations thereof.

Methods of making meshes that contain self-assembling peptides are also provided. The methods can include injection molding, stamping, templating onto a surface having a desired shape, electrospinning, freezing of a powder, freezing of a solution, coating of a solid substrate, or a combination thereof. The self-assembling peptides can be assembled by contacting the mesh with a solution of cations. Self-assembly of the peptides can occur at the time of manufacture of the mesh, or immediately prior to, during or after application of the mesh.

Methods for preventing the movement of bodily fluids in a subject including applying or implanting in a patient one or more surgical meshes including self-assembling peptides are also provided. In certain embodiments the methods prevent the movement of blood. The patient can suffer from a primary, secondary, or acquired bleeding/coagulation/clotting disorder.

Systems for the delivery and/or application of meshes including one or more self-assembling peptides are also provided. In some embodiments the delivery system includes the use of a cone.

DETAILED DESCRIPTION OF THE INVENTION

I. Definitions

"Biocompatible", as used herein, refers to compatibility with living tissue or a living system by not being toxic, injurious, or physiologically reactive and not causing immunological rejection.

"Complementary" means having the capability of forming ionic or hydrogen bonding interactions between hydrophilic residues from adjacent peptides in a structure. Each hydrophilic residue in a peptide either hydrogen bonds or ionically pairs with a hydrophilic residue on an adjacent peptide, or is exposed to solvent. Pairing may also involve van der Waals forces.

"Effective amount", in reference to an active agent such as a self-assembling peptide or biomolecule, pharmaceutical agent, etc. refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for treatment of a disease or disorder may be an amount sufficient to promote recovery to a greater extent than would occur in the absence of the composition.

"Hemostasis" refers to the cessation of bleeding.

"Preventing" refers to causing a condition, state, or disease, or symptom or manifestation of such, or worsening of the severity of such, not to occur. Preventing includes reducing the risk that a condition, state, or disease, or symptom or manifestation of such, or worsening of the severity of such, will occur.

The terms "treat", "treatment" and "treating" refer to the reduction or amelioration of the progression, severity and/or duration of an injury, disease or disorder, delay of the onset of a disease or disorder, or the amelioration of one or more consequences, indications or symptoms (preferably, one or more discernible symptoms) of an injury, disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder.

"Repair", as used in reference to the repair of tissue in various embodiments of the invention, may include any aspect of anatomical or functional restoration of the condition of the tissue prior to an injury, deterioration, or other damage. For example, it may include restoration of physical continuity between portions of tissue that were separated by injury, deterioration, or other damage. Preferably such restoration of physical continuity includes reposition or reconnection of the portions of tissue without appreciable separation by tissue of a type that was not present prior to the injury, such as scar tissue. Repair may, but need not, include growth or development of new tissue. "Repair" and "Healing" are used interchangeably herein.

"Self-assembling", as used herein, refers to the assembly of molecules into defined, stable, noncovalently bonded assemblies that are held together by intermolecular and/or intramolecular forces. The assembly may be spontaneous or induced.

II. Meshes

Meshes for use to control the movement of bodily fluids, such as blood, are described herein. The mesh can be partially or completely biodegradable or non-biodegradable. In one embodiment, the mesh is formed from one or more self-assembling peptides. The peptides can be in the form of fibers, such as nanofibers. The peptides can be assembled prior to formation of the mesh or after the mesh has been formed but before it is applied. Alternatively, the mesh can be prepared from unassembled peptides, which assemble at the time of application. The peptides can assemble upon contact with bodily fluids (e.g., blood) or can be contacted with an ionic solution to initiate assembly.

In another embodiment, the mesh is formed from a mixture of self-assembling peptides and another material. The other material can be an organic or inorganic material. Exemplary organic materials include polypeptides and proteins. In some embodiments, fibrous peptides such as collagen and amyloids.

In other embodiments, the peptides, in the form of a dry powder or gel, are incorporated into an adhesive or non-adhesive backing, wherein the backing is formed of a material other than the self-assembling peptide.

A. Self-assembling Peptides

In one embodiment, the self-assembling material is a self-assembling peptide. The term "peptide," as used herein includes "polypeptide," "oligopeptide," and "protein," and refers to a chain of at least two α-amino acid residues linked together by covalent bonds (e.g., peptide bonds). "Peptide" may refer to an individual peptide or to a collection of peptides having the same or different sequences, any of which may contain naturally occurring α-amino acid residues, non-naturally occurring α-amino acid residues, and combinations thereof. α-Amino acid analogs are also known in the art and may alternatively be employed. In particular, D-α-amino acid residues may be used.

Peptides can be represented as amino acid residue sequences. Those sequences are written left to right in the direction from the amino ("n-") to the carboxyl ("-c") terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). A "Variant" of a peptide refers to a polypeptide or differs from a reference polypeptide, but retains essential properties. A typical variant of a polypeptide differs in amino acid sequence from another, reference polypeptide. A variant and reference polypeptide may differ in amino acid sequence by one or more modifications (e.g., substitutions, additions, and/or deletions).

Modifications and changes (e.g., a conservative amino acid substitution) can be made in the structure of the polypeptides of the disclosure without substantially affecting the self-assembly characteristics of the polypeptide. For example, certain amino acids can be substituted for other amino acids in a sequence without appreciable variation in activity. In making such changes, the hydropathic index of amino acids can be considered. The importance of the hydropathic amino acid index in conferring interactive function on a polypeptide is generally understood in the art. It is known that certain amino acids can be substituted for other amino acids having a similar hydropathic index or score and still result in a polypeptide with similar functional activity. It is known in the art that an amino acid can be substituted by another amino acid having a similar hydropathic index and still obtain a functionally equivalent polypeptide.

Substitution of like amino acids can also be made on the basis of charge. In certain embodiments, the substitution of amino acids having an equivalent charge under physiological conditions can be made in the structure of the polypeptides of the disclosure without substantially affecting the self-assembly characteristics of the polypeptide. The following charge states: negatively charged ("−ve"), positively charged ("+ve"), and non-charged or neutral ("neu") under physiological conditions can be assigned to amino acid residues: aspartate (−ve); glutamate (−ve); arginine (+ve); lysine (+ve); histidine (neu or +ve); serine (neu); asparagine (neu); glutamine (neu); glycine (neu); proline (neu); threonine (neu); alanine (neu); cysteine (neu); methionine (neu); valine (neu); leucine (neu); isoleucine (neu); tyrosine (neu); phenylalanine (neu); tryptophan (neu).

Useful peptides can vary in length so long as they retain the ability to self-assemble to an extent useful for one or more of the purposes described herein. The number of amino acid residues in the peptide may range from as few as two α-amino acid residues to more than 200 residues. Typically, peptides which self-assemble have from about 6 to about 200 residues, preferably from about 6 to about 64 residues, more preferably from about 8 to about 36 residues, most preferably from about 8 to about 24 residues. The peptides can be at least six amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. In one embodiment, the peptide has from about 8 to about 16 residues. In another embodiment, the peptide has from about 12 to about 20 residues. In yet another embodiment, the peptide has from about 16 to about 20 residues.

In addition, one or more of the amino acid residues in a self-assembling peptide can be altered or derivatized by the addition of one or more chemical entities including, but not limited to, acyl groups, carbohydrate groups, carbohydrate chains, phosphate groups, farnesyl groups, isofarnesyl groups, fatty acid groups, or a linker which allows for conjugation or functionalization of the peptide. For example, either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group (CH$_3$CO—)) can be present at the N-terminus of a peptide to neutralize an "extra" positive charge that may otherwise be present (e.g., a charge not resulting from the side chain of the N-terminal amino acid). Similarly, a group such as an amine group (RNH—, where R is an organic group (e.g., an amino group —NH$_2$)) can be used to neutralize an "extra" negative charge that may otherwise be present at the C-terminus (e.g., a charge not resulting from the side chain of the C-terminal amino acid residue). Where an amine is used, the C-terminus bears an amide (—CONHR). The neutralization of charges on a terminus may facilitate self-assembly. One of ordinary skill in the art will be able to select other suitable groups.

Useful peptides can also be branched, in which case they will contain at least two amino acid polymers, each of which consists of at least three amino acid residues joined by peptide bonds. The two amino acid polymers may be linked by a bond other than a peptide bond.

While the sequences of the peptides can vary, useful sequences include those that convey an amphiphilic nature to the peptides (e.g., the peptides can contain approximately equal numbers of hydrophobic and hydrophilic amino acid residues), and the peptides can be complementary and structurally compatible. Complementary peptides have the ability to form ionic or hydrogen bonds between residues (e.g., hydrophilic residues) on adjacent peptides in a structure. For example, one or more hydrophilic residues in a peptide can either hydrogen bond or ionically pair with one or more hydrophilic residues on an adjacent peptide. Hydrophilic residues are those residues that typically contain a polar functional group or a functional group that is charged at physiological conditions. Exemplary functional groups include, but are not limited to, carboxylic acid groups, amino groups, sulfate groups, hydroxy groups, halogen groups, nitro groups, phosphate groups, etc. Hydrophobic residues are those residues that contain non-polar functional groups. Exemplary functional groups include, but are not limited to, alkyl groups, alkene groups, alkyne groups, and phenyl groups.

In one embodiment, the hydrophilic residue has the formula —NH—CH(X)—COO—, wherein X has the formula (CH$_2$)$_y$Z, wherein y=0-8, preferably 1-6, more preferably 1-4 and most preferably 1-3, and Z is a polar or charged functional group including, but not limited to, a carboxylic acid group, an amino group, a sulfate group, a hydroxy group, a halogen group, a nitro group, a phosphate group, or a functional group containing a quaternary amine. The alkyl chain can be in a linear, branched, or cyclic arrangement. X may also contain one or more heteroatoms within the alkyl chain and/or X may be substituted with one or more additional substituents. In a preferred embodiment, Z is a carboxylic acid group or an amino group. In one embodiment, the hydrophobic residue has the formula —NH—CH(X)—COO—, wherein X has the formula (CH$_2$)$_y$Z, wherein y=0-8, preferably 1-6, more preferably 1-4, and more preferably 1-3, and Z is a non-polar functional group including, but not limited to, an alkyl group, an alkene group, an alkyne group, or a phenyl group. The alkyl, alkene, or alkyne chain can be in a linear, branched, or cyclic arrangement. X may also contain one or more heteroatoms within the alkyl chain and/or X may be substituted with one or more additional substituents. In a preferred embodiment, X is an alkyl group, such as a methyl group.

In one embodiment, the self-assembling material comprises peptides having a sequence of amino acid residues conforming to one or more of Formulas I-IV:

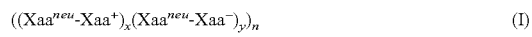

$$((Xaa^{neu}\text{-}Xaa^+)_x(Xaa^{neu}\text{-}Xaa^-)_y)_n \qquad (I)$$

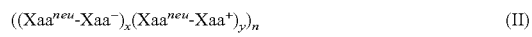

$$((Xaa^{neu}\text{-}Xaa^-)_x(Xaa^{neu}\text{-}Xaa^+)_y)_n \qquad (II)$$

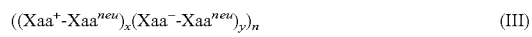

$$((Xaa^+\text{-}Xaa^{neu})_x(Xaa^-\text{-}Xaa^{neu})_y)_n \qquad (III)$$

$$((Xaa^-\text{-}Xaa^{neu})_x(Xaa^+\text{-}Xaa^{neu})_y)_n \qquad (IV)$$

wherein Xaa$^{neu}$ represents an amino acid residue having a neutral charge; Xaa$^+$ represents an amino acid residue having a positive charge; Xaa$^-$ represents an amino acid residue having a negative charge; x and y are integers having a value of 1, 2, 3, or 4, independently; and n is an integer having a value of 1-5. Peptides with modulus I (i.e., peptides having alternate positively and negatively charged R groups on one side (e.g., the polar face of the β-sheet) are described by each of Formulas I-IV, where x and y are 1. Examples of peptides of modulus I include, but are not limited to, RADA (SEQ. ID NO. 57) and RADARADARADARADA (SEQ. ID NO. 1). Examples of peptides of modulus II (i.e., peptides having two residues bearing one type of charge (e.g., a positive charge) followed by two residues bearing another type of charge (e.g., a neutral charge)) are described by the same formulas where both x and y are 2. Examples of peptides of modulus III (i.e., peptides having three residues bearing one type of charge (e.g., a positive charge) followed by three residues bearing another type of charge (e.g., a negative charge)) include, but are not limited to, RARARADADADA (SEQ. ID NO. 112). Examples of peptides of modulus IV (i.e., peptides having three residues bearing one type of charge (e.g., a positive charge) followed by three residues bearing another type of charge (e.g., a negative charge)) include, but are not limited to, RARARARADADADADA (SEQ. ID NO. 113).

Where self-assembling peptides are used, it is thought that their side chains (or R groups) partition into two faces, a polar face with positively and/or negatively charged ionic side chains (e.g., side chains containing —OH, —NH, —CO$_2$H, or —SH groups), and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides may therefore be called ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residues alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV." A peptide having four repeating units of the sequence EAKA (SEQ ID NO: 111) may be designated EAKA16-I (SEQ ID NO: 410), and peptides having other sequences may be described by the same convention.

Other hydrophilic residues that form hydrogen bonds including, but not limited to, asparagine and glutamine, may be incorporated into the peptides. If the alanine residues in the peptides are changed to more hydrophobic residues, such as leucine, isoleucine, phenylalanine or tyrosine, the resulting peptides have a greater tendency to self-assemble and form peptide matrices with enhanced strength. Some peptides that have similar amino acids sequences and lengths as the peptides described herein form alpha-helices and random-coils, rather than beta-sheets, and do not form macroscopic structures. Thus, in addition to self-complementarity, other factors are likely to be important for the formation of macroscopic structures, such as the peptide length, the degree of intermolecular interaction, and the ability to form staggered arrays.

Unpaired residues can interact (e.g., form hydrogen bonds, etc.,) with the solvent. Peptide-peptide interactions may also involve van der Waals forces and/or forces that do not constitute covalent bonds. The peptides are structurally compatible when they are capable of maintaining a sufficiently constant intrapeptide distance to allow self-assembly and structure formation. The intrapeptide distance can vary. "Intrapeptide distance", as used herein, refers to the average of a representative number of distances between adjacent amino acid residues. In one embodiment, the intrapeptide distance is less than about 4 angstroms, preferably less than about 3, more preferably less than about 2 angstroms, and most preferably less than about 1 angstrom. The intrapeptide distance may be larger than this, however. These distances can be calculated based on molecular modeling or based on a simplified procedure described in U.S. Pat. No. 5,670,483 to Zhang, et al.

The structures described herein can be formed through self-assembly of the peptides described in U.S. Pat. Nos. 5,670,483; 5,955,343; 6,548,630; and U.S. Pat. No. 6,800,481 to Zhang, et al.; Holmes, et al., *Proc. Natl. Acad. Sci. USA*, 97:6728-6733 (2000); Zhang, et al., *Proc. Natl. Acad. Sci. USA*, 90:3334-3338 (1993); Zhang, et al., *Biomaterials*, 16:1385-1393 (1995); Caplan et al., *Biomaterials*, 23:219-227 (2002); Leon, et al., *J. Biomater. Sci. Polym. Ed.*, 9:297-312 (1998); and Caplan, et al., *Biomacromolecules*, 1:627-631 (2000).

Self-assembling peptides containing alternating hydrophobic and hydrophilic amino residues can be used. Examples of representative hydrophobic and hydrophilic peptides are listed in Table 1.

TABLE 1

Representative Self-Assembling Peptides

| No. | Sequence (N → C) | |
|---|---|---|
| 1. | n-SGSGSGSGSGSGSGSG-c | (SEQ ID NO: 2) |
| 2. | n-SASASASASASASASA-c | (SEQ ID NO: 3) |
| 3. | n-SVSVSVSVSVSVSVSV-c | (SEQ ID NO: 4) |
| 4. | n-SLSLSLSLSLSLSLSL-c | (SEQ ID NO: 5) |
| 5. | n-SISISISISISISISI-c | (SEQ ID NO: 6) |
| 6. | n-SMSMSMSMSMSMSMSM-c | (SEQ ID NO: 7) |
| 7. | n-SFSFSFSFSFSFSFSF-c | (SEQ ID NO: 8) |
| 8. | n-SWSWSWSWSWSWSWSW-c | (SEQ ID NO: 9) |
| 9. | n-SPSPSPSPSPSPSPSP-c | (SEQ ID NO: 10) |
| 10. | n-TGTGTGTGTGTGTGTG-c | (SEQ ID NO: 11) |
| 11. | n-TATATATATATATATA-c | (SEQ ID NO: 12) |
| 12. | n-TVTVTVTVTVTVTVTV-c | (SEQ ID NO: 13) |
| 13. | n-TLTLTLTLTLTLTLTL-c | (SEQ ID NO: 14) |
| 14. | n-TITITITITITITITI-c | (SEQ ID NO: 15) |
| 15. | n-TMTMTMTMTMTMTMTM-c | (SEQ ID NO: 16) |
| 16. | n-TFTFTFTFTFTFTFTF-c | (SEQ ID NO: 17) |
| 17. | n-TWTWTWTWTWTWTWTW-c | (SEQ ID NO: 18) |
| 18. | n-TPTPTPTPTPTPTPTP-c | (SEQ ID NO: 19) |
| 19. | n-CGCGCGCGCGCGCGCG-c | (SEQ ID NO: 20) |
| 20. | n-CACACACACACACACA-c | (SEQ ID NO: 21) |
| 21. | n-CVCVCVCVCVCVCVCV-c | (SEQ ID NO: 22) |
| 22. | n-CLCLCLCLCLCLCLCL-c | (SEQ ID NO: 23) |

TABLE 1-continued

Representative Self-Assembling Peptides

| No. | Sequence (N → C) | |
|---|---|---|
| 23. | n-CICICICICICICI-c | (SEQ ID NO: 24) |
| 24. | n-CMCMCMCMCMCMCM-c | (SEQ ID NO: 25) |
| 25. | n-CFCFCFCFCFCFCF-c | (SEQ ID NO: 26) |
| 26. | n-CWCWCWCWCWCWCW-c | (SEQ ID NO: 27) |
| 27. | n-CPCPCPCPCPCPCP-c | (SEQ ID NO: 28) |
| 28. | n-YGYGYGYGYGYGYG-c | (SEQ ID NO: 29) |
| 29. | n-YAYAYAYAYAYAYA-c | (SEQ ID NO: 30) |
| 30. | n-YVYVYVYVYVYVYV-c | (SEQ ID NO: 31) |
| 31. | n-YLYLYLYLYLYLYL-c | (SEQ ID NO: 32) |
| 32. | n-YIYIYIYIYIYIYI-c | (SEQ ID NO: 33) |
| 33. | n-YMYMYMYMYMYMYM-c | (SEQ ID NO: 34) |
| 34. | n-YFYFYFYFYFYFYF-c | (SEQ ID NO: 35) |
| 35. | n-YWYWYWYWYWYWYW-c | (SEQ ID NO: 36) |
| 36. | n-YPYPYPYPYPYPYP-c | (SEQ ID NO: 37) |
| 37. | n-NGNGNGNGNGNGNG-c | (SEQ ID NO: 38) |
| 38. | n-NANANANANANANA-c | (SEQ ID NO: 39) |
| 39. | n-NVNVNVNVNVNVNV-c | (SEQ ID NO: 40) |
| 40. | n-NLNLNLNLNLNLNL-c | (SEQ ID NO: 41) |
| 41. | n-NINININININININI-c | (SEQ ID NO: 42) |
| 42. | n-NMNMNMNMNMNMNM-c | (SEQ ID NO: 43) |
| 43. | n-NFNFNFNFNFNFNF-c | (SEQ ID NO: 44) |
| 44. | n-NWNWNWNWNWNWNW-c | (SEQ ID NO: 45) |
| 45. | n-NPNPNPNPNPNPNP-c | (SEQ ID NO: 46) |
| 46. | n-QGQGQGQGQGQGQG-c | (SEQ ID NO: 47) |
| 47. | n-QAQAQAQAQAQAQA-c | (SEQ ID NO: 48) |
| 48. | n-QVQVQVQVQVQVQV-c | (SEQ ID NO: 49) |
| 49. | n-QLQLQLQLQLQLQL-c | (SEQ ID NO: 50) |
| 50. | n-QIQIQIQIQIQIQI-c | (SEQ ID NO: 51) |
| 51. | n-QMQMQMQMQMQMQM-c | (SEQ ID NO: 52) |
| 52. | n-QFQFQFQFQFQFQF-c | (SEQ ID NO: 53) |
| 53. | n-QWQWQWQWQWQWQW-c | (SEQ ID NO: 54) |
| 54. | n-QPQPQPQPQPQPQP-c | (SEQ ID NO: 55) |
| 55. | n-AEAKAEAKAEAKAEAK-c | (SEQ ID NO: 56) |
| 56. | n-RADARADARADARADA-c | (SEQ ID NO: 1) |
| 57. | n-RAEARAEARAEARAEA-c | (SEQ ID NO: 58) |
| 58. | n-KADAKADAKADAKADA-c | (SEQ ID NO: 59) |

Other peptides or proteins can be used in combination or alternation with the disclosed self-assembling peptides or compositions. It will be appreciated that the additional peptides can include other self-assembling peptides or proteins. Alternatively, the peptide may be peptides that do not self-assemble. Representative additional peptides, proteins, or chemically modified variants thereof include, but are not limited to the peptides provided in Table 2.

TABLE 2

Additional Peptides

| No. | Sequence (N → C) | |
|---|---|---|
| 1. | Pmp-Y(Me)-I-T-N-C-P-Orn-Y-$NH_2$ | (SEQ ID NO: 60) |
| 2. | Mpr-Y-F-Q-N-C-P-R | (SEQ ID NO: 61) |
| 3. | C-Y-F-Q-N-C-P-R-G-$NH_2$ | (SEQ ID NO: 62) |
| 4. | C-Y-F-Q-N-C-P-R | (SEQ ID NO: 63) |
| 5. | C-Y-Ile-Q-N-C-P-R-G-$NH_2$ | (SEQ ID NO: 64) |
| 6. | Y-F-Q-N-Asu-P-R-G-$NH_2$ | (SEQ ID NO: 65) |
| 7. | Y-Ile-Q-N-Asu-P-R-G-$NH_2$ | (SEQ ID NO: 66) |
| 8. | Mpr-D-PyridylAnine-F-Q-N-C-P-R-G-$NH_2$ | (SEQ ID NO: 67) |
| 9. | Deamino-Pen-Y-F-V-N-C-P-DR-G-$NH_2$ | (SEQ ID NO: 68) |
| 10. | Mpr-Y-F-Q-N-C-P-R-G-$NH_2$ | (SEQ ID NO: 69) |
| 11. | Mpr-Y-F-Q-N-C-P-DR-G-$NH_2$ | (SEQ ID NO: 70) |
| 12. | Mpr-Y-F-Q-N-C-P-K | (SEQ ID NO: 71) |
| 13. | C-Y-F-Q-N-C-P-K-G-$NH_2$ | (SEQ ID NO: 72) |
| 14. | C-Y-F-Q-N-C-P-K | (SEQ ID NO: 73) |
| 15. | Mpr-Y-F-V-N-C-P-DR-G-$NH_2$ | (SEQ ID NO: 74) |
| 16. | C-F-Ile-Q-N-C-P-Orn-G-$NH_2$ | (SEQ ID NO: 75) |
| 17. | Pmp-DY(OEt)-F-V-N-C-P-Cit-G-$NH_2$ | (SEQ ID NO: 76) |
| 18. | Pmp-Y(OEt)-F-V-N-C-P-R-G-$NH_2$ | (SEQ ID NO: 77) |
| 19. | Pmp-Y(Me)-F-Q-N-C-P-R-G-$NH_2$ | (SEQ ID NO: 78) |
| 20. | Pmp-Y(Me)-I-Q-N-C-P-Orn-G-$NH_2$ | (SEQ ID NO: 79) |
| 21. | G-DR-G-D-S-P | (SEQ ID NO: 80) |
| 22. | G-DR-G-D-S-P-A-S-S-K | (SEQ ID NO: 81) |
| 23. | G-P-R | |

TABLE 2-continued

Additional Peptides

| No. | Sequence (N → C) |
|---|---|
| 24. | G-Pen-G-R-G-D-S-P-C-A (SEQ ID NO: 82) |
| 25. | GRADSP (SEQ ID NO: 83) |
| 26. | GRGD-DS-P (SEQ ID NO: 84) |
| 27. | GRGDNP (SEQ ID NO: 85) |
| 28. | GRGDS (SEQ ID NO: 86) |
| 29. | GRGDSP (SEQ ID NO: 87) |
| 30. | GRGDSPC (SEQ ID NO: 88) |
| 31. | GRGDSPK (SEQ ID NO: 89) |
| 32. | GRGDTP (SEQ ID NO: 90) |
| 33. | GRGES (SEQ ID NO: 91) |
| 34. | GRGESP (SEQ ID NO: 92) |
| 35. | GRGETP (SEQ ID NO: 93) |
| 36. | KGDS (SEQ ID NO: 94) |
| 37. | GAVSTA (SEQ ID NO: 95) |
| 38. | WTVPTA (SEQ ID NO: 96) |
| 39. | TDVNGDGRHDL (SEQ ID NO: 97) |
| 40. | REDV (SEQ ID NO: 98) |
| 41. | RGDC (SEQ ID NO: 99) |
| 42. | RGDS (SEQ ID NO: 100) |
| 43. | RGDSPASSKP (SEQ ID NO: 101) |
| 44. | RGDT (SEQ ID NO: 102) |
| 45. | RGDV (SEQ ID NO: 103) |
| 46. | RGES (SEQ ID NO: 104) |
| 47. | SDGR (SEQ ID NO: 105) |
| 48. | SDGRG (SEQ ID NO: 106) |
| 49. | YRGDS (SEQ ID NO: 107) |
| 50. | EGVNDNEEGFFSAR (SEQ ID NO: 108) |
| 51. | YADSGEGDFLAEGGGVR (SEQ ID NO: 109) |
| 52. | Glp-GVNDNEEGFFSARY (SEQ ID NO: 110) |

Pmp = pyridoxamine phosphate
Mpr = 3-mercaptopropionyl
Deamino-Pen = deamino penicillamine
Pen = penicillamine
Asu = amino succinyl
OEt = ethoxy
Me = methyl
Cit = citruline Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another through the formation of disulfide bonds. Structures bonded in this manner may have increased mechanical strength relative to structures made with comparable peptides that do not include cysteine residues and thus are unable to form disulfide bonds.

The amino acid residues in the self-assembling peptides can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrrolysine or selenocysteine and ornithine). Non-naturally occurring amino acids are not found or have not been found in nature, but can be incorporated into a peptide chain. Suitable non-naturally occurring amino acids include, but are not limited to, D-alloisoleucine (2R,3S)-2-amino-3-methylpentanoic acid, L-cyclopentyl glycine (S)-2-amino-2-cyclopentyl acetic acid. Other examples of non-naturally occurring amino acids can be found in textbooks or on the worldwide web (e.g., a site is maintained by the California Institute of Technology which displays structures of non-natural amino acids that have been successfully incorporated into functional proteins). Non-natural amino acid residues and amino acid derivatives described in U.S. Patent Application Publication No. 2004/0204561 to Ellison.

Self-assembling peptides can be chemically synthesized or purified from natural or recombinantly-produced sources by methods well known in the art. For example, peptides can be synthesized using standard F-moc chemistry.

Standard Fmoc (9-florenylmethoxycarbonyl) derivatives include Fmoc-Asp(OtBu)-OH, Fmoc-Arg(Pbf)-OH, and Fmoc-Ala-OH. Couplings are mediated with DIC (diisopropylcarbodiimide)/6-Cl-HOBT (6-chloro-1-hydroxybenzotriazole). In some embodiments, the last four residues of the peptide require one or more recoupling procedures. In particular, the final Fmoc-Arg(Pbf)-OH coupling can require recoupling. For example, a second or third recoupling can be carried out to complete the peptide using stronger activation chemistry such as DIC/HOAT (1-hydroxy-7-azabenzotriazole) or HATU (1-[bis(dimethylamino)methylene]-1H-1,2,3-triazolo[4,5-b]pyridinium 3-oxid hexafluorophosphate)/ NMM (N-methylmorpholine).

Acidolytic cleavage of the peptide can be carried out with the use of carbocation scavengers (thioanisole, anisole and $H_2O$). Optimization can be achieved by varying the ratio of the components of the cleavage mixture. An exemplary cleavage mixture ratio is 90:2.5:2.5:5 (trifluoroacetic acid (TFA)-:thioanisole-anisole-$H_2O$). The reaction can be carried out for 4 hr. at room temperature.

In some embodiments the removal of residual impurities is carried out by wash steps. For example, TFA and organic impurities can be eliminated by precipitation and repeated washes with cold diethyl ether and methyl t-butyl ether (MTBE).

Peptides produced using the disclosed methods can be purified using high pressure liquid chromatography (HPLC). Suitable solvents for dissolving the peptides include neat trifluoroacetic acid (TFA). In some embodiments, 8 mL TFA/g peptide is sufficient to fully dissolve peptides following precipitation. For example, TFA can be diluted into $H_2O$ for use in the disclosed methods. Typically, the peptides remain soluble at TFA concentrations of 0.5% to 8% and can be loaded onto reverse phase (RP)-HPLC columns for salt exchange. Exemplary salt exchange methods use 3-4 column volumes of acidic buffer to wash away the TFA counter ion due to its stronger acidity coefficient. Buffers suitable for use in washing away the TFA counter ion include 0.1% HCl in $H_2O$.

Following removal of TFA, peptides can be eluted with a step gradient. Exemplary elution buffers include 30% acetonitrile (MeCN) vs. 0.1% HCl in $H_2O$. For acetate exchange, peptides can be loaded from the same diluted TFA solution, washed with 3-4 column volumes of 1% acetic acid (AcOH) in $H_2O$, followed by 2 column volumes of 0.1 M $NH_4OAc$ in $H_2O$, pH 4.4. In some embodiments the column is washed again with 3-4 column volumes of 1% AcOH in $H_2O$.

Peptides can be eluted from the columns using a step gradient of 30% MeCN vs. 1% AcOH in $H_2O$. In some embodiments the elution of peptides can be enhanced acetate exchange. Exemplary buffers for acetate exchange include 0.1 M $NH_4OAc$ in $H_2O$, pH 4.4.

Analytical HPLC can be carried out to assess the purity and homogeneity of peptides. An exemplary HPLC column for use in analytical HPLC is a PHENOMENEX® JUPITER® column. In some embodiments analytical HPLC is carried out using a column and buffer that are heated to a temperature that is greater than 25° C., for example 25-75° C. In a particular embodiment analytical HPLC is carried out at temperatures of about 65° C. A step gradient can be used to separate the peptide composition. In some embodiments the gradient is from 1%-40% MeCN vs 0.05% TFA in $H_2O$. The change in gradient can be achieved over 20 min using a flow rate of 1 ml/min. Peptides can be detected using UV detection at 215 nm.

Self-complementary peptides such as EAKA16-I (SEQ. ID NO. 410), RADA16-I (SEQ. ID NO. 1), RAEA16-I (SEQ. ID NO. 58), and KADA16-I (SEQ. ID NO. 59) are described in Zhang, et al. ((1999) Peptide self-assembly in functional polymer science and engineering. Reactive & Functional Polymers, 41, 91-102).

Peptide-based structures can be formed of heterogeneous mixtures of peptides (i.e., mixtures containing more than one type of peptide conforming to a given formula or to two or more of the formulas). In some embodiments, each of the types of peptides in the mixture is able to self-assemble alone. In other embodiments, one or more of each type of peptide would not, alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides, which are complementary and structurally compatible to each other, can be used.

In a preferred embodiment, one or more short amino acid sequences that assists in self-assembly (referred to as assembly assist sequences) can be added to a homogeneous or heterogeneous mixture of amino acid sequences that alone do not self-assemble. The assembly assist sequences contain amino acids that are complementary with the amino acids in the sequences in the mixture. The assembly assist sequences may contain any number of amino acids. Preferably, the assembly assist sequences contain at least 4 amino acids. The assembly assist sequences may contain a flexible linker between the amino acids that assists in self-assembly. For example, the assembly assist sequence may contain a pair, a triad, or a quartet of assembly assisting amino acids at the termini of the sequence which are connected via a flexible linker. Suitable assembly assist sequences include, but are not limited to, RADA (SEQ ID NO: 57) and EAKA (SEQ ID NO: 111).

Suitable linkers include, but are not limited to, ether based tethers such as polyethylene glycol (PEG), N-succinimidyl 3-(2-pyridyldithio)propionate (SPDP, 3- and 7-atom spacer), long-chain-SPDP (12-atom spacer), (succinimidyloxycarbonyl-α-methyl-2-(2-pyridyldithio) toluene) (SMPT, 8-atom spacer), succinimidyl-4-(N-maleimidomethyl)cyclohexane-1-carboxylate) (SMCC, 11-atom spacer) and sulfosuccinimidyl-4-(N-maleimidomethyl)cyclohexane-1-carboxylate, (sulfo-SMCC, 11-atom spacer), m-maleimidobenzoyl-N-hydroxysuccinimide ester (MBS, 9-atom spacer), N-(γ-maleimidobutyryloxy) succinimide ester (GMBS, 8-atom spacer), N-(γ-maleimidobutyryloxy) sulfosuccinimide ester (sulfo-GMBS, 8-atom spacer), succinimidyl 6-((iodoacetyl) amino) hexanoate (SIAX, 9-atom spacer), succinimidyl 6-(6-(((4-iodoacetyl)amino)hexanoyl)amino)hexanoate (SIAXX, 16-atom spacer), and p-nitrophenyl iodoacetate (NPIA, 2-atom spacer). One ordinarily skilled in the art also will recognize that a number of other linkers, with different numbers of atoms, may be used.

The compositions described herein regardless of the precise form (e.g., whether in a liquid form or molded) and regardless of the overall compositions (e.g., whether combined with another agent, contained within a device, or packaged in a kit) can include a mixture of one or more peptide chains.

Self-assembled structures can be formed that have varying degrees of stiffness or elasticity. The structures typically have a low elastic modulus (e.g., a modulus in the range of about 0.01 to about 1000 kPa, preferably from about 1 to about 100 kPa, more preferably from about 1 to about 10 kPa as measured by standard methods, such as in a standard cone-plate rheometer). Low values may be preferable, as they permit structure deformation as a result of movement, in response to pressure, in the event of cell contraction. More specifically, stiffness can be controlled in a variety of ways, including by changing the length, sequence, and/or concentration of the precursor molecules (e.g., self-assembling peptides). Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are within the scope of the present invention. For example, amino acid residues with polymerizable groups, including but not limited to vinyl groups, may be incorporated and cross-linked by exposure to UV light. The extent of crosslinking can be precisely controlled by applying the radiation for a predetermined length of time. The extent of crosslinking can be determined by light scattering, gel filtration, or scanning electron microscopy using methods well known in the art. Furthermore, crosslinking can be examined by HPLC or mass spectrometry analysis of the structure after digestion with a protease, such as matrix metalloproteases. Material strength may be determined before and after cross-linking. Regardless of whether cross-linking is achieved by a chemical agent or light energy, the molecules may be cross-linked in the course of creating a mold or when peptide-containing solutions are applied to the body. Further, self-assembling peptide chains can be crosslinked to form a spider web-type pattern to reinforce the material in vivo. The crosslinks serve to reinforce the material providing increased rigidity and strength. For example, the self-assembling material can be applied to a wound, wherein the periphery of the material is functionalized with polymerizable groups. Upon crosslinking, the periphery of the material becomes more rigid, anchoring the material to the wound site, while the interior of material remains flexible to move as the body moves.

The half-life (e.g., the in vivo half-life) of the structures can also be modulated by incorporating protease or peptidase cleavage sites into the precursors that subsequently form a given structure. Proteases or peptidases that occur naturally in vivo or that are introduced (e.g., by a surgeon) can then promote degradation by cleaving their cognate substrates.

Combinations of any of the modifications described here can be made. For example, self-assembling peptides that include a protease cleavage site and a cysteine residue and/or a cross-linking agent, kits and devices containing them, and methods of using them can be utilized.

The peptide structures formed from any self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

In another embodiment, the self-assembling materials can anchor or interact with the structural extracellular matrix (ECM) at the edges of blood vessels and/or tissues are described herein. These self-assembling materials typically have hydrophobic and/or hydrophilic sections which allow the material to react or interact with the glycoproteins found in the ECM.

Preferably, the self-assembling materials when they breakdown, do not cause any secondary toxicity. Further, the break down product of the self-assembling materials would be suitable for the growth and repair of the surrounding tissues.

1. Other Self-assembling Materials

Another embodiment provides self-assembling peptides having a segment of residues having a positive charge under physiological conditions joined to a segment of residues having a negative charge under physiological conditions. The segment of positively or negatively charged residues can include about 2 to about 50 amino acid residues, typically about 3 to about 30 residues, more typically about 10 to about 20 amino acid residues. In another embodiment, about half of the residues of the self-assembling peptide are positively charged and the other half of the self-assembling peptide has negatively charged amino acid residues. A combination of these peptides can self-assemble by matching the positive end of a first self-assembling peptide to the negative end of a second self-assembling peptide. The negative end of the first self-assembling peptide will match up or align with the positive end of the second self-assembling peptide. The self-assembling peptides will stack-up or aggregate based on opposite ends of the self-assembling peptides being attacked based on charge at physiological compositions. One representative embodiment provides a self-assembling peptide having the following sequence RRRR-DDDD (SEQ ID NO: 114) or GGGG-SSSS (SEQ ID NO: 115).

In still another embodiment, the self-assembling peptide has a first hydrophobic region operably linked to a first hydrophilic region. The first hydrophobic region can include a segment of amino acid residues that have hydrophobic side chains under physiological conditions. The first hydrophilic region can include a segment of amino acid residues that have hydrophilic side chains under physiological conditions. In this embodiment, the hydrophobic ends of the self-assembling peptides would assemble with other hydrophobic ends and the hydrophilic ends would assemble with other hydrophilic ends. Assembly can be controlled by altering the environment of the peptides. Such materials could be used to coat the inside of a lumen. The hydrophobic ends would likely interact with the ECM of the lumen surface sealing the surface while the hydrophilic ends extend out towards the center of the lumen. Fluids would continue to flow through the lumen. As the material degrades and/or is removed from the lumen surface, material would flow in from other areas and again anchor to the lumen surface, thus the composition acts a reservoir providing new material as needed. Alternatively, additional material could be administered to replace material that has worn or been degraded. In another embodiment, the material can be used as dynamic patches, for example, in the treatment of ulcers or for use in the intestine.

Another embodiment provides a self-assembling peptide that contains a segment of residues that have either a positive or negative charge under physiological conditions. Representative amino acid sequences for positively charged self-assembling peptides include, but are not limited to, KKKK (SEQ ID NO: 116), RRRR (SEQ ID NO: 117), or HHHH (SEQ ID NO: 118). Representative amino acid sequences for negatively charged self-assembling peptides include, but are not limited to, DDDD (SEQ ID NO: 119) or EEEE (SEQ ID NO: 120). When combined, a string of positively charged amino acid residues will align parallel and opposite with a string of negatively charged amino acid residues. In certain embodiments, strings of positively charged amino acids will alternate with strings of negatively charged amino acids to for a multilayered structure.

Still another embodiment provides self-assembling peptides that have a combination of hydrophilic polar amino acid residues and hydrophobic non-polar amino acid residues under physiological conditions. The one or more hydrophilic residues can alternate with one or more hydrophobic residues. For example, the amino acid sequence of a representative self-assembling peptide can be GQGQ (SEQ ID NO: 121), GGQQGG (SEQ ID NO: 122), GQQGQQG (SEQ ID NO: 123), GGQGGQGG (SEQ ID NO: 124), etc. It will be appreciated that the partitioning of the self-assembling peptide into a polar or non-polar environment can be controlled by altering the ratio of hydrophobic amino acid residues to hydrophilic amino acid residues, wherein a ratio greater than 1:1 indicates that the peptide partitions more in hydrophobic conditions compared to hydrophilic conditions. A ratio of less than 1:1 indicates that the peptide partitions more in hydrophilic conditions compared to hydrophobic conditions.

Combinations of any of the modifications described here can be made. For example, self-assembling peptides that include a protease cleavage site and a cysteine residue and/or a cross-linking agent, kits and devices containing them, and methods of using them can be utilized. The compositions can be used to prevent or limit movement of a bodily fluid, to stabilize tissue or cells, or to prevent contamination when administered to a site in need thereof. The compositions can be in the form of a dry powder, a wafer, a disk, a tablet, a capsule, a liquid, a gel, a cream, a foam, an ointment, an emulsion, a coating on a stent, catheter or other medical implant, the peptides incorporated into a microparticle, a polymeric matrix, a hydrogel, a fabric, a bandages, a suture, or a sponge.

B. Non-peptide Materials which Self-assemble

Another class of materials that can self-assemble is peptidomimetics. Peptidomimetics, as used herein, refers to molecules, which mimic peptide structure. Peptidomimetics have general features analogous to their parent structures, polypeptides, such as amphiphilicity. Examples of such peptidomimetic materials are described in Moore et al., Chem. Rev. 101(12), 3893-4012 (2001).

The peptidomimetic materials can be classified into four categories: α-peptides, β-peptides, γ-peptides, and δ-peptides. Copolymers of these peptides can also be used.

Examples of α-peptide peptidomimetics include, but are not limited to, N,N'-linked oligoureas, oligopyrrolinones, oxazolidin-2-ones, azatides and azapeptides.

Examples of β-peptides include, but are not limited to, β-peptide foldamers, β-aminoxy acids, sulfur-containing β-peptide analogues, and hydrazino peptides.

Examples of γ-peptides include, but are not limited to, γ-peptide foldamers, oligoureas, oligocarbamates, and phosphodiesters.

Examples of δ-peptides include, but are not limited to, alkene-based δ-amino acids and carbopeptoids, such as pyranose-based carbopeptoids and furanose-based carbopeptoids.

1. Peptidomimetics and Oligomers Having Backbones, which can Adopt Helical, Sheet, or Lattice Confirmations Another class of compounds that self-assemble includes oligomers having backbones, which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo(pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as olihothiophenes with chiral p-phenyloxazoline side chains, and oligo(m-phenylene-ethynylene)s.

Examples of compound containing backbones utilizing hydrogen bonding interactions include, but are not limited to, aromatic amide backbones such as oligo(acylated 2,2'-bipyridine-3,3'-diamine)s and oligo(2,5-bis[2-aminophenyl]pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-phenylene ethynylene)s containing metal-coordinating cyano groups, and hexapyrrins.

2. Nucleotidomimetics

Another class of molecules, which can self-assemble are nucleotidomimetics such as isomeric oligonucleotides, modified carbohydrates, nucleotides with modified nucleotide linkages, and nucleotides with alternative nucleobases.

Examples of isomeric nucleotides include, but are not limited to, iso-RNA and iso-DNA and α-DNA (change in the anomeric configuration from β to α), alt-DNA, and 1-DNA.

Examples of modified carbohydrates include, but are not limited to, backbones with C1'-bases connectivities such as tetrofuranosyl oligonucleotides, pentopyranosyl oligonucleotides, and hexopyranosyl oligonucleotides; backbones with C2'-base connectivities such as isonucleotides (repositioning of the base sugar connection from C1 to the C2 position), HNAs (insertion of an additional methylene group between the 04' and C1' position of a furanose), ANAs (incorporation of a C3'-(S)-hydroxyl group), MNAs (inversion of the C3'-OH configuration from (S) in ANAs to (R)), CNAs (replacement of the O of the hexose with a methylene group), CeNAs (introduction of a 5'-6' alkene within the analogous ring), as well as other ring systems, torsionally restricted oligonucleotides such as bicyclic oligonucleotides, LNAs (restriction of the pentofaranose backbone to the 3'-endo configuration), torsionally flexible oligonucleotides such as base sugar extensions (insertion of methylene and ethylene groups into both α- and β-deoxynucleotides) and acyclic backbones (glycerol derivatives incorporating phosphodiester linkages).

Examples of nucleotides with modified nucleotide linkages include, but are not limited to, PNAs (peptide nucleic acids), NDPs (nucleo-δ-peptides), fused sugar-base backbones, and cationic linkages.

Examples of alternative nucleobases include, but are not limited to, nucleotides with alternative aromatic nucleobases.

3. Other Materials

Other materials, which can self-assemble include N-alkylacrylamide oligomers and di- and triblock co-polymers. N-alkylacrylamides can assume self-assembled into sheet-like structures (see Kendhale, et al., *Chem Comm.*). Examples of block copolymers include copolypeptides, polypeptide-PEGS, PEO-polybutadienes, PEG-polysaccharides, etc.

Another class of materials which are known to self-assemble are dendrimers. "Dendrimers", as used herein, refers to branched polymers with successive shells of branch units surrounding central core. Dendrimers can self-assemble through a variety of different mechanisms, such as hydrogen bonding, ionic interactions, hydrophobic interactions, solvent interaction, side chain interactions, and the like. Non-limiting examples of self-assembling dendrimers are described in Zimmerman, et al., *Science*, Vol. 271, No. 5252, 1095-1098 (1996); Zimmerman, et al., *J. Am. Chem. Soc.*, 124(46), 13757-13769 (2002); and Frechet, *Proc. Nat. Acad. Sci.*, Vol. 99, No. 8, 4782-4787 (2002).

C. Modification of Self-assembling Materials to Target Specific Tissues

The self-assembling material may further contain a tissue specific component. The tissue specific component can be peptides, polysaccharides, or glycoproteins that are specific for eye, brain, or skin cells. For example, cell surface carbohydrates are major components of the outer surface of mammalian cells and are very often characteristic of cell types. It is assumed that cell type-specific carbohydrates are involved in cell-cell interaction. The tissue specific component can therefore, target these cell specific surface carbohydrates.

Additionally, hydrophobic or hydrophilic tails can be added to the self-assembling material. The tails can interact with cell membranes, thus anchoring the self-assembling material on to the cell surface. Table 3 shows a list of peptides with hydrophobic tails. Hydrophilic tails can also be added to the peptide, alone or in addition to hydrophobic tails, to facilitate interaction with the ECM of different vessels or tissues, such as the bladder.

TABLE 3

Hydrophobic Tails

| No. | Sequence (N → C) | |
|---|---|---|
| 1 | GGGGGDGDGDGDGD | (SEQ. ID NO. 126) |
| 2 | GGGGGEGEGEGEGE | (SEQ. ID NO. 127) |
| 3 | GGGGGKGKGKGKGK | (SEQ. ID NO. 128) |
| 4 | GGGGGRGRGRGRGR | (SEQ. ID NO. 129) |
| 5 | GGGGGHGHGHGHGH | (SEQ. ID NO. 130) |
| 6 | AAAAADADADADAD | (SEQ. ID NO. 131) |
| 7 | AAAAAEAEAEAEAE | (SEQ. ID NO. 132) |
| 8 | AAAAAKAKAKAKAK | (SEQ. ID NO. 133) |
| 9 | AAAAARARARARAR | (SEQ. ID NO. 134) |
| 10 | AAAAAHAHAHAHAH | (SEQ. ID NO. 135) |
| 11 | VVVVVDVDVDVDVD | (SEQ. ID NO. 136) |
| 12 | VVVVVEVEVEVEVE | (SEQ. ID NO. 137) |
| 13 | VVVVVKVKVKVKVK | (SEQ. ID NO. 138) |
| 14 | VVVVVRVRVRVRVR | (SEQ. ID NO. 139) |

TABLE 3-continued

Hydrophobic Tails

| No. | Sequence (N → C) | |
|---|---|---|
| 15 | VVVVVHVHVHVHVH | (SEQ. ID NO. 140) |
| 16 | LLLLLDLDLDLDLD | (SEQ. ID NO. 141) |
| 17 | LLLLLELELELELE | (SEQ. ID NO. 142) |
| 18 | LLLLLKLKLKLKLK | (SEQ. ID NO. 143) |
| 19 | LLLLLRLRLRLRLR | (SEQ. ID NO. 144) |
| 20 | LLLLLHLHLHLHLH | (SEQ. ID NO. 145) |
| 21 | IIIIIDIDIDIDID | (SEQ. ID NO. 146) |
| 22 | IIIIIEIEIEIEIE | (SEQ. ID NO. 147) |
| 23 | IIIIIKIKIKIKIK | (SEQ. ID NO. 148) |
| 24 | IIIIIRIRIRIRIR | (SEQ. ID NO. 149) |
| 25 | IIIIIHIHIHIHIH | (SEQ. ID NO. 150) |
| 26 | MMMMMDMDMDMDMD | (SEQ. ID NO. 151) |
| 27 | MMMMMEMEMEMEME | (SEQ. ID NO. 152) |
| 28 | MMMMMKMKMKMKMK | (SEQ. ID NO. 153) |
| 29 | MMMMMRMRMRMRMR | (SEQ. ID NO. 154) |
| 30 | MMMMMHMHMHMHMH | (SEQ. ID NO. 155) |
| 31 | FFFFFDFDFDFDFD | (SEQ. ID NO. 156) |
| 32 | FFFFFEFEFEFEFE | (SEQ. ID NO. 157) |
| 33 | FFFFFKFKFKFKFK | (SEQ. ID NO. 158) |
| 34 | FFFFFRFRFRFRFR | (SEQ. ID NO. 159) |
| 35 | FFFFFHFHFHFHFH | (SEQ. ID NO. 160) |
| 36 | WWWWWDWDWDWDWD | (SEQ. ID NO. 161) |
| 37 | WWWWWEWEWEWEWE | (SEQ. ID NO. 162) |
| 38 | WWWWWKWKWKWKWK | (SEQ. ID NO. 163) |
| 39 | WWWWWRWRWRWRWR | (SEQ. ID NO. 164) |
| 40 | WWWWWHWHWHWHWH | (SEQ. ID NO. 165) |
| 41 | PPPPPDPDPDPDPD | (SEQ. ID NO. 166) |
| 42 | PPPPPEPEPEPEPE | (SEQ. ID NO. 167) |
| 43 | PPPPPKPKPKPKPK | (SEQ. ID NO. 168) |
| 44 | PPPPPRPRPRPRPR | (SEQ. ID NO. 169) |
| 45 | PPPPPHPHPHPHPH | (SEQ. ID NO. 170) |
| 46 | AAAAARADARADARAD | (SEQ. ID NO. 171) |
| 47 | AAAAARARADADARAR | (SEQ. ID NO. 172) |
| 48 | AAAAAEAKAEAKAEAK | (SEQ. ID NO. 173) |
| 49 | AAAAAEAEAKAKAEAE | (SEQ. ID NO. 174) |
| 50 | AAAAARAEARAEARAE | (SEQ. ID NO. 175) |
| 51 | AAAAARARAEAEARAE | (SEQ. ID NO. 176) |
| 52 | AAAAAKADAKADAKAD | (SEQ. ID NO. 177) |

TABLE 3-continued

Hydrophobic Tails

| No. | Sequence (N → C) | |
|---|---|---|
| 53 | AAAAAEAHAEAHAEAH | (SEQ. ID NO. 178) |
| 54 | AAAAAEAEAHAHAEAE | (SEQ. ID NO. 179) |
| 55 | AAAAARARARARARAR | (SEQ. ID NO. 180) |
| 56 | AAAAARARARARADAD | (SEQ. ID NO. 181) |
| 57 | AAAAARARARADADAD | (SEQ. ID NO. 182) |
| 58 | AAAAAHADAHADAHAD | (SEQ. ID NO. 183) |
| 59 | AAAAAHAHAHAHAHAH | (SEQ. ID NO. 184) |
| 60 | AAAAAHADADAHADAD | (SEQ. ID NO. 185) |
| 61 | AAAAAHAEAEAHAEAE | (SEQ. ID NO. 186) |
| 62 | GGGGGRGDRGDGRGD | (SEQ. ID NO. 187) |
| 63 | GGGGGRGRGDGDGRGR | (SEQ. ID NO. 188) |
| 64 | GGGGGEGKGEGKGEGK | (SEQ. ID NO. 189) |
| 65 | GGGGGEGEGKGKGEGE | (SEQ. ID NO. 190) |
| 66 | GGGGGRGEGEGRGE | (SEQ. ID NO. 191) |
| 67 | GGGGGRGRGEGEGRGE | (SEQ. ID NO. 192) |
| 68 | GGGGGKGDGKGDGKGD | (SEQ. ID NO. 193) |
| 69 | GGGGGEGHGEGHGEGH | (SEQ. ID NO. 194) |
| 70 | GGGGGEGEGHGHGEGE | (SEQ. ID NO. 195) |
| 71 | GGGGGRGRGRGRGRGR | (SEQ. ID NO. 196) |
| 72 | GGGGGRGRGRGRGDGD | (SEQ. ID NO. 197) |
| 73 | GGGGGRGRGRGDGDGD | (SEQ. ID NO. 198) |
| 74 | GGGGGHGDGHGDGHGD | (SEQ. ID NO. 199) |
| 75 | GGGGGHGHGHGHGHGH | (SEQ. ID NO. 200) |
| 76 | GGGGGHGDGDGHGDGD | (SEQ. ID NO. 201) |
| 77 | GGGGGHGEGEGHGEGE | (SEQ. ID NO. 202) |
| 78 | VVVVVRVDVRVDVRVD | (SEQ. ID NO. 203) |
| 79 | VVVVVRVRVDVDVRVR | (SEQ. ID NO. 204) |
| 80 | VVVVVEVKVEVKVEVK | (SEQ. ID NO. 205) |
| 81 | VVVVVEVEVKVKVEVE | (SEQ. ID NO. 206) |
| 82 | VVVVVRVEVRVEVRVE | (SEQ. ID NO. 207) |
| 83 | VVVVVRVRVEVEVRVE | (SEQ. ID NO. 208) |
| 84 | VVVVVKVDVKVDVKVD | (SEQ. ID NO. 209) |
| 85 | VVVVVEVHVEVHVEVH | (SEQ. ID NO. 210) |
| 86 | VVVVVEVEVHVHVEVE | (SEQ. ID NO. 211) |
| 87 | VVVVVRVRVRVRVRVR | (SEQ. ID NO. 212) |
| 88 | VVVVVRVRVRVRVDVD | (SEQ. ID NO. 213) |
| 89 | VVVVVRVRVRVDVDVD | (SEQ. ID NO. 214) |
| 90 | VVVVVHVDVHVDVHVD | (SEQ. ID NO. 215) |
| 91 | VVVVVHVHVHVHVHVH | (SEQ. ID NO. 216) |
| 92 | VVVVVHVDVDVHVDVD | (SEQ. ID NO. 217) |
| 93 | VVVVVHVEVEVHVEVE | (SEQ. ID NO. 218) |
| 94 | LLLLLRLDLRLDLRLD | (SEQ. ID NO. 219) |
| 95 | LLLLLRLRLDLDLRLR | (SEQ. ID NO. 220) |
| 96 | LLLLLELKLELKLELK | (SEQ. ID NO. 221) |
| 97 | LLLLLELELKLKLELE | (SEQ. ID NO. 222) |
| 98 | LLLLLRLELRLELRLE | (SEQ. ID NO. 223) |
| 99 | LLLLLRLRLELELRLE | (SEQ. ID NO. 224) |
| 100 | LLLLLKLDLKLDLKLD | (SEQ. ID NO. 225) |
| 101 | LLLLLELHLELHLELH | (SEQ. ID NO. 226) |
| 102 | LLLLLELELHLHLELE | (SEQ. ID NO. 227) |
| 103 | LLLLLRLRLRLRLRLR | (SEQ. ID NO. 228) |
| 104 | LLLLLRLRLRLRLDLD | (SEQ. ID NO. 229) |
| 105 | LLLLLRLRLRLDLDLD | (SEQ. ID NO. 230) |
| 106 | LLLLLHLDLHLDLHLD | (SEQ. ID NO. 231) |
| 107 | LLLLLHLHLHLHLHLH | (SEQ. ID NO. 232) |
| 108 | LLLLLHLDLDLHLDLD | (SEQ. ID NO. 233) |
| 109 | LLLLLHLELELHLELE | (SEQ. ID NO. 234) |
| 110 | IIIIIRIDIRIDIRID | (SEQ. ID NO. 235) |
| 111 | IIIIIRIRIDIDIRIR | (SEQ. ID NO. 236) |
| 112 | IIIIIEIKIEIKIEIK | (SEQ. ID NO. 237) |
| 113 | IIIIIEIEIKIKIEIE | (SEQ. ID NO. 238) |
| 114 | IIIIIRIEIRIEIRIE | (SEQ. ID NO. 239) |
| 115 | IIIIIRIRIEIEIRIE | (SEQ. ID NO. 240) |
| 116 | IIIIIKIDIKIDIKID | (SEQ. ID NO. 241) |
| 117 | IIIIIEIHIEIHIEIH | (SEQ. ID NO. 242) |
| 118 | IIIIIEIEIHIHIEIE | (SEQ. ID NO. 243) |
| 119 | IIIIIRIRIRIRIRIR | (SEQ. ID NO. 244) |
| 120 | IIIIIRIRIRIRIDID | (SEQ. ID NO. 245) |
| 121 | IIIIIRIRIRIDIDID | (SEQ. ID NO. 246) |
| 122 | IIIIIHIDIHIDIHID | (SEQ. ID NO. 247) |
| 123 | IIIIIHIHIHIHIHIH | (SEQ. ID NO. 248) |
| 124 | IIIIIHIDIDIHIDID | (SEQ. ID NO. 249) |
| 125 | IIIIIHIEIEIHIEIE | (SEQ. ID NO. 250) |
| 126 | MMMMMRMDMRMDMRMD | (SEQ. ID NO. 251) |
| 127 | MMMMMRMRMDMDMRMR | (SEQ. ID NO. 252) |
| 128 | MMMMMEMKMEMKMEMK | (SEQ. ID NO. 253) |

TABLE 3-continued

Hydrophobic Tails

| No. | Sequence (N → C) | |
|---|---|---|
| 129 | MMMMMEMEMKMKMEME | (SEQ. ID NO. 254) |
| 130 | MMMMMRMEMRMEMRME | (SEQ. ID NO. 255) |
| 131 | MMMMMRMRMEMEMRME | (SEQ. ID NO. 256) |
| 132 | MMMMKMDMKMDMKMD | (SEQ. ID NO. 257) |
| 133 | MMMMMEMHMEMHMEMH | (SEQ. ID NO. 258) |
| 134 | MMMMMEMEMHMHMEME | (SEQ. ID NO. 259) |
| 135 | MMMMMRMRMRMRMRMR | (SEQ. ID NO. 260) |
| 136 | MMMMMRMRMRMRMDMD | (SEQ. ID NO. 261) |
| 137 | MMMMMRMRMRMDMDMD | (SEQ. ID NO. 262) |
| 138 | MMMMMHMDMHMDMHMD | (SEQ. ID NO. 263) |
| 139 | MMMMMHMHMHMHMHMH | (SEQ. ID NO. 264) |
| 140 | MMMMMHMDMDMHMDMD | (SEQ. ID NO. 265) |
| 141 | MMMMMHMEMEMHMEME | (SEQ. ID NO. 266) |
| 142 | FFFFFRFDFRFDFRFD | (SEQ. ID NO. 267) |
| 143 | FFFFFRFRFDFDFRFR | (SEQ. ID NO. 268) |
| 144 | FFFFFEFKFEFKFEFK | (SEQ. ID NO. 269) |
| 145 | FFFFFEFEFKFKFEFE | (SEQ. ID NO. 270) |
| 146 | FFFFFRFEFRFEFRFE | (SEQ. ID NO. 271) |
| 147 | FFFFFRFRFEFEFRFE | (SEQ. ID NO. 272) |
| 148 | FFFFFKFDFKFDFKFD | (SEQ. ID NO. 273) |
| 149 | FFFFFEFHFEFHFEFH | (SEQ. ID NO. 274) |
| 150 | FFFFFEFEFHFHFEFE | (SEQ. ID NO. 275) |
| 151 | FFFFFRFRFRFRFRFR | (SEQ. ID NO. 276) |
| 152 | FFFFFRFRFRFRFDFD | (SEQ. ID NO. 277) |
| 153 | FFFFFRFRFRFDFDFD | (SEQ. ID NO. 278) |
| 154 | FFFFFHFDFHFDFHFD | (SEQ. ID NO. 279) |
| 155 | FFFFFHFHFHFHFHFH | (SEQ. ID NO. 280) |
| 156 | FFFFFHFDFDFHFDFD | (SEQ. ID NO. 281) |
| 157 | FFFFFHFEFEFHFEFE | (SEQ. ID NO. 282) |
| 158 | WWWWWRWDWRWDWRWD | (SEQ. ID NO. 283) |
| 159 | WWWWWRWRWDWDWRWR | (SEQ. ID NO. 284) |
| 160 | WWWWWEWKWEWKWEWK | (SEQ. ID NO. 285) |
| 161 | WWWWWEWEWKWKWEWE | (SEQ. ID NO. 286) |
| 162 | WWWWWRWEWRWEWRWE | (SEQ. ID NO. 287) |
| 163 | WWWWWRWRWEWEWRWE | (SEQ. ID NO. 288) |
| 164 | WWWWWKWDWKWDWKWD | (SEQ. ID NO. 289) |
| 165 | WWWWWEWHWEWHWEWH | (SEQ. ID NO. 290) |
| 166 | WWWWWEWEWHWHWEWE | (SEQ. ID NO. 291) |
| 167 | WWWWWRWRWRWRWRWR | (SEQ. ID NO. 292) |
| 168 | WWWWWRWRWRWRWDWD | (SEQ. ID NO. 293) |
| 169 | WWWWWRWRWRWDWDWD | (SEQ. ID NO. 294) |
| 170 | WWWWWHWDWHWDWHWD | (SEQ. ID NO. 295) |
| 171 | WWWWWHWHWHWHWHWH | (SEQ. ID NO. 296) |
| 172 | WWWWWHWDWDWHWDWD | (SEQ. ID NO. 297) |
| 173 | WWWWWHWEWEWHWEWE | (SEQ. ID NO. 298) |
| 174 | PPPPPRPDPRPDPRPD | (SEQ. ID NO. 299) |
| 175 | PPPPPRPRPDPDPRPR | (SEQ. ID NO. 300) |
| 176 | PPPPPEPKPEPKPEPK | (SEQ. ID NO. 301) |
| 177 | PPPPPEPEPKPKPEPE | (SEQ. ID NO. 302) |
| 178 | PPPPPRPEPRPEPRPE | (SEQ. ID NO. 303) |
| 179 | PPPPPRPRPEPEPRPE | (SEQ. ID NO. 304) |
| 180 | PPPPPKPDPKPDPKPD | (SEQ. ID NO. 305) |
| 181 | PPPPPEPHPEPHPEPH | (SEQ. ID NO. 306) |
| 182 | PPPPPEPEPHPHPEPE | (SEQ. ID NO. 307) |
| 183 | PPPPPRPRPRPRPRPR | (SEQ. ID NO. 308) |
| 184 | PPPPPRPRPRPRPDPD | (SEQ. ID NO. 309) |
| 185 | PPPPPRPRPRPDPDPD | (SEQ. ID NO. 310) |
| 186 | PPPPPHPDPHPDPHPD | (SEQ. ID NO. 311) |
| 187 | PPPPPHPHPHPHPHPH | (SEQ. ID NO. 312) |
| 188 | PPPPPHPDPDPHPDPD | (SEQ. ID NO. 313) |
| 189 | PPPPPHPEPEPHPEPE | (SEQ. ID NO. 314) |
| 190 | SSSSSRSDSRSDSRSD | (SEQ. ID NO. 315) |
| 191 | SSSSSRSRSDSDSRSR | (SEQ. ID NO. 316) |
| 192 | SSSSSESKSESKSESK | (SEQ. ID NO. 317) |
| 193 | SSSSSESESKSKSESE | (SEQ. ID NO. 318) |
| 194 | SSSSSRSESRSESRSE | (SEQ. ID NO. 319) |
| 195 | SSSSSRSRSESESRSE | (SEQ. ID NO. 320) |
| 196 | SSSSSKSDSKSDSKSD | (SEQ. ID NO. 321) |
| 197 | SSSSSESHSESHSESH | (SEQ. ID NO. 322) |
| 198 | SSSSSESESHSHSESE | (SEQ. ID NO. 323) |
| 199 | SSSSSRSRSRSRSRSR | (SEQ. ID NO. 324) |
| 200 | SSSSSRSRSRSRSDSD | (SEQ. ID NO. 325) |
| 201 | SSSSSRSRSRSDSDSD | (SEQ. ID NO. 326) |
| 202 | SSSSSHSDSHSDSHSD | (SEQ. ID NO. 327) |
| 203 | SSSSSHSHSHSHSHSH | (SEQ. ID NO. 328) |
| 204 | SSSSSHSDSDSHSDSD | (SEQ. ID NO. 329) |

TABLE 3-continued

Hydrophobic Tails

| No. | Sequence (N → C) | |
|---|---|---|
| 205 | SSSSSHSESESHSESE | (SEQ. ID NO. 330) |
| 206 | TTTTTRTDTRTDTRTD | (SEQ. ID NO. 331) |
| 207 | TTTTTRTRTDTDTRTR | (SEQ. ID NO. 332) |
| 208 | TTTTTETKTETKTETK | (SEQ. ID NO. 333) |
| 209 | TTTTTETETKTKTETE | (SEQ. ID NO. 334) |
| 210 | TTTTTRTETRTETRTE | (SEQ. ID NO. 335) |
| 211 | TTTTTRTRTETRTETRTE | (SEQ. ID NO. 336) |
| 212 | TTTTTKTDTKTDKTD | (SEQ. ID NO. 337) |
| 213 | TTTTTETHTETHTETH | (SEQ. ID NO. 338) |
| 214 | TTTTTETETHTHTETE | (SEQ. ID NO. 339) |
| 215 | TTTTTRTRTRTRTRTR | (SEQ. ID NO. 340) |
| 216 | TTTTTRTRTRTRTDTD | (SEQ. ID NO. 341) |
| 217 | TTTTTRTRTRTDTDTD | (SEQ. ID NO. 342) |
| 218 | TTTTTHTDTHTDTHTD | (SEQ. ID NO. 343) |
| 219 | TTTTTHTHTHTHTHTH | (SEQ. ID NO. 344) |
| 220 | TTTTTHTDTDTHTDTD | (SEQ. ID NO. 345) |
| 221 | TTTTTHTETETHTETE | (SEQ. ID NO. 346) |
| 222 | CCCCCRCDCRCDCRCD | (SEQ. ID NO. 347) |
| 223 | CCCCCRCRCDCDCRCR | (SEQ. ID NO. 348) |
| 224 | CCCCCECKCECKCECK | (SEQ. ID NO. 349) |
| 225 | CCCCCECECKCKCECE | (SEQ. ID NO. 350) |
| 226 | CCCCCRCECRCECRCE | (SEQ. ID NO. 351) |
| 227 | CCCCCRCECECRCE | (SEQ. ID NO. 352) |
| 228 | CCCCCKCDCKCDCKCD | (SEQ. ID NO. 353) |
| 229 | CCCCCECHCECHCECH | (SEQ. ID NO. 354) |
| 230 | CCCCCECECHCHCECE | (SEQ. ID NO. 355) |
| 231 | CCCCCRCRCRCRCRCR | (SEQ. ID NO. 356) |
| 232 | CCCCCRCRCRCRCDCD | (SEQ. ID NO. 357) |
| 233 | CCCCCRCRCRCDCDCD | (SEQ. ID NO. 358) |
| 234 | CCCCCHCDCHCDCHCD | (SEQ. ID NO. 359) |
| 235 | CCCCCHCHCHCHCHCH | (SEQ. ID NO. 360) |
| 236 | CCCCCHCDCDCHCDCD | (SEQ. ID NO. 361) |
| 237 | CCCCCHCECECHCECE | (SEQ. NO. ID 362) |
| 238 | YYYYYRYDYRYDYRYD | (SEQ. ID NO. 363) |
| 239 | YYYYYRYRYDYDYRYR | (SEQ. ID NO. 364) |
| 240 | YYYYYEYKYEYKYEYK | (SEQ. ID NO. 365) |
| 241 | YYYYYEYEYKYKYEYE | (SEQ. ID NO. 366) |
| 242 | YYYYYRYEYRYEYRYE | (SEQ. ID NO. 367) |
| 243 | YYYYYRYRYEYEYRYE | (SEQ. ID NO. 368) |
| 244 | YYYYYKYDYKYDYKYD | (SEQ. ID NO. 125) |
| 245 | YYYYYEYHYEYHYEYH | (SEQ. ID NO. 369) |
| 246 | YYYYYEYEYHYHYEYE | (SEQ. ID NO. 370) |
| 247 | YYYYYRYRYRYRYRYR | (SEQ. ID NO. 371) |
| 248 | YYYYYRYRYRYRYDYD | (SEQ. ID NO. 372) |
| 249 | YYYYYRYRYRYDYDYD | (SEQ. NO. ID 373) |
| 250 | YYYYYHYDYHYDYHYD | (SEQ. ID NO. 374) |
| 251 | YYYYYHYHYHYHYHYH | (SEQ. ID NO. 375) |
| 252 | YYYYYHYDYDYHYDYD | (SEQ. ID NO. 376) |
| 253 | YYYYYHYEYEYHYEYE | (SEQ. ID NO. 377) |
| 254 | NNNNNRNDNRNDNRND | (SEQ. ID NO. 378) |
| 255 | NNNNNRNRNDNDNRNR | (SEQ. ID NO. 378) |
| 256 | NNNNNENKNENKNENK | (SEQ. ID NO. 380) |
| 257 | NNNNNENENKNKNENE | (SEQ. ID NO. 381) |
| 258 | NNNNNRNENRNENRNE | (SEQ. ID NO. 382) |
| 259 | NNNNNRNRNENENRNE | (SEQ. ID NO. 383) |
| 260 | NNNNNKNDNKNDNKND | (SEQ. ID NO. 384) |
| 261 | NNNNNENHNENHNENH | (SEQ. ID NO. 385) |
| 262 | NNNNNENENHNHNENE | (SEQ. ID NO. 386) |
| 263 | NNNNNRNRNRNRNRNR | (SEQ. ID NO. 387) |
| 264 | NNNNNRNRNRNRNDND | (SEQ. ID NO. 388) |
| 265 | NNNNNRNRNRNDNDND | (SEQ. ID NO. 389) |
| 266 | NNNNNHNDNHNDNHND | (SEQ. ID NO. 390) |
| 267 | NNNNNHNHNHNHNHNH | (SEQ. ID NO. 391) |
| 268 | NNNNNHNDNDNHNDND | (SEQ. ID NO. 392) |
| 269 | NNNNNHNENENHNENE | (SEQ. ID NO. 393) |
| 270 | QQQQQRQDQRQDQRQD | (SEQ. ID NO. 394) |
| 271 | QQQQQRQRQDQDQRQR | (SEQ. ID NO. 395) |
| 272 | QQQQQEQKQEQKQEQK | (SEQ. ID NO. 396) |
| 273 | QQQQQEQEQKQKQEQE | (SEQ. ID NO. 397) |
| 274 | QQQQQRQEQRQEQRQE | (SEQ. ID NO. 398) |
| 275 | QQQQQRQRQEQEQRQE | (SEQ. ID NO. 399) |
| 276 | QQQQQKQDQKQDQKQD | (SEQ. ID NO. 400) |
| 277 | QQQQQEQHQEQHQEQH | (SEQ. ID NO. 401) |
| 278 | QQQQQEQEQHQHQEQE | (SEQ. ID NO. 402) |
| 279 | QQQQQRQRQRQRQRQR | (SEQ. ID NO. 403) |
| 280 | QQQQQRQRQRQRQDQD | (SEQ. ID NO. 404) |

TABLE 3-continued

Hydrophobic Tails

| No. | Sequence (N → C) | |
|---|---|---|
| 281 | QQQQQRQRQRQDQDQD | (SEQ. ID NO. 405) |
| 282 | QQQQQHQDQHQDQHQD | (SEQ. ID NO. 406) |
| 283 | QQQQQHQHQHQHQHQH | (SEQ. ID NO. 407) |
| 284 | QQQQQHQDQDQHQDQD | (SEQ. ID NO. 408) |
| 285 | QQQQQHQEQEQHQEQE | (SEQ. ID NO. 409) |

D. Formation of Self-assembling Materials

The peptides used to form the mesh can be assembled prior to application of the patch or can be assembled at the time of application either by contacting the mesh with an ionic solution or allowing the mesh to contact a bodily fluid.

Self-assembly may be initiated or enhanced at any subsequent time by the addition of an ionic solute or diluent to a solution of the material or by a change in pH. For example, NaCl at a concentration of between approximately 5 mM and 5 M can induce the assembly of macroscopic structures within a short period of time (e.g., within a few minutes). Lower concentrations of NaCl may also induce assembly but at a slower rate. Alternatively, self-assembly may be initiated or enhanced by introducing the materials (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure) comprising such ions. The gel does not have to be pre-formed prior to application to the desired site. Generally, self-assembly is expected to occur upon contacting the materials with such a solution in any manner.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$. The concentration of such ions required to induce or enhance self-assembly is typically at least 5 mM (e.g., at least 10, 20, or 50 mM). Lower concentrations also facilitate assembly, although at a reduced rate. When desired, self-assembling materials can be delivered with a hydrophobic material (e.g. a pharmaceutically-acceptable oil) in a concentration that permits self-assembly, but at a reduced rate. When self-assembling materials are mixed with a hydrophobic agent such as an oil or lipid the assembly of the material forms different structures. The structures will appear like ice on a layer of oil. In some cases when another material is added, the material will assemble into various other three dimensional structures that may be suitable for loading of a therapeutic agent. The hydrophilic part of the molecule will assemble in such a way as to minimize hydrophobic-hydrophilic interaction, thereby creating a barrier between the two environments. Several experiments have shown that the self-assembling materials will align on the surface of the oil like ice on water with the hydrophobic part of the molecule toward the surface and the hydrophilic portion of the molecule facing away from the oil, or will form toroidal-like structures with the hydrophobic material contained inside. This type of behavior enables the encapsulation of therapeutics or other molecules of interested for delivery in the body.

In another embodiment, the composition may contain a salt scavenger to drive assembly to a preferred configuration. For example, circular dichroism ("CD") experiments indicate that the assembly dynamics can be controlled using salt scavengers or salt enhancement to increase the formation of β-sheets, α-helices, or more random configurations. The compositions may optionally contain an indicator showing the configuration of the assembly (e.g., α-helix, β-sheet, lattice, etc.).

Alternatively, some of the materials described herein do not require ions to self-assemble but may self-assemble due to interactions with solvent, hydrophobic interactions, side chain interactions, hydrogen bonding, and the like.

The materials can be formed within regularly or irregularly-shaped molds, which may include a body cavity or a portion of the body (e.g., the lumen of a blood vessel) or which may be an inert material such as plastic or glass. The structures or scaffolds can be made to conform to a predetermined shape or to have a predetermined volume. To form a structure with a predetermined shape or volume (e.g., a desired geometry or dimension, including thin sheets or films), an aqueous solution of the material is placed in a pre-shaped casting mold, and the materials are induced to self-assemble by the addition of a plurality of ions. Alternately, the ions may be added to the solution shortly before placing the solution into the mold, provided that care is taken to place the solution into the mold before substantial assembly occurs. Where the mold is a tissue (e.g., the lumen of a blood vessel or other compartment, whether in situ or not), the addition of an ionic solution may not be necessary. The resulting material characteristics, the time required for assembly, and the dimensions of the macroscopic structure that forms are governed by the concentration and amount of solution that is applied, the concentration of ions used to induce assembly of the structure, and the dimensions of the casting apparatus. The scaffold can achieve a gel-like or substantially solid form at room temperature, and heat may be applied to facilitate the molding (e.g., one can heat a solution used in the molding process (e.g., a precursor-containing solution) to a temperature ranging up to about body temperature (approximately 37° C.)). Once the scaffold has reached the desired degree of firmness, it can be removed from the mold and used for a purpose described herein. Alternatively, the materials described herein may be used to anchor host tissue to a tissue matrix or scaffold. For example, the materials described herein can be used as a "glue" to anchor host tissue that is to be regenerated to a tissue matrix or scaffold to ensure that the matrix or scaffold stays in place in the local environment to which it is injected or implanted. Tissue matrices and scaffolds are well known in the art and can be prepared from synthetic, semi-synthetic, and/or natural materials.

Materials that assemble and/or undergo a phase transition (e.g., a transition from a liquid state to a semi-solid, gel, etc.) when they come in contact with the body or an ionic solution are useful in preventing the movement of bodily substances. Self-assembly or phase transition is triggered by components found in a subject's body (e.g., ions) or by physiological pH and is assisted by physiological temperatures. Self-assembly or phase transition can begin when the compositions are exposed to or brought into contact with a subject's body and may be facilitated by the local application of heat to the area where the composition has been (or will be) deposited. Based on studies to date, self-assembly occurs rapidly upon contact with internal bodily tissues without the application of additional heat. The time required for effective assembly and/or phase transition can occur in 60 seconds or less following contact with a subject's internal tissues or to conditions similar to those found within the body (e.g., in 50, 40, 30, 20, or 10 seconds or less). In some circumstances, such as where the concentration of self-assembling agents in the composition is low or where the movement of the bodily substance is substantial, self-assembly or phase transition may take longer to achieve the desired effect, for example, up to a minute, 5 minutes, 10 minutes, 30 minutes, an hour, or longer. For example, a solution containing a self-assembling peptide applied to sites of blood vessel transection in the brain, liver, or muscle provided complete hemostasis within times as short as 10 seconds following application. Ion-containing solutions may be preferred when the compositions are used to protect a subject from contamination, as phase transitions do not occur, or do not readily occur, when non-ionic solutions contact intact skin.

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance in a subject in need thereof. Self-assembly can be achieved in vitro, in vivo, or ex vivo, by exposure to conditions within a certain range of physiological values (e.g., conditions appropriate for cell or tissue culture), or by exposure to non-physiological conditions. "Non-physiological conditions" refers to conditions within the body or at a particular site that deviate from normal physiological conditions at that site. Such conditions may result from trauma, surgery, injury, infection, or a disease, disorder, or condition. For example, a puncture wound in the stomach generally results in a decrease in the pH as stomach acid flows into the wound site. The materials described herein should self-assemble under such conditions. While liquid formulations are readily dispensed, the compositions administered may also be in a gel form that may become stiffer upon contact with the subject's body.

Regardless of the precise nature of the self-assembling materials, upon exposure to conditions such as those described herein, the materials can form membranous two- or three-dimensional structures including a stable macroscopic porous matrix having ordered or non-ordered interwoven nanofibers (e.g., fibers approximately 5-20 nm in diameter, with a pore size of about 50-100 nm in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling materials can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling materials therein. Alternatively, it may be desirable for different parts of the material to have different mechanical properties. For example, it may be advantageous to decrease the stability of all or part of the material by manipulating the amino acid sequence. This may be desirable when the materials are used to fill a void, such that the edges of the material self-assemble to attach to the tissue site while the rest of the material flows out into the void. The sequences, characteristics, and properties of the materials and the structures formed by them upon self-assembly are discussed further below.

E. Therapeutic, Prophylactic and Diagnostic Agents

The meshes may also include other therapeutic, prophylactic or diagnostic agents. In a preferred embodiment, these may be anti-inflammatory agents, vasoactive agents, anti-infective agents, anesthetics, growth factors, vitamins, nutrients, and/or cells.

These can be peptides or proteins, polysaccharides or saccharides, nucleic acids nucleotides, proteoglycan, lipid, carbohydrate, or a small molecule, typically an organic compound, having multiple carbon-carbon bonds that may be isolated from nature or prepared via chemical synthesis. Small molecules have relatively low molecular weights (e.g., less than about 1500 g/mol) and are not peptides or nucleic acids. The substance can also be a biomolecule, which is a molecule such as a peptide, proteoglycan, lipid, carbohydrate, or nucleic acid having characteristics typical of molecules found in living organisms. Like small molecules, biomolecules can be naturally occurring or may be artificial (i.e., they may be molecules that have not been found in nature). For example, a protein having a sequence that has not been found in nature (e.g., one that does not occur in a publicly available database of sequences) or that has a known sequence modified in an unnatural way by a human hand (e.g., a sequence modified by altering a post-translational process such as glycosylation) is an artificial biomolecule. Nucleic acid molecules encoding such proteins (e.g., an oligonucleotide, optionally contained within an expression vector) are also biomolecules and can be incorporated into the compositions described herein. For example, a composition can include a plurality of self-assembling materials and cells that express, or that are engineered to express, a protein biomolecule (by virtue of containing a nucleic acid sequence that encodes the protein biomolecule).

Many different therapeutic, prophylactic or diagnostic agents can be incorporated into the formulation. Representative vasoconstrictors include epinephrine and phenylephrine; representative coloring agents include arsenazo III, chlorophosphonazo III, antipyrylazo 111, murexide, Eriochrome Black T, Eriochrome Blue SE, oxyacetazo I, carboxyazo III, tropolone, methylthymol blue, and Mordant Black 32; representative anesthetic agents include benzocaine, bupivacaine, butamben picrate, chloroprocaine, cocaine, curare, dibucaine, dyclonine, etidocaine, lidocaine, mepivacaine, pramoxine, prilocaine, procaine, propoxycaine, ropivacaine, tetracaine, or combinations thereof. Local application of the anesthetic agent may be all that is required in some situations, for example, for a burn or other wound to the skin, including decubitus ulcers; wounds, such as cancer sores; or for minimally invasive surgeries. Combining local anesthetics with the self-assembling materials, whether combined by virtue of being present in the same composition or by virtue of co-administration, can help contain the anesthetic within the body and reduce the amount entering the circulation.

Vasoconstrictors such as phenylephrine can be included to prolong the effect of local anesthesia (e.g., 0.1-0.5% phenylephrine). Analgesic agents other than a local anesthetic agent, such as steroids, non-steroidal anti-inflammatory agents like indomethacin, platelet activating factor (PAF) inhibitors such as lexipafant, CV 3988, and/or PAF receptor inhibitors such as SRI 63-441.

An anti-infective or antimicrobial agent (e.g., an antibiotic, antibacterial, antiviral, or antifungal agent) can be included for either systemic or local administration. Examples include β-lactam antibiotics such as penicillins and cephalosporins; other inhibitors of cell wall synthesis such as vancomycin; chloramphenicol; tetracyclines; macrolides; clindamyin; streptogramins; aminoglycosides; spectinomycin; sulfonamides; trimethoprim; quinolones; amphotericin B; flucytosine; azoles such as ketoconazole, itraconazole, fluconazole, clotrimazole, and miconazole; griseofulvin; terbinafine; and nystatin. The antimicrobial can be topically administered (e.g., to treat skin infections or burns) or to help prevent infection at a site of catheter insertion (e.g., an intravenous catheter). Suitable topical antimicrobials include kanamycin, neomycin, bacitracin, polymixin, topical sulfonamides such as mafenide acetate or silver sulfadiazine, and gentamicin sulfate. The antimicrobial can also be a broad-spectrum agent. For example, a second, third, or fourth generation cephalosporin can be used. These agents may be active against a wide range of bacteria including both gram positive and gram-negative species. Such antibacterial agents may be particularly appropriate where the present scaffolds are used to inhibit movement of intestinal contents such as during intestinal resection or other surgery that purposefully or accidentally disturbs the integrity of the intestinal wall. One of ordinary skill in the art will be able to select appropriate antimicrobial agents by considering factors such as the patient's history (e.g., any history of an allergic reaction to such agents), the location to which the peptides are to be applied, and the type of infectious agent likely to be present. Compositions containing antimicrobial agents can prevent infections in a variety of ways including: (1) killing the infectious agent due to the activity of the antimicrobial agent; (2) preventing infection by assembly of the material to form a barrier which blocks infiltration of the infectious agent into the tissue by blocking the tissue specific sequence on the infectious agent from interacting with the tissue; (3) causing the infectious agent to change its orientation with respect to the tissue due to the charge of the self-assembling material and thus block infiltration of the infectious agent into the tissue; (4) encapsulating the infectious agent within the self-assembling material to prevent infiltration of the infectious agent; and combinations thereof. The materials can also be used to prevent contamination or infection by other biologics and/or hazardous materials.

Any of the compositions described herein can include a coloring agent. Suitable coloring agents include commercially available food colorings, natural and synthetic dyes, and fluorescent molecules. Preferably, the coloring agent is nontoxic or is included at such low concentrations as to minimize any toxic effect. The use of a coloring agent allows for improved visualization of an area that is covered by a structure or scaffold and can facilitate removal, if such removal is desired. The coloring agent can be one that changes color when it comes into contact with a contaminated area (e.g., a color change may be triggered by the contamination itself (e.g., by the blood or bacteria present at a wound site)). For example, a metabolic product of a bacterium may trigger a color change. Conditions such as pH or redox state induced by contaminants may also be detected. Exemplary indicators include arsenzazo III, chlorophosphonazo III, antipyrylazo III, murexide, Eriochrome Black T and Eriochrome Blue SE for $Mg^{2+}$, oxyacetazo I, carboxyazo III, tropolone, methylthymol blue, and Mordant Black 32. AlamarBlue, a redox indicator, and phenol red are also of use in the compositions and methods. In another embodiment, the coloring agent may be in the form of a nanoparticle which reflects one wavelength of light and upon aggregation (i.e., self-assembly of the peptide) reflects a different wavelength of light.

Many other active agents can be included in the compositions. For example, a number of growth factors can be included to accelerate one or more aspects of healing (e.g., angiogenesis, cell migration, process extension, and cell proliferation). These types of compositions can be "included" as others can, by virtue of inclusion in the compositions or by virtue of co-administration in the present methods. Examples include vascular endothelial growth factor (VEGF), a transforming growth factor (TGF) such as transforming growth factor p, a platelet derived growth factor (PDGF), an epidermal growth factor (EGF), a nerve growth factor (NGF), an insulin-like growth factor (e.g., insulin-like growth factor I), a glial growth factor (GGF), a fibroblast growth factor (FGF), etc. It will be appreciated that in many cases these terms refer to a variety of different molecular species. For example, several transforming growth factor R species are known in the art. One of ordinary skill in the art will be guided in the selection of an appropriate growth factor by considering, for example, the site at which the composition is to be administered. For example, an EGF can be included in compositions applied to the skin; an NGF and/or GGF can be included in compositions applied to nerves or the nervous system; and so forth.

The growth factor or another agent can be a chemotactic substance, which has the ability, in vivo or in cell culture, to recruit cells to a site at which the substance is present. The cells recruited may have the potential to contribute to the formation of new tissue or to repair existing, damaged tissue (e.g., by contributing structurally and/or functionally to the tissue (e.g., by providing growth factors or contributing to a desirable immune response)). Certain chemotactic substances can also function as proliferation agents (e.g., neurotropic factors such as NGF or BDNF).

The compositions can also be used in combination with or instead of compounds such as cyanoacrylates, oxidized cellulose, fibrin sealants, collagen gel, thrombin powder, microporous polysaccharide powders, clotting factors (e.g., Factor V, Factor VIII, fibrinogen, or prothrombin) and zeolite powders.

In one embodiment, vitamins may be added to the material such as vitamin K after liver surgery. In addition, other vitamins can be added to facilitate the reconstruction of tissue or skin when applied topically in combination with the material. This could be after injury or in the normal course of topical hydration.

The one or more therapeutic, diagnostic and/or prophylactic agents can be administered simultaneously with the self-assembling materials in the same formulation, administered simultaneously in separate formulations, or sequentially. Alternatively, the active agent(s) can be covalently coupled to the self-assembling material.

It will be understood that therapeutic molecules are generally administered in an effective amount in order to achieve a clinically significant result, and effective dosages and concentrations are known in the art. These dosages and concentrations can guide the selection of dosages and concentrations in the present context. Bioactive molecules can be provided at a variety of suitable concentrations and in suitable amounts (e.g., in the microgram or milligram range, or greater). For guidance, one can consult texts such as Goodman and Gilman's *The Pharmacological Basis of Therapeutics*, 10th Ed., and Katzung, *Basic and Clinical Pharmacology*.

Cells

Where cells are delivered to a patient (e.g., to promote tissue healing), autologous cells can be used. In one embodiment, the cells could be hematopoietic cells from the patient, dispersed in the material and implanted. In another embodiment, the cells can be cord red blood cells.

The meshes may include one or more additional substances such as bioactive molecules or cells. In some instances, the cell may secrete the bioactive molecule either naturally or following genetic engineering (e.g., to express and/or secrete a recombinant protein). The structures described herein are able to support cell attachment, viability, and growth; these have been observed when cells are cultured on the surface of the material or when cells grow within the material (e.g., when encapsulated). In addition, the structures are able to serve as substrates for neurite growth and synapse formation when neurons are grown on or within them. Thus, bioactive molecules and cells can be encapsulated within the peptide structures and maintain substantial function and viability when so encapsulated (see, e.g., U.S. Ser. No. 09/778,200 and U.S. Ser. No. 10/196,942).

F. Other Constituents

The disclosed meshes can include additional organic and/or inorganic materials. In some embodiments the additional materials can provide structural support to the mesh, such as materials that provide a scaffold. Scaffold materials can be selected to provide physical strength, elasticity, porosity, solubility, volume and bulk, as required by the application. In certain embodiments, the scaffold material has mechanical and/or biological properties similar to the extracellular matrix (ECM).

Scaffold materials can include polymers, including natural polymers such as polypeptides and proteins. The natural polymers create a scaffold onto which self-assembling peptides, therapeutic agents, cells or other agents are attached or associated. In some embodiments the disclosed surgical meshes include proteins, such as ECM proteins. Exemplary natural scaffold materials for use in the disclosed meshes include alginate; fibrinogen; hyaluronic acid; starch; chitosan; silk; gelatin; dextran; elastin; collagen; and combinations thereof.

In some embodiments meshes include scaffold materials that are synthetic polymers. Exemplary synthetic polymers include poly(L-lactic acid co-ε-caprolactone) (PLCL); poly (DL-lactic acid) (PDLA); poly(lactic-co-glycolicacid) (PLGA); poly(ethylene oxide) (PEO); poly(vinyl alcohol) (PVA); poly (methyl methacrylate) (PMMA); poly(ethylene-co-vinyl acetate) (PEVA); polystyrene; polyurethane; poly (L-lactic acid) (PLLA); polylactic acid (PLA) and mixtures thereof.

In preferred embodiments the scaffold materials are biocompatible. In preferred embodiments the scaffold materials do not induce an immune response.

III. Methods of Making Meshes

The meshes described herein can be prepared using any techniques known in the art. Meshes are typically loosely woven materials so any technique in the art suitable to prepare woven materials can be used. Meshes can also be non-woven. The meshes can be constructed to be a variety of shapes and sizes. Meshes can be from a several micrometers to several centimeters in thickness, and can be shaped according to the desired use.

Non-limiting examples of methods for manufacturing woven and non-woven meshes and scaffolds including a variety of natural and non-natural polymers are described in U.S. Pat. Nos. 8,568,637; 7,700,721; 8,039,258; 7,704,740; 5,762,846; 8,512,728; as well as Dhan, et al., *Nanomedicine: Nanotechnology, Biology, and Medicine*, 8, pp. 1242-1262 (2012); Nguyen and Lee, *Sci. Technol. Adv. Mater.*, 13, 035002 (11 pp) (2012); Ahmad, et al., *Carbohydrate Polymers*, V89 (1), pp. 222-229 (2012); and Brun, et al., *Acta Biomaterialia*, 7, pp. 2526-2532 (2011).

A. Formulations of Self-assembling Peptides

Self-assembling peptides for use in making the disclosed meshes can be a dry powder formulation that contains at least 75% weight/weight (w/w) self-assembling peptides, at least 80% w/w, at least 85% w/w, at least 90% w/w, at least 95% w/w, or more than 95% w/w self-assembling peptides.

In other embodiments self-assembling peptides for use in making the disclosed meshes can be formulated in a solution that contains from about 0.25% weight/volume (w/v), to at least 7.5% w/v self-assembling peptides, preferably from about 1% w/v, to about 3% w/v self-assembling peptides. In some embodiments at least 75%, at least 80%, at least 85%, at least 90%, at least 95%, or more than 95% of the self-assembling peptides have the same size and sequence.

The physical properties of the liquids (e.g., viscosity, surface tension and electrical conductivity) can be measured using any techniques and equipment known to those in the art, (e.g., viscometer; Kruss tensiometer; conductivity meter, etc.).

In some embodiments meshes are formed from peptides having the same sequence and length. In other embodiments, a mixture of self-assembling peptides having different sizes and sequences can be used. In certain embodiments the size and sequence of the peptides included within the mesh fibers can give rise to meshes having different structural and functional properties. For example, the strength and elasticity of the meshes can vary according to the length of the peptides used to create the mesh. In certain embodiments the relative proportions of the self-assembling peptides can be varied as desired by the application.

In certain embodiments the meshes contain peptides having different numbers of the same self-assembling units (e.g., RADA (SEQ ID NO 57) and RADARADARADARADA (SEQ ID NO. 1)). In other embodiments the meshes contain peptides having different self-assembling units and different sizes (e.g., RADA (SEQ ID NO 57) and EAKAEAKAEA-KAEAKA (SEQ ID NO. 410)).

In some embodiments a composite of self-assembling peptides having different sizes and different amino acid sequences can be used to provide meshes having specific structural and biological properties. In particular embodiments the self-assembling peptides include two or more repeating units of the sequence RADA, two or more repeating units of the sequence EAKA, or mixtures thereof.

Self-assembling peptides having tissue specific sequences can be included within meshes intended for use in the corresponding tissue type. Peptides having the same or a different sequence can be deposited on top of the first mesh layer, to form a three-dimensional mesh that fills the desired space, such as the volume of a wound or surgical site. In some embodiments meshes can be prepared according to the disclosed techniques using self-assembling peptides having the same modulus as the tissue type for which the mesh is intended to be applied or used.

Meshes prepared according to the disclosed materials and methods can be cross-linked, dried or frozen prior to use. The dried meshes can be stored for extended periods of time.

B. Electrospinning

In one embodiment, the meshes are prepared by electrospinning Electrospinning uses an electrical charge to draw very fine (typically on the micro or nano scale) fibres from a liquid.

The disclosed meshes can be produced by electrospinning of stock solutions containing one or more self-assembling materials. Stock solutions can contain self-assembling peptides in an aqueous solution, a non-aqueous solution or as a dry powder. Self-assembling peptides can be present in the stock solution at any concentration that is high enough to prevent vaporization.

Formulations of self-assembling peptides for electrospinning into fibrous meshes are disclosed. The formulations can be used as stock solutions. Stock solutions of self-assembling peptides for electrospinning can be dry powders or solutions, such as aqueous or non-aqueous solutions. Stock solutions can contain peptides having a single sequence, or one or more different sequences. In some embodiments two or more different stock solutions can be electrospun onto a support at the same time using multiple nozzles, or subsequently from the same or different nozzle.

Electrospinning stock solutions can optionally contain a mixture of materials for electrospinning into the mesh. In some embodiments self-assembling peptides are mixed with a solution of one or more other materials prior to electrospinning. For example, stock solutions can contain one or more self-assembling peptides and one or more scaffold materials, therapeutic or diagnostic reagents, or combinations thereof. When stock solutions containing more than one material are used, the ratio of self-assembling peptides to the other materials can be varied according to the needs of the application. For example, the self-assembling peptide may be present in solution at any ratio to the other materials.

In other embodiments the meshes are produced by electrospinning of stock solutions containing one or more scaffold materials, which are then covered or coated with self-assembling peptides. In certain embodiments the self-assembling peptide is coated onto the surface of an electrospun scaffold material. In some embodiments the self-assembling peptide is applied to the scaffold as a dry powder.

In some embodiments cells are deposited onto the fibers as they are electrospun. Cells can be deposited from a separate nozzle, so that cells are deposited onto fibers before the mesh is formed. In other embodiments cells are deposited onto the mesh after it has formed.

Electrostatic Spinning

Electrostatic spinning (electrospinning) shares characteristics of both electrospraying and conventional solution dry spinning of fibers. The process does not require the use of coagulation chemistry or high temperatures to produce solid threads from solution. This makes the process particularly suited to the production of fibers using large and complex molecules, such as self-assembling peptides. Electrospinning from molten precursors can also be performed. This method ensures that no solvent can be carried over into the final product.

When a sufficiently high voltage is applied to a liquid droplet, the body of the liquid becomes charged, and electrostatic repulsion counteracts the surface tension and the droplet is stretched; at a critical point a stream of liquid erupts from the surface. This point of eruption is known as the Taylor cone. If the molecular cohesion of the liquid is sufficiently high, stream breakup does not occur (if it does, droplets are electrosprayed) and a charged liquid jet is formed.

As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from this bending instability leads to the formation of uniform fibers with nanometer-scale diameters.

Modification of the spinneret and/or the type of solution can allow for the creation of fibers with unique structures and properties. Electrospun fibers can adopt a porous or core-shell morphology depending on the type of materials being spun as well as the evaporation rates and miscibility for the solvents involved. For techniques which involve multiple spinning fluids, the general criteria for the creation of fibers depends upon the spinnability of the outer solution. This opens up the possibility of creating composite fibers which can function as drug delivery systems or possess the ability to self-heal upon failure.

In some embodiments the collector moves relative to the spinneret during spinning Movement of the collector can be controlled to enable the formation of desired structures from the spinning process. In some embodiments the mesh is a loosely woven or non-woven mesh.

The size of an electrospun fiber of self-assembling peptides can be in the nano scale and the fibers may possess nano-scale surface texture, leading to different modes of interaction with other materials compared with macro-scale materials. In addition to this, the ultra-fine fibers of self-assembled peptides produced by electrospinning have a very high surface to volume ratio, and a relatively defect-free structure at the molecular level.

A high surface to volume ratio makes electrospun self-assembling peptide meshes suitable for activities requiring a high degree of physical contact, such as providing sites for chemical reactions, or the capture of small sized particulate material by physical entanglement-filtration. The second property should allow electrospun fibers to approach the theoretical maximum strength of the spun material, opening up the possibility of making high mechanical performance composite materials.

Coaxial Electrospinning

A coaxial setup uses a multiple solution feed system which allows for the injection of one solution into another at the tip of the spinneret. The sheath fluid is believed to act as a carrier which draws in the inner fluid at the Taylor Cone of the electrospinning jet. If the solutions are immiscible then a core shell structure is usually observed. Miscible solutions however can result in porosity or a fiber with distinct phases due to phase separation during solidification of the fiber.

Emulsion Electrospinning

Emulsions can be used to create core shell or composite fibers without modification of the spinneret. However, these fibers are usually more difficult to produce as compared to coaxial spinning due to the greater number of variables which must be accounted for in creating the emulsion. A water phase and an immiscible solvent phase are mixed in the presence of an emulsifying agent to form the emulsion. Any agent which stabilizes the interface between the immiscible phases can be used. Surfactants such as sodium dodecyl sulfate, Triton and nanoparticles have been used successfully. During the electrospinning process the emulsion droplets within the fluid are stretched and gradually confined leading to their coalescence. If the volume fraction of inner fluid is sufficiently high, a continuous inner core can be formed.

Electrospinning of blends is a variation of this technique which uses the fact that polymers are generally immiscible with each and can phase segregate without the use of surfactants. This method can be simplified further if a solvent which dissolves both polymers is used Melt Electrospinning Electrospinning of polymer melts eliminates the need for volatile solvents in solution electrospinning. The setup is very similar to that employed in conventional electrospinning and includes the use of a syringe or spinneret, a high voltage supply and the collector. The polymer melt is usually produced by heating from either resistance heating, circulating fluids, air heating or lasers. Due to the high viscosity of polymer melts, the fiber diameters are usually much larger than those obtained from solution electrospinning. The fiber uniformity upon achieving stable flow rates and thermal equilibrium, tends to be very good. The whipping instability which is the predominant stage in which the fiber is stretched for spinning from solutions is absent from the melt spinning process due to the low melt conductivity. From literature, the biggest factors which affect the fiber size tend to be the feed rate and the molecular weight of the polymer. Fiber sizes ranging from ~250 nm to several hundreds of micrometers have been created thus far with the lower sizes being achieved using low molecular weight polymers.

Direct Placement Electrospinning

In some embodiments electrospinning of meshes can occur immediately prior to, or at the time of application in vitro or in vivo. In certain embodiments the electrospun fibers are deposited into or onto the body of a subject directly from the dispensing spinneret. In a particular embodiment the dispensing may deposit a mesh directly into or onto diseased or damaged tissue, such as wounds or surgical sites.

In some embodiments the electrospinning apparatus is adapted to facilitate the direct placement of the electrospun fibers. In certain embodiments the electrospinning apparatus is a portable or hand-held apparatus. The use of a portable or hand-held apparatus can assist in the direct placement of the fibers to desired locations in vivo and in vitro.

In further embodiments, modification of the spinneret and/or the type of solution can allow for the direct placement of self-assembling fibers relative to one another. The parameters that control direct placement can include charge, hydrophobicity and pH. Direct placement of self-assembling peptides can enable the formation of meshes with desired structural and functional characteristics, such as different strength and modulus at distinct regions of the mesh.

Direct placement of electrospun fibers can enable the specific deposition of certain fibers to certain tissue types and/or certain locations within a tissue. In one embodiment a multi-layered structure is produced by the sequential deposition of different types of fiber onto or into the target location. In some embodiments the fibers within different layers include self-assembling peptides having distinct sequences, sizes and structures.

C. Other Methods of Making Meshes

Meshes of self-assembling peptides can be produced using one or more techniques known to those skilled in the art, including but not limited to microfluidic techniques; spinning techniques including dispersion spinning, wet spinning, tack spinning, force spinning using centrifugal force and gel spinning; templating onto a surface; injection molding of a formulation of self-assembling peptides; stamping of a dry powder formulation or a frozen formulation of self-assembling peptides; direct application of a slurry formulation containing self-assembling peptides onto a stencil, or patterned surface, such as a bandage or adhesive bandage; or assembly of a composite structure formed by a combination of these methods.

In some embodiments would a pre-formed polymer mesh is soaking in a solution of self-assembling polypeptides and then freeze dried to coat the polymer with the polypeptide.

In some embodiments peptides for use in the described methods are assembled prior to formation of the mesh. In other embodiments self-assembly occurs upon formation or after formation of the mesh. Variation of physical parameters, such as temperature and ionic strength of the solvent can be applied to induce assembly of peptides at desired times during the formation of the mesh structure.

D. Protective or Support Materials

The disclosed meshes can include one or more biological or non-biological materials that provide support and/or protection to the fibrous structure. In some embodiments the mesh includes a protective or support layer, such as an adhesive strip, a film, a micro-porous substrate or network, a sponge, etc. The protective or support layer can be in the form of a backing layer, such as an adhesive bandage or metallic film.

Exemplary protective or support materials include but are not limited to polyurethane, tin foil, poly(L-lactic acid co-$\epsilon$-caprolactone)(PLCL); poly(DL-lactic acid) (PDLA); poly(lactic-co-glycolic acid)(PLGA); poly(ethylene oxide) (PEO); poly(vinyl alcohol)(PVA); poly (methyl methacrylate)(PMMA); poly(ethylene-co-vinyl acetate) (PEVA); PPO block copolymer polystyrene; polyurethane; poly(L-lactic acid)(PLLA); polylactic acid (PLA) and mixtures thereof. The support material can be fully or partly biodegradable, or non-biodegradable.

In certain embodiments the mesh of self-assembling peptides is produced and deposited directly onto the protective or support layer.

IV. Methods of Using Meshes

The disclosed surgical meshes can be used as either a permanent or temporary support for organs and other tissues during surgery and/or to strength tissue. The meshes are available in both inorganic and biological materials, and are used in a variety of surgeries. Though hernia repair surgery is the most common application, they can also be used for reconstructive work; such as in pelvic organ (e.g., bladder, uterus, bowel or rectum) prolapse and chest wall reconstruction. Meshes can also be used to treat surgical or traumatic wounds. Permanent meshes remain in the body, whereas temporary ones dissolve over time; as an example, some meshes combine permanent and temporary meshes such as Vipro; a brand name for a product combining the re-absorbable material vipryl, made from polyglycolic acid, and prolene, a non-reabsorbable polypropylene. Prior to use, the meshes can be a woven or non-woven fibrous sheet, with high surface area to volume ratio.

The meshes described here can also be used to control the movement of bodily fluids, e.g., to prevent the movement of fluids, such as blood. In one embodiment, the mesh is a hemostatic mesh. In certain embodiments, the mesh is biodegradable. Meshes can biodegrade at a time following application that is consistent with the time required for healing and tissue regeneration. Meshes can biodegrade at a time that is one day, one week, one month or more than one month following application. In some embodiments the disclosed meshes degrade over a period of several weeks, for example 1, 2, 3, 5, 6, 7, 8 or more than 8 weeks following application. Meshes can degrade completely, or can be partly biodegradable, or completely non-biodegradable.

The peptides can be assembled at any time before application of the mesh or during application of the mesh. For example, the mesh can be manufactured and the finished mesh exposed to an ionic solution to induce gel formation. The gelled mesh can be stored until use. The gelled mesh can be dehydrated prior to storage. The mesh can be gelled in mold to form a particular shape. In other embodiments, the mesh is prepared and stored in unassembled form. The mesh can be dried prior to storage. Immediately prior to use, the mesh is exposed to an ionic solution to initiate assembly. Again, the mesh can be gelled in a mold to form a particular shape. In still other embodiments, the mesh is applied or implanted in an unassembled form and the peptides assemble upon contact with a bodily fluid. This can be useful if one wants the mesh to gel in the shape of the site of application, such as a void, vessel, lumen, etc.

The mesh can have associated with it one or more therapeutic, prophylactic, and/or diagnostic agents, as discussed above. The agent can be impregnated into the mesh and/or coated on the mesh. In other embodiments, the agent is covalently coupled to one or more of the materials that compose the mesh. In some embodiment, the mesh has associated therewith one or more hemostatic agents, growth factors, desiccants, vitamins, antimicrobial agents, analgesics, anti-inflammatory agents, or combinations thereof.

In other embodiments, the mesh contains a pH-adjusting agent which is released at the site of administration to alter the pH at the site of administration. For example, wounds to the skin typically heal more effectively at lower pH. Therefore, one or more agents which lower the pH at the site of application may shorten healing times and improve the efficacy of the mesh. In contrast, wounds (e.g., surgical, trauma, or otherwise (ulcers)) to the GI tract may benefit from a higher pH at the site of treatment to offset the more acidic environment of the GI tract. The pH at the site of application can be increased by incorporate a basic agent into the mesh.

The mesh can further contain backing or support layer that provides support and/or protection to the mesh. The backing layer may be biodegradable or non-biodegradable. The backing layer can be composed of any material which is biocompatible for those embodiments, wherein the backing layer is also applied/implanted. In other embodiments, the backing layer can be removed prior to application of the mesh. The backing layer can be adhesive or non-adhesive. For those embodiments where the backing layer is applied/implanted, the backing layer can have associated with it one or more therapeutic, prophylactic, and/or diagnostic agents as discussed above.

The meshes described herein can be used to treat a variety of disorders as discussed above. In some embodiments, the meshes described herein are used to treat patients with primary or secondary or acquired bleeding/coagulation/clotting disorders.

Exemplary coagulation disorders include vitamin K deficiency; Von Willebrand disease; hemophilia; congenital afibrinogenemia; Glanzmann's thrombasthenia; Bernard-Soulier syndrome; and thrombocytopenia. Exemplary patients having reduced coagulation include subjects having deficiency in one or more components of the coagulation cascade system (Factor V; Factor X; Factor XII; etc.), as well as patients receiving anti-coagulant therapy (e.g., aspirin; ardeparin; urokinase; warfarin; heparin; thrombin inhibitors; etc.) or other drugs that result in increased bleeding or decreased coagulation as compared to a normal control. The meshes can be packaged with one or more devices to facilitate application of the meshes to locations which are hard to reach (GI tract, lung, heart, etc.) or have complicated shapes/geometry (e.g., nose for epitaxis). Exemplary devices include cones and other devices that allow one to implant the mesh in a hard to reach location. Other devices include laproscopes, endoscopes, etc.

EXAMPLES

Example 1

Self-assembling Peptides Give Rise to Hemostasis

Materials and Methods

A self-assembling peptide having the sequence RADARA-DARADARADA (RADA4; SEQ. ID. NO: 1) acetate salt was reconstituted in sterile water to 3%. The material was stored at ambient temperature in a cooler with cold pack over it until brought to the study facility. Lyo cakes of 3 vials were crushed using a spatula and then combined in 1 vial. The combined content was reconstituted with 1 mL volume of sterile water for injection. The lyophilized formulation went in solution easily in 1-2 minutes and was vortexed for 30 seconds before use.

Four female Sprague Dawley rats each weighing 300-320 g were anesthetized with a mixture of xylaxine/ketamine. When a suitable plane of anesthesia was reached, a ventral midline incision was made in the abdomen allowing for visualization and manipulation of the liver's right lobe. Further manipulation to expose the portal vein was performed to allow for withdrawal of 1 mL of blood for measurement of blood activated clotting time (ACT).

A wooden spatula was then placed behind the right lobe of the liver and a 4 mm diameter biopsy punch was used to remove a full thickness 4 mm diameter section of the liver resulting in a lesion with brisk bleeding.

Immediately, 0.5 mL of a 3% aqueous solution of pre-formulated RADA4 peptide reconstituted in sterile water was applied to the biopsy site using a 22½ gauge needle.

Results

Bleeding was seen to slow upon application of the RADA4 peptide solution and stopped completely within 30 seconds. Later assessments at 10 minutes following RADA4 application showed that hemostasis was stable without further bleeding.

Example 2

Self-assembling Peptides Give Rise to Hemostasis in the Presence of Anti-coagulant Materials and Methods To determine whether hemostasis could be achieved in the presence of anticoagulant, heparin was then administered to the animal at a dose of 500 IU per kg body weight injected directly into the portal vein. Two minutes after heparin injection, a second 4 mm diameter biopsy punch lesion was made adjacent to the first lesion in the right lobe of the liver and 0.5 ml of a 3% aqueous RADA4 peptide solution was again added to the lesion.

Results

Bleeding was seen to slow and stop within 30 seconds of addition of the peptide, and this was stable at 10 minutes, as before. Baseline ACT measurements in these animals was approximately 110 seconds. An additional ACT measurement made 8 minutes following heparin injection (500 IU/kg) was greater than 1,300 seconds indicating significant heparin-induced anticoagulation in these animals.

The use of RADA4 peptide formulated as a 3% aqueous RADA4 peptide solution was successful in producing hemostasis in the rat liver biopsy punch model in both the absence and presence of clinically significant anticoagulation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A surgical mesh comprising self-assembling peptides, wherein the mesh comprises dehydrated or dried woven or non-woven fibers of the self-assembling peptides.

2. The surgical mesh of claim 1, wherein the self-assembling peptides have a sequence of amino acid residues conforming to one or more of Formulas I-IV:

$$((Xaa^{neu}\text{-}Xaa^{+})_x(Xaa^{neu}\text{-}Xaa^{-})_y)_n \quad (I);$$

$$((Xaa^{neu}\text{-}Xaa^{-})_x(Xaa^{neu}\text{-}Xaa^{+})_y)_n \quad (II);$$

$$((Xaa^{+}\text{-}Xaa^{neu})_x(Xaa^{-}\text{-}Xaa^{neu})_y)_n \quad (III);$$

$$((Xaa^{-}\text{-}Xaa^{neu})_x(Xaa^{+}\text{-}Xaa^{neu})_y)_n \quad (IV);$$

wherein $Xaa^{neu}$ represents an amino acid residue having a neutral charge under physiological conditions; $Xaa^{+}$ represents an amino acid residue having a positive charge under physiological conditions; $Xaa^{-}$ represents an amino acid residue having a negative charge under physiological conditions; x and y are integers having a value of 1, 2, 3, or 4, independently; and n is an integer having a value of 1-5.

3. The surgical mesh of claim 1, wherein all of the self-assembling peptides have the same amino acid sequence.

4. The mesh of claim 1, further comprising one or more non self-assembling materials.

5. The mesh of claim 4, wherein the mesh is partially or completely biodegradable.

6. The mesh of claim 4, wherein the mesh further comprises a backing material.

7. The mesh of claim 4, wherein the mesh further comprises one or more therapeutic, prophylactic, and/or diagnostic agents.

8. The mesh of claim 7, wherein the mesh comprises a hemostatic agent.

9. The mesh of claim 4 wherein the mesh comprises a desiccant.

10. The mesh of claim 4, further comprising a pH-adjusting agent.

11. The mesh of claim 1, wherein the mesh is prepared by a method selected from the group consisting of microfluidics; injection molding; stamping; templating onto a surface having a desired shape; electrospinning; freezing of a powder; freezing of a solution; coating of a solid substrate, and a combination thereof.

12. The mesh of claim 1, wherein the mesh is prepared by electrospinning a stock solution of the self-assembling peptides.

13. A method for controlling the movement of bodily fluids in a patient, the method comprising applying to or implanting in a patient the mesh of claim 1, wherein the self-assembling peptides assemble to form a barrier structure that inhibits or prevents the movement of bodily fluids through the mesh.

14. The method of claim 13, wherein the bodily fluid is blood.

15. The method of claim 13, wherein the patient suffers from a primary, secondary, or acquired bleeding/coagulation/clotting disorder.

16. The method of claim 13, wherein the self-assembling peptides are assembled immediately prior to, during or after application of the mesh.

17. The method of claim 12, wherein the stock solution contains a concentration of ions less than 5 mM.

18. The method of claim 13, wherein the mesh is hydrated prior to application.

* * * * *

SEQUENCE LISTING

```
<160> NUMBER OF SEQ ID NOS: 410

<210> SEQ ID NO 1
<211> LENGTH: 16
<212> TYPE: PRT
<213> ORGANISM: Artificial Sequence
<220> FEATURE:
<223> OTHER INFORMATION: Self-complementary peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 2

Ser Gly Ser Gly Ser Gly Ser Gly Ser Gly Ser Gly Ser Gly Ser Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 3

Ser Ala Ser Ala Ser Ala Ser Ala Ser Ala Ser Ala Ser Ala Ser Ala
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 4

Ser Val Ser Val Ser Val Ser Val Ser Val Ser Val Ser Val Ser Val
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 5
```

```
Ser Leu Ser Leu Ser Leu Ser Leu Ser Leu Ser Leu Ser Leu Ser Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 6

Ser Ile Ser Ile Ser Ile Ser Ile Ser Ile Ser Ile Ser Ile Ser Ile
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 7

Ser Met Ser Met Ser Met Ser Met Ser Met Ser Met Ser Met Ser Met
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 8

Ser Phe Ser Phe Ser Phe Ser Phe Ser Phe Ser Phe Ser Phe Ser Phe
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 9

Ser Trp Ser Trp Ser Trp Ser Trp Ser Trp Ser Trp Ser Trp Ser Trp
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 10

Ser Pro Ser Pro Ser Pro Ser Pro Ser Pro Ser Pro Ser Pro Ser Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 11
```

Thr Gly Thr Gly Thr Gly Thr Gly Thr Gly Thr Gly Thr Gly Thr Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 12

Thr Ala Thr Ala Thr Ala Thr Ala Thr Ala Thr Ala Thr Ala Thr Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 13

Thr Val Thr Val Thr Val Thr Val Thr Val Thr Val Thr Val Thr Val
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 14

Thr Leu Thr Leu Thr Leu Thr Leu Thr Leu Thr Leu Thr Leu Thr Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 15

Thr Ile Thr Ile Thr Ile Thr Ile Thr Ile Thr Ile Thr Ile Thr Ile
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 16

Thr Met Thr Met Thr Met Thr Met Thr Met Thr Met Thr Met Thr Met
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 17

Thr Phe Thr Phe Thr Phe Thr Phe Thr Phe Thr Phe Thr Phe Thr Phe

```
<210> SEQ ID NO 18
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 18

Thr Trp Thr Trp Thr Trp Thr Trp Thr Trp Thr Trp Thr Trp Thr Trp
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 19

Thr Pro Thr Pro Thr Pro Thr Pro Thr Pro Thr Pro Thr Pro Thr Pro
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 20

Cys Gly Cys Gly Cys Gly Cys Gly Cys Gly Cys Gly Cys Gly Cys Gly
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 21

Cys Ala Cys Ala Cys Ala Cys Ala Cys Ala Cys Ala Cys Ala Cys Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 22

Cys Val Cys Val Cys Val Cys Val Cys Val Cys Val Cys Val Cys Val
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 23

Cys Leu Cys Leu Cys Leu Cys Leu Cys Leu Cys Leu Cys Leu Cys Leu
1               5                   10                  15
```

<210> SEQ ID NO 24
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 24

Cys Ile Cys Ile Cys Ile Cys Ile Cys Ile Cys Ile Cys Ile Cys Ile
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 25

Cys Met Cys Met Cys Met Cys Met Cys Met Cys Met Cys Met Cys Met
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 26

Cys Phe Cys Phe Cys Phe Cys Phe Cys Phe Cys Phe Cys Phe Cys Phe
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Self-assembling peptide

<400> SEQUENCE: 27

Cys Trp Cys Trp Cys Trp Cys Trp Cys Trp Cys Trp Cys Trp Cys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 28

Cys Pro Cys Pro Cys Pro Cys Pro Cys Pro Cys Pro Cys Pro Cys Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 29

Tyr Gly Tyr Gly Tyr Gly Tyr Gly Tyr Gly Tyr Gly Tyr Gly Tyr Gly
1               5                   10                  15

```
<210> SEQ ID NO 30
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 30

Tyr Ala Tyr Ala Tyr Ala Tyr Ala Tyr Ala Tyr Ala Tyr Ala Tyr Ala
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 31

Tyr Val Tyr Val Tyr Val Tyr Val Tyr Val Tyr Val Tyr Val Tyr Val
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 32

Tyr Leu Tyr Leu Tyr Leu Tyr Leu Tyr Leu Tyr Leu Tyr Leu Tyr Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 33

Tyr Ile Tyr Ile Tyr Ile Tyr Ile Tyr Ile Tyr Ile Tyr Ile Tyr Ile
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 34

Tyr Met Tyr Met Tyr Met Tyr Met Tyr Met Tyr Met Tyr Met Tyr Met
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 35

Tyr Phe Tyr Phe Tyr Phe Tyr Phe Tyr Phe Tyr Phe Tyr Phe Tyr Phe
1               5                   10                  15
```

```
<210> SEQ ID NO 36
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 36

Tyr Trp Tyr Trp Tyr Trp Tyr Trp Tyr Trp Tyr Trp Tyr Trp Tyr Trp
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 37

Tyr Pro Tyr Pro Tyr Pro Tyr Pro Tyr Pro Tyr Pro Tyr Pro Tyr Pro
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 38

Asn Gly Asn Gly Asn Gly Asn Gly Asn Gly Asn Gly Asn Gly Asn Gly
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 39

Asn Ala Asn Ala Asn Ala Asn Ala Asn Ala Asn Ala Asn Ala Asn Ala
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 40

Asn Val Asn Val Asn Val Asn Val Asn Val Asn Val Asn Val Asn Val
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 41

Asn Leu Asn Leu Asn Leu Asn Leu Asn Leu Asn Leu Asn Leu Asn Leu
1               5                   10                  15

<210> SEQ ID NO 42
```

```
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 42

Asn Ile Asn Ile Asn Ile Asn Ile Asn Ile Asn Ile Asn Ile Asn Ile
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 43

Asn Met Asn Met Asn Met Asn Met Asn Met Asn Met Asn Met Asn Met
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 44

Asn Phe Asn Phe Asn Phe Asn Phe Asn Phe Asn Phe Asn Phe Asn Phe
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 45

Asn Trp Asn Trp Asn Trp Asn Trp Asn Trp Asn Trp Asn Trp Asn Trp
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 46

Asn Pro Asn Pro Asn Pro Asn Pro Asn Pro Asn Pro Asn Pro Asn Pro
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 47

Gln Gly Gln Gly Gln Gly Gln Gly Gln Gly Gln Gly Gln Gly Gln Gly
1               5                   10                  15

<210> SEQ ID NO 48
<211> LENGTH: 16
```

```
<212> TYPE: PRT
<213> ORGANISM: Artificial Sequence
<220> FEATURE:
<223> OTHER INFORMATION: Self-assembling peptide

<400> SEQUENCE: 48

Gln Ala Gln Ala Gln Ala Gln Ala Gln Ala Gln Ala Gln Ala Gln Ala
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 49

Gln Val Gln Val Gln Val Gln Val Gln Val Gln Val Gln Val Gln Val
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 50

Gln Leu Gln Leu Gln Leu Gln Leu Gln Leu Gln Leu Gln Leu Gln Leu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 51

Gln Ile Gln Ile Gln Ile Gln Ile Gln Ile Gln Ile Gln Ile Gln Ile
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 52

Gln Met Gln Met Gln Met Gln Met Gln Met Gln Met Gln Met Gln Met
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 53

Gln Phe Gln Phe Gln Phe Gln Phe Gln Phe Gln Phe Gln Phe Gln Phe
1               5                   10                  15

<210> SEQ ID NO 54
<211> LENGTH: 16
<212> TYPE: PRT
```

```
<213> ORGANISM: Artificial Sequence
<220> FEATURE:
<223> OTHER INFORMATION: Self-assembling peptide

<400> SEQUENCE: 54

Gln Trp Gln Trp Gln Trp Gln Trp Gln Trp Gln Trp Gln Trp Gln Trp
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 55

Gln Pro Gln Pro Gln Pro Gln Pro Gln Pro Gln Pro Gln Pro Gln Pro
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 56

Ala Glu Ala Lys Ala Glu Ala Lys Ala Glu Ala Lys Ala Glu Ala Lys
1               5                   10                  15

<210> SEQ ID NO 57
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 57

Arg Ala Asp Ala
1

<210> SEQ ID NO 58
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 58

Arg Ala Glu Ala Arg Ala Glu Ala Arg Ala Glu Ala Arg Ala Glu Ala
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Self-assembling peptide

<400> SEQUENCE: 59

Lys Ala Asp Ala Lys Ala Asp Ala Lys Ala Asp Ala Lys Ala Asp Ala
1               5                   10                  15

<210> SEQ ID NO 60
<211> LENGTH: 8
<212> TYPE: PRT
<213> ORGANISM: Artificial Sequence
```

-continued

```
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: Methylation
<220> FEATURE:
<221> NAME/KEY: MISC_FEATURE
<222> LOCATION: (1)..(1)
<223> OTHER INFORMATION: Modified with pyridoxamine phosphate
<220> FEATURE:
<221> NAME/KEY: MISC_FEATURE
<222> LOCATION: (7)..(7)
<223> OTHER INFORMATION: Xaa = ornithine
<220> FEATURE:
<221> NAME/KEY: MISC_FEATURE
<222> LOCATION: (8)..(8)
<223> OTHER INFORMATION: Amidation

<400> SEQUENCE: 60

Tyr Ile Thr Asn Cys Pro Xaa Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptoprionyl modification

<400> SEQUENCE: 61

Tyr Phe Gln Asn Cys Pro Arg
1               5

<210> SEQ ID NO 62
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (9)..(9)
<223> OTHER INFORMATION: Amidation

<400> SEQUENCE: 62

Cys Tyr Phe Gln Asn Cys Pro Arg Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Self-assembling peptide

<400> SEQUENCE: 63

Cys Tyr Phe Gln Asn Cys Pro Arg
1               5

<210> SEQ ID NO 64
<211> LENGTH: 9
<212> TYPE: PRT
<213> ORGANISM: Artificial Sequence
<220> FEATURE:
<223> OTHER INFORMATION: Self-assembling peptide
<220> FEATURE:
```

```
<221> NAME/KEY: MISC_FEATURE
<222> LOCATION: (9)..(9)
<223> OTHER INFORMATION: Amidation

<400> SEQUENCE: 64

Cys Tyr Ile Gln Asn Cys Pro Arg Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (4)..(5)
<223> OTHER INFORMATION: Aminosuccinyl modification
<220> FEATURE:
<221> NAME/KEY: MISC_FEATURE
<222> LOCATION: (7)..(7)
<223> OTHER INFORMATION: Amidation

<400> SEQUENCE: 65

Tyr Phe Gln Asn Pro Arg Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (4)..(5)
<223> OTHER INFORMATION: Aminosuccinyl modification
<220> FEATURE:
<221> NAME/KEY: MISC_FEATURE
<222> LOCATION: (7)..(7)
<223> OTHER INFORMATION: Amidation

<400> SEQUENCE: 66

Tyr Ile Gln Asn Pro Arg Gly
1               5

<210> SEQ ID NO 67
<211> LENGTH: 7
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptopropionyl-D-Pyridylanine modification
<220> FEATURE:
<221> NAME/KEY: MISC_FEATURE
<222> LOCATION: (7)..(7)
<223> OTHER INFORMATION: Amidation

<400> SEQUENCE: 67

Phe Gln Asn Cys Pro Arg Gly
1               5

<210> SEQ ID NO 68
<211> LENGTH: 9
<212> TYPE: PRT
<213> ORGANISM: Artificial Sequence
<220> FEATURE:
<223> OTHER INFORMATION: Self-assembling peptide
```

```
<220> FEATURE:
<221> NAME/KEY: MISC_FEATURE
<222> LOCATION: (1)..(1)
<223> OTHER INFORMATION: Deamino penicillamine modification
<220> FEATURE:
<221> NAME/KEY: MISC_FEATURE
<222> LOCATION: (9)..(9)
<223> OTHER INFORMATION: Amidation

<400> SEQUENCE: 68

Tyr Phe Val Asn Cys Pro Asp Arg Gly
1               5

<210> SEQ ID NO 69
<211> LENGTH: 8
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MISC_FEATURE
<222> LOCATION: (8)..(8)
<223> OTHER INFORMATION: Amidation

<400> SEQUENCE: 69

Tyr Phe Gln Asn Cys Pro Arg Gly
1               5

<210> SEQ ID NO 70
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MISC_FEATURE
<222> LOCATION: (9)..(9)
<223> OTHER INFORMATION: Amidation

<400> SEQUENCE: 70

Tyr Phe Gln Asn Cys Pro Asp Arg Gly
1               5

<210> SEQ ID NO 71
<211> LENGTH: 7
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptopropionyl modification

<400> SEQUENCE: 71

Tyr Phe Gln Asn Cys Pro Lys
1               5

<210> SEQ ID NO 72
<211> LENGTH: 9
<212> TYPE: PRT
<213> ORGANISM: Artificial Sequence
<220> FEATURE:
```

```
<223> OTHER INFORMATION: Self-assembling peptide
<220> FEATURE:
<221> NAME/KEY: MISC_FEATURE
<222> LOCATION: (9)..(9)
<223> OTHER INFORMATION: Amidation

<400> SEQUENCE: 72

Cys Tyr Phe Gln Asn Cys Pro Lys Gly
 1               5

<210> SEQ ID NO 73
<211> LENGTH: 8
<212> TYPE: PRT
<213> ORGANISM: Artificial Sequence
<220> FEATURE:
<223> OTHER INFORMATION: Self-assembling peptide

<400> SEQUENCE: 73

Cys Tyr Phe Gln Asn Cys Pro Lys
 1               5

<210> SEQ ID NO 74
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MISC_FEATURE
<222> LOCATION: (9)..(9)
<223> OTHER INFORMATION: Amidation

<400> SEQUENCE: 74

Tyr Phe Val Asn Cys Pro Asp Arg Gly
 1               5

<210> SEQ ID NO 75
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (8)..(8)
<223> OTHER INFORMATION: Xaa = ornithine
<220> FEATURE:
<221> NAME/KEY: MISC_FEATURE
<222> LOCATION: (9)..(9)
<223> OTHER INFORMATION: Amidation

<400> SEQUENCE: 75

Cys Phe Ile Gln Asn Cys Pro Xaa Gly
 1               5

<210> SEQ ID NO 76
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MISC_FEATURE
```

```
<222> LOCATION: (2)..(2)
<223> OTHER INFORMATION: ethoxy modification
<220> FEATURE:
<221> NAME/KEY: MISC_FEATURE
<222> LOCATION: (8)..(8)
<223> OTHER INFORMATION: Xaa = citrulline
<220> FEATURE:
<221> NAME/KEY: MISC_FEATURE
<222> LOCATION: (9)..(9)
<223> OTHER INFORMATION: Amidation

<400> SEQUENCE: 76

Asp Tyr Phe Val Asn Cys Pro Xaa Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MISC_FEATURE
<222> LOCATION: (1)..(1)
<223> OTHER INFORMATION: ethoxy modification
<220> FEATURE:
<221> NAME/KEY: MISC_FEATURE
<222> LOCATION: (8)..(8)
<223> OTHER INFORMATION: Amidation

<400> SEQUENCE: 77

Tyr Phe Val Asn Cys Pro Arg Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MISC_FEATURE
<222> LOCATION: (1)..(1)
<223> OTHER INFORMATION: METHYLATION
<220> FEATURE:
<221> NAME/KEY: MISC_FEATURE
<222> LOCATION: (8)..(8)
<223> OTHER INFORMATION: AMIDATION

<400> SEQUENCE: 78

Tyr Phe Gln Asn Cys Pro Arg Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MISC_FEATURE
```

```
<222> LOCATION: (1)..(1)
<223> OTHER INFORMATION: METHYLATION
<220> FEATURE:
<221> NAME/KEY: MISC_FEATURE
<222> LOCATION: (7)..(7)
<223> OTHER INFORMATION: Xaa = ornithine
<220> FEATURE:
<221> NAME/KEY: MISC_FEATURE
<222> LOCATION: (8)..(8)
<223> OTHER INFORMATION: Amidation

<400> SEQUENCE: 79

Tyr Ile Gln Asn Cys Pro Xaa Gly
1               5

<210> SEQ ID NO 80
<211> LENGTH: 7
<212> TYPE: PRT
<213> ORGANISM: Artificial Sequence
<220> FEATURE:
<223> OTHER INFORMATION: Self-assembling peptide

<400> SEQUENCE: 80

Gly Asp Arg Gly Asp Ser Pro
1               5

<210> SEQ ID NO 81
<211> LENGTH: 11
<212> TYPE: PRT
<213> ORGANISM: Artificial Sequence
<220> FEATURE:
<223> OTHER INFORMATION: Self-assembling peptide

<400> SEQUENCE: 81

Gly Asp Arg Gly Asp Ser Pro Ala Ser Ser Lys
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(2)
<223> OTHER INFORMATION: penicillamine modification

<400> SEQUENCE: 82

Gly Gly Arg Gly Asp Ser Pro Cys Ala
1               5

<210> SEQ ID NO 83
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 83

Gly Arg Ala Asp Ser Pro
1               5

<210> SEQ ID NO 84
<211> LENGTH: 7
<212> TYPE: PRT
<213> ORGANISM: Artificial Sequence
<220> FEATURE:
<223> OTHER INFORMATION: Self-assembling peptide
```

```
<400> SEQUENCE: 84

Gly Arg Gly Asp Asp Ser Pro
1               5

<210> SEQ ID NO 85
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 85

Gly Arg Gly Asp Asn Pro
1               5

<210> SEQ ID NO 86
<211> LENGTH: 5
<212> TYPE: PRT
<213> ORGANISM: Artificial Sequence
<220> FEATURE:
<223> OTHER INFORMATION: Self-assembling peptide

<400> SEQUENCE: 86

Gly Arg Gly Asp Ser
1               5

<210> SEQ ID NO 87
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 87

Gly Arg Gly Asp Ser Pro
1               5

<210> SEQ ID NO 88
<211> LENGTH: 7
<212> TYPE: PRT
<213> ORGANISM: Artificial Sequence
<220> FEATURE:
<223> OTHER INFORMATION: Self-assembling peptide

<400> SEQUENCE: 88

Gly Arg Gly Asp Ser Pro Cys
1               5

<210> SEQ ID NO 89
<211> LENGTH: 7
<212> TYPE: PRT
<213> ORGANISM: Artificial Sequence
<220> FEATURE:
<223> OTHER INFORMATION: Self-assembling peptide

<400> SEQUENCE: 89

Gly Arg Gly Asp Ser Pro Lys
1               5

<210> SEQ ID NO 90
<211> LENGTH: 6
<212> TYPE: PRT
<213> ORGANISM: Artificial Sequence
<220> FEATURE:
<223> OTHER INFORMATION: Self-assembling peptide
```

```
<400> SEQUENCE: 90

Gly Arg Gly Asp Thr Pro
1               5

<210> SEQ ID NO 91
<211> LENGTH: 5
<212> TYPE: PRT
<213> ORGANISM: Artificial Sequence
<220> FEATURE:
<223> OTHER INFORMATION: Self-assembling peptide

<400> SEQUENCE: 91

Gly Arg Gly Glu Ser
1               5

<210> SEQ ID NO 92
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 92

Gly Arg Gly Glu Ser Pro
1               5

<210> SEQ ID NO 93
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 93

Gly Arg Gly Glu Thr Pro
1               5

<210> SEQ ID NO 94
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 94

Lys Gly Asp Ser
1

<210> SEQ ID NO 95
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 95

Gly Ala Val Ser Thr Ala
1               5

<210> SEQ ID NO 96
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 96
```

Trp Thr Val Pro Thr Ala
1 5

```
<210> SEQ ID NO 97
<211> LENGTH: 11
<212> TYPE: PRT
<213> ORGANISM: Artificial Sequence
<220> FEATURE:
<223> OTHER INFORMATION: Self-assembling peptide

<400> SEQUENCE: 97

Thr Asp Val Asn Gly Asp Gly Arg His Asp Leu
1 5 10

<210> SEQ ID NO 98
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 98

Arg Glu Asp Val
1

<210> SEQ ID NO 99
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 99

Arg Gly Asp Cys
1

<210> SEQ ID NO 100
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 100

Arg Gly Asp Ser
1

<210> SEQ ID NO 101
<211> LENGTH: 10
<212> TYPE: PRT
<213> ORGANISM: Artificial Sequence
<220> FEATURE:
<223> OTHER INFORMATION: Self-assembling peptide

<400> SEQUENCE: 101

Arg Gly Asp Ser Pro Ala Ser Ser Lys Pro
1 5 10

<210> SEQ ID NO 102
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 102
```

Arg Gly Asp Thr
1

<210> SEQ ID NO 103
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 103

Arg Gly Asp Val
1

<210> SEQ ID NO 104
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 104

Arg Gly Glu Ser
1

<210> SEQ ID NO 105
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 105

Ser Asp Gly Arg
1

<210> SEQ ID NO 106
<211> LENGTH: 5
<212> TYPE: PRT
<213> ORGANISM: Artificial Sequence
<220> FEATURE:
<223> OTHER INFORMATION: Self-assembling peptide

<400> SEQUENCE: 106

Ser Asp Gly Arg Gly
1               5

<210> SEQ ID NO 107
<211> LENGTH: 5
<212> TYPE: PRT
<213> ORGANISM: Artificial Sequence
<220> FEATURE:
<223> OTHER INFORMATION: Self-assembling peptide

<400> SEQUENCE: 107

Tyr Arg Gly Asp Ser
1               5

<210> SEQ ID NO 108
<211> LENGTH: 14
<212> TYPE: PRT
<213> ORGANISM: Artificial Sequence
<220> FEATURE:
<223> OTHER INFORMATION: Self-assembling peptide

<400> SEQUENCE: 108

Glu Gly Val Asn Asp Asn Glu Glu Gly Phe Phe Ser Ala Arg

```
<210> SEQ ID NO 109
<211> LENGTH: 17
<212> TYPE: PRT
<213> ORGANISM: Artificial Sequence
<220> FEATURE:
<223> OTHER INFORMATION: Self-assembling peptide

<400> SEQUENCE: 109

Tyr Ala Asp Ser Gly Glu Gly Asp Phe Leu Ala Glu Gly Gly Gly Val
1               5                   10                  15
Arg

<210> SEQ ID NO 110
<211> LENGTH: 14
<212> TYPE: PRT
<213> ORGANISM: Artificial Sequence
<220> FEATURE:
<223> OTHER INFORMATION: Self-assembling peptide
<220> FEATURE:
<221> NAME/KEY: MISC_FEATURE
<222> LOCATION: (1)..(1)
<223> OTHER INFORMATION: Glp modification

<400> SEQUENCE: 110

Gly Val Asn Asp Asn Glu Glu Gly Phe Phe Ser Ala Arg Tyr
1               5                   10

<210> SEQ ID NO 111
<211> LENGTH: 4
<212> TYPE: PRT
<213> ORGANISM: Artificial Sequence
<220> FEATURE:
<223> OTHER INFORMATION: Peptide

<400> SEQUENCE: 111

Glu Ala Lys Ala
1

<210> SEQ ID NO 112
<211> LENGTH: 12
<212> TYPE: PRT
<213> ORGANISM: Artificial Sequence
<220> FEATURE:
<223> OTHER INFORMATION: Peptide

<400> SEQUENCE: 112

Arg Ala Arg Ala Arg Ala Asp Ala Asp Ala Asp Ala
1               5                   10

<210> SEQ ID NO 113
<211> LENGTH: 16
<212> TYPE: PRT
<213> ORGANISM: Artificial Sequence
<220> FEATURE:
<223> OTHER INFORMATION: Peptide

<400> SEQUENCE: 113

Arg Ala Arg Ala Arg Ala Arg Ala Asp Ala Asp Ala Asp Ala Asp Ala
1               5                   10                  15

<210> SEQ ID NO 114
<211> LENGTH: 8
<212> TYPE: PRT
<213> ORGANISM: Artificial Sequence
<220> FEATURE:
```

<223> OTHER INFORMATION: Self-assembling peptide

<400> SEQUENCE: 114

Arg Arg Arg Arg Asp Asp Asp Asp
1               5

<210> SEQ ID NO 115
<211> LENGTH: 8
<212> TYPE: PRT
<213> ORGANISM: Artificial Sequence
<220> FEATURE:
<223> OTHER INFORMATION: Self-assembling peptide

<400> SEQUENCE: 115

Gly Gly Gly Gly Ser Ser Ser Ser
1               5

<210> SEQ ID NO 116
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 116

Lys Lys Lys Lys
1

<210> SEQ ID NO 117
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 117

Arg Arg Arg Arg
1

<210> SEQ ID NO 118
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 118

His His His His
1

<210> SEQ ID NO 119
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 119

Asp Asp Asp Asp
1

<210> SEQ ID NO 120
<211> LENGTH: 4
<212> TYPE: PRT
<213> ORGANISM: Artificial Sequence
<220> FEATURE:
<223> OTHER INFORMATION: Self-assembling peptide

```
<400> SEQUENCE: 120

Glu Glu Glu Glu
1

<210> SEQ ID NO 121
<211> LENGTH: 4
<212> TYPE: PRT
<213> ORGANISM: Artificial Sequence
<220> FEATURE:
<223> OTHER INFORMATION: Self-assembling peptide

<400> SEQUENCE: 121

Gly Gln Gly Gln
1

<210> SEQ ID NO 122
<211> LENGTH: 6
<212> TYPE: PRT
<213> ORGANISM: Artificial Sequence
<220> FEATURE:
<223> OTHER INFORMATION: Self-assembling peptide

<400> SEQUENCE: 122

Gly Gly Gln Gln Gly Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Self-assembling peptide

<400> SEQUENCE: 123

Gly Gln Gln Gly Gln Gln Gly
1               5

<210> SEQ ID NO 124
<211> LENGTH: 8
<212> TYPE: PRT
<213> ORGANISM: Artificial Sequence
<220> FEATURE:
<223> OTHER INFORMATION: Self-assembling peptide

<400> SEQUENCE: 124

Gly Gly Gln Gly Gly Gln Gly Gly
1               5

<210> SEQ ID NO 125
<211> LENGTH: 16
<212> TYPE: PRT
<213> ORGANISM: Artificial Sequence
<220> FEATURE:
<223> OTHER INFORMATION: Peptide

<400> SEQUENCE: 125

Tyr Tyr Tyr Tyr Tyr Lys Tyr Asp Tyr Lys Tyr Asp Tyr Lys Tyr Asp
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Peptide
```

```
<400> SEQUENCE: 126

Gly Gly Gly Gly Gly Asp Gly Asp Gly Asp Gly Asp Gly Asp
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Peptide

<400> SEQUENCE: 127

Gly Gly Gly Gly Gly Glu Gly Glu Gly Glu Gly Glu Gly Glu
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Peptide

<400> SEQUENCE: 128

Gly Gly Gly Gly Gly Lys Gly Lys Gly Lys Gly Lys Gly Lys
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Peptide

<400> SEQUENCE: 129

Gly Gly Gly Gly Gly Arg Gly Arg Gly Arg Gly Arg Gly Arg
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Peptide

<400> SEQUENCE: 130

Gly Gly Gly Gly Gly His Gly His Gly His Gly His Gly His
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Peptide

<400> SEQUENCE: 131

Ala Ala Ala Ala Ala Asp Ala Asp Ala Asp Ala Asp Ala Asp
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Peptide

<400> SEQUENCE: 132
```

Ala Ala Ala Ala Ala Glu Ala Glu Ala Glu Ala Glu Ala Glu
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Peptide

<400> SEQUENCE: 133

Ala Ala Ala Ala Ala Lys Ala Lys Ala Lys Ala Lys Ala Lys
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Peptide

<400> SEQUENCE: 134

Ala Ala Ala Ala Ala Arg Ala Arg Ala Arg Ala Arg Ala Arg
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Peptide

<400> SEQUENCE: 135

Ala Ala Ala Ala Ala His Ala His Ala His Ala His Ala His
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Peptide

<400> SEQUENCE: 136

Val Val Val Val Val Asp Val Asp Val Asp Val Asp Val Asp
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Peptide

<400> SEQUENCE: 137

Val Val Val Val Val Glu Val Glu Val Glu Val Glu Val Glu
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Peptide

<400> SEQUENCE: 138

Val Val Val Val Val Lys Val Lys Val Lys Val Lys Val Lys Val Lys
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Peptide

<400> SEQUENCE: 139

Val Val Val Val Val Arg Val Arg Val Arg Val Arg Val Arg Val Arg
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Peptide

<400> SEQUENCE: 140

Val Val Val Val Val His Val His Val His Val His Val His Val His
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Peptide

<400> SEQUENCE: 141

Leu Leu Leu Leu Leu Asp Leu Asp Leu Asp Leu Asp Leu Asp Leu Asp
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Peptide

<400> SEQUENCE: 142

Leu Leu Leu Leu Leu Glu Leu Glu Leu Glu Leu Glu Leu Glu Leu Glu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Peptide

<400> SEQUENCE: 143

Leu Leu Leu Leu Leu Lys Leu Lys Leu Lys Leu Lys Leu Lys Leu Lys
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Peptide

<400> SEQUENCE: 144

Leu Leu Leu Leu Leu Arg Leu Arg Leu Arg Leu Arg Leu Arg Leu Arg

-continued

<210> SEQ ID NO 145
<211> LENGTH: 16
<212> TYPE: PRT
<213> ORGANISM: Artificial Sequence
<220> FEATURE:
<223> OTHER INFORMATION: Peptide

<400> SEQUENCE: 145

Leu Leu Leu Leu Leu His Leu His Leu His Leu His Leu His Leu His
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Peptide

<400> SEQUENCE: 146

Ile Ile Ile Ile Ile Asp Ile Asp Ile Asp Ile Asp Ile Asp Ile Asp
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Peptide

<400> SEQUENCE: 147

Ile Ile Ile Ile Ile Glu Ile Glu Ile Glu Ile Glu Ile Glu Ile Glu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Peptide

<400> SEQUENCE: 148

Ile Ile Ile Ile Ile Lys Ile Lys Ile Lys Ile Lys Ile Lys Ile Lys
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Peptide

<400> SEQUENCE: 149

Ile Ile Ile Ile Ile Arg Ile Arg Ile Arg Ile Arg Ile Arg Ile Arg
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Peptide

<400> SEQUENCE: 150

Ile Ile Ile Ile Ile His Ile His Ile His Ile His Ile His Ile His
1               5                   10                  15

```
<210> SEQ ID NO 151
<211> LENGTH: 16
<212> TYPE: PRT
<213> ORGANISM: Artificial Sequence
<220> FEATURE:
<223> OTHER INFORMATION: Peptide

<400> SEQUENCE: 151

Met Met Met Met Met Asp Met Asp Met Asp Met Asp Met Asp Met Asp
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Peptide

<400> SEQUENCE: 152

Met Met Met Met Met Glu Met Glu Met Glu Met Glu Met Glu Met Glu
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Peptide

<400> SEQUENCE: 153

Met Met Met Met Met Lys Met Lys Met Lys Met Lys Met Lys Met Lys
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Peptide

<400> SEQUENCE: 154

Met Met Met Met Met Arg Met Arg Met Arg Met Arg Met Arg Met Arg
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Peptide

<400> SEQUENCE: 155

Met Met Met Met Met His Met His Met His Met His Met His Met His
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Peptide

<400> SEQUENCE: 156

Phe Phe Phe Phe Phe Asp Phe Asp Phe Asp Phe Asp Phe Asp Phe Asp
1               5                   10                  15
```

```
<210> SEQ ID NO 157
<211> LENGTH: 16
<212> TYPE: PRT
<213> ORGANISM: Artificial Sequence
<220> FEATURE:
<223> OTHER INFORMATION: Peptide

<400> SEQUENCE: 157

Phe Phe Phe Phe Phe Glu Phe Glu Phe Glu Phe Glu Phe Glu Phe Glu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Peptide

<400> SEQUENCE: 158

Phe Phe Phe Phe Phe Lys Phe Lys Phe Lys Phe Lys Phe Lys Phe Lys
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Peptide

<400> SEQUENCE: 159

Phe Phe Phe Phe Phe Arg Phe Arg Phe Arg Phe Arg Phe Arg Phe Arg
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Peptide

<400> SEQUENCE: 160

Phe Phe Phe Phe Phe His Phe His Phe His Phe His Phe His Phe His
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Peptide

<400> SEQUENCE: 161

Trp Trp Trp Trp Trp Asp Trp Asp Trp Asp Trp Asp Trp Asp Trp Asp
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Peptide

<400> SEQUENCE: 162

Trp Trp Trp Trp Trp Glu Trp Glu Trp Glu Trp Glu Trp Glu Trp Glu
1               5                   10                  15
```

<210> SEQ ID NO 163
<211> LENGTH: 16
<212> TYPE: PRT
<213> ORGANISM: Artificial Sequence
<220> FEATURE:
<223> OTHER INFORMATION: Peptide

<400> SEQUENCE: 163

Trp Trp Trp Trp Trp Lys Trp Lys Trp Lys Trp Lys Trp Lys
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Peptide

<400> SEQUENCE: 164

Trp Trp Trp Trp Trp Arg Trp Arg Trp Arg Trp Arg Trp Arg
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Peptide

<400> SEQUENCE: 165

Trp Trp Trp Trp Trp His Trp His Trp His Trp His Trp His
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Peptide

<400> SEQUENCE: 166

Pro Pro Pro Pro Pro Asp Pro Asp Pro Asp Pro Asp Pro Asp
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Peptide

<400> SEQUENCE: 167

Pro Pro Pro Pro Pro Glu Pro Glu Pro Glu Pro Glu Pro Glu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Peptide

<400> SEQUENCE: 168

Pro Pro Pro Pro Pro Lys Pro Lys Pro Lys Pro Lys Pro Lys
1               5                   10                  15

<210> SEQ ID NO 169

<211> LENGTH: 16
<212> TYPE: PRT
<213> ORGANISM: Artificial Sequence
<220> FEATURE:
<223> OTHER INFORMATION: Peptide

<400> SEQUENCE: 169

Pro Pro Pro Pro Pro Arg Pro Arg Pro Arg Pro Arg Pro Arg Pro Arg
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Peptide

<400> SEQUENCE: 170

Pro Pro Pro Pro Pro His Pro His Pro His Pro His Pro His Pro His
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Peptide

<400> SEQUENCE: 171

Ala Ala Ala Ala Ala Arg Ala Asp Ala Arg Ala Asp Ala Arg Ala Asp
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Peptide

<400> SEQUENCE: 172

Ala Ala Ala Ala Ala Arg Ala Arg Ala Asp Ala Asp Ala Arg Ala Arg
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Peptide

<400> SEQUENCE: 173

Ala Ala Ala Ala Ala Glu Ala Lys Ala Glu Ala Lys Ala Glu Ala Lys
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Peptide

<400> SEQUENCE: 174

Ala Ala Ala Ala Ala Glu Ala Glu Ala Lys Ala Lys Ala Glu Ala Glu
1               5                   10                  15

<210> SEQ ID NO 175
<211> LENGTH: 16

```
<212> TYPE: PRT
<213> ORGANISM: Artificial Sequence
<220> FEATURE:
<223> OTHER INFORMATION: Peptide

<400> SEQUENCE: 175

Ala Ala Ala Ala Ala Arg Ala Glu Ala Arg Ala Glu Ala Arg Ala Glu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Peptide

<400> SEQUENCE: 176

Ala Ala Ala Ala Ala Arg Ala Arg Ala Glu Ala Glu Ala Arg Ala Glu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Peptide

<400> SEQUENCE: 177

Ala Ala Ala Ala Ala Lys Ala Asp Ala Lys Ala Asp Ala Lys Ala Asp
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Peptide

<400> SEQUENCE: 178

Ala Ala Ala Ala Ala Glu Ala His Ala Glu Ala His Ala Glu Ala His
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Peptide

<400> SEQUENCE: 179

Ala Ala Ala Ala Ala Glu Ala Glu Ala His Ala His Ala Glu Ala Glu
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Peptide

<400> SEQUENCE: 180

Ala Ala Ala Ala Ala Arg Ala Arg Ala Arg Ala Arg Ala Arg Ala Arg
1               5                   10                  15

<210> SEQ ID NO 181
<211> LENGTH: 16
<212> TYPE: PRT
```

```
<213> ORGANISM: Artificial Sequence
<220> FEATURE:
<223> OTHER INFORMATION: Peptide

<400> SEQUENCE: 181

Ala Ala Ala Ala Ala Arg Ala Arg Ala Arg Ala Arg Ala Asp Ala Asp
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Peptide

<400> SEQUENCE: 182

Ala Ala Ala Ala Ala Arg Ala Arg Ala Arg Ala Asp Ala Asp Ala Asp
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Peptide

<400> SEQUENCE: 183

Ala Ala Ala Ala Ala His Ala Asp Ala His Ala Asp Ala His Ala Asp
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Peptide

<400> SEQUENCE: 184

Ala Ala Ala Ala Ala His Ala His Ala His Ala His Ala His Ala His
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Peptide

<400> SEQUENCE: 185

Ala Ala Ala Ala Ala His Ala Asp Ala Asp Ala His Ala Asp Ala Asp
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Peptide

<400> SEQUENCE: 186

Ala Ala Ala Ala Ala His Ala Glu Ala Glu Ala His Ala Glu Ala Glu
1               5                   10                  15

<210> SEQ ID NO 187
<211> LENGTH: 16
<212> TYPE: PRT
<213> ORGANISM: Artificial Sequence
```

```
<220> FEATURE:
<223> OTHER INFORMATION: Peptide

<400> SEQUENCE: 187

Gly Gly Gly Gly Gly Arg Gly Asp Gly Arg Gly Asp Gly Arg Gly Asp
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Peptide

<400> SEQUENCE: 188

Gly Gly Gly Gly Gly Arg Gly Arg Gly Asp Gly Asp Gly Arg Gly Arg
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Peptide

<400> SEQUENCE: 189

Gly Gly Gly Gly Gly Glu Gly Lys Gly Glu Gly Lys Gly Glu Gly Lys
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Peptide

<400> SEQUENCE: 190

Gly Gly Gly Gly Gly Glu Gly Glu Gly Lys Gly Lys Gly Glu Gly Glu
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Peptide

<400> SEQUENCE: 191

Gly Gly Gly Gly Gly Arg Gly Glu Gly Arg Gly Glu Gly Arg Gly Glu
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Peptide

<400> SEQUENCE: 192

Gly Gly Gly Gly Gly Arg Gly Arg Gly Glu Gly Glu Gly Arg Gly Glu
1               5                   10                  15

<210> SEQ ID NO 193
<211> LENGTH: 16
<212> TYPE: PRT
<213> ORGANISM: Artificial Sequence
<220> FEATURE:
```

```
<223> OTHER INFORMATION: Peptide

<400> SEQUENCE: 193

Gly Gly Gly Gly Gly Lys Gly Asp Gly Lys Gly Asp Gly Lys Gly Asp
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Peptide

<400> SEQUENCE: 194

Gly Gly Gly Gly Gly Glu Gly His Gly Glu Gly His Gly Glu Gly His
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Peptide

<400> SEQUENCE: 195

Gly Gly Gly Gly Gly Glu Gly Glu Gly His Gly His Gly Glu Gly Glu
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Peptide

<400> SEQUENCE: 196

Gly Gly Gly Gly Gly Arg Gly Arg Gly Arg Gly Arg Gly Arg Gly Arg
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Peptide

<400> SEQUENCE: 197

Gly Gly Gly Gly Gly Arg Gly Arg Gly Arg Gly Arg Gly Asp Gly Asp
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Peptide

<400> SEQUENCE: 198

Gly Gly Gly Gly Gly Arg Gly Arg Gly Arg Gly Asp Gly Asp Gly Asp
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Peptide
```

<400> SEQUENCE: 199

Gly Gly Gly Gly Gly His Gly Asp Gly His Gly Asp Gly His Gly Asp
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Peptide

<400> SEQUENCE: 200

Gly Gly Gly Gly Gly His Gly His Gly His Gly His Gly His Gly His
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Peptide

<400> SEQUENCE: 201

Gly Gly Gly Gly Gly His Gly Asp Gly Asp Gly His Gly Asp Gly Asp
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Peptide

<400> SEQUENCE: 202

Gly Gly Gly Gly Gly His Gly Glu Gly Glu Gly His Gly Glu Gly Glu
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Peptide

<400> SEQUENCE: 203

Val Val Val Val Val Arg Val Asp Val Arg Val Asp Val Arg Val Asp
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Peptide

<400> SEQUENCE: 204

Val Val Val Val Val Arg Val Arg Val Asp Val Asp Val Arg Val Arg
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: Peptide

```
<400> SEQUENCE: 205

Val Val Val Val Glu Val Lys Val Glu Lys Val Glu Val Lys
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Peptide

<400> SEQUENCE: 206

Val Val Val Val Val Glu Val Glu Val Lys Val Lys Val Glu Val Glu
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: Peptide

<400> SEQUENCE: 207

Val Val Val Val Val Arg Val Glu Val Arg Val Glu Val Arg Val Glu
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Peptide

<400> SEQUENCE: 208

Val Val Val Val Val Arg Val Arg Val Glu Val Glu Val Arg Val Glu
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Peptide

<400> SEQUENCE: 209

Val Val Val Val Lys Val Asp Val Lys Val Asp Val Lys Val Asp
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: Peptide

<400> SEQUENCE: 210

Val Val Val Val Val Glu Val His Val Glu Val His Val Glu Val His
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Peptide

<400> SEQUENCE: 211
```

Val Val Val Val Glu Val Glu Val His Val His Val Glu Val Glu
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Peptide

<400> SEQUENCE: 212

Val Val Val Val Arg Val Arg Val Arg Val Arg Val Arg Val Arg
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Peptide

<400> SEQUENCE: 213

Val Val Val Val Arg Val Arg Val Arg Val Arg Val Asp Val Asp
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Peptide

<400> SEQUENCE: 214

Val Val Val Val Arg Val Arg Val Arg Val Asp Val Asp Val Asp
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Peptide

<400> SEQUENCE: 215

Val Val Val Val Val His Val Asp Val His Val Asp Val His Val Asp
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: Peptide

<400> SEQUENCE: 216

Val Val Val Val Val His Val His Val His Val His Val His Val His
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Peptide

<400> SEQUENCE: 217

Val Val Val Val Val His Val Asp Val Asp Val His Val Asp Val Asp
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Peptide

<400> SEQUENCE: 218

Val Val Val Val Val His Val Glu Val Glu Val His Val Glu Val Glu
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Peptide

<400> SEQUENCE: 219

Leu Leu Leu Leu Leu Arg Leu Asp Leu Arg Leu Asp Leu Arg Leu Asp
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Peptide

<400> SEQUENCE: 220

Leu Leu Leu Leu Leu Arg Leu Arg Leu Asp Leu Asp Leu Arg Leu Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Peptide

<400> SEQUENCE: 221

Leu Leu Leu Leu Leu Glu Leu Lys Leu Glu Leu Lys Leu Glu Leu Lys
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Peptide

<400> SEQUENCE: 222

Leu Leu Leu Leu Leu Glu Leu Glu Leu Lys Leu Lys Leu Glu Leu Glu
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Peptide

<400> SEQUENCE: 223

Leu Leu Leu Leu Leu Arg Leu Glu Leu Arg Leu Glu Leu Arg Leu Glu

-continued

```
<210> SEQ ID NO 224
<211> LENGTH: 16
<212> TYPE: PRT
<213> ORGANISM: Artificial Sequence
<220> FEATURE:
<223> OTHER INFORMATION: Peptide

<400> SEQUENCE: 224

Leu Leu Leu Leu Leu Arg Leu Arg Leu Glu Leu Glu Leu Arg Leu Glu
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Peptide

<400> SEQUENCE: 225

Leu Leu Leu Leu Leu Lys Leu Asp Leu Lys Leu Asp Leu Lys Leu Asp
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Peptide

<400> SEQUENCE: 226

Leu Leu Leu Leu Leu Glu Leu His Leu Glu Leu His Leu Glu Leu His
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Peptide

<400> SEQUENCE: 227

Leu Leu Leu Leu Leu Glu Leu Glu Leu His Leu His Leu Glu Leu Glu
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Peptide

<400> SEQUENCE: 228

Leu Leu Leu Leu Leu Arg Leu Arg Leu Arg Leu Arg Leu Arg Leu Arg
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Peptide

<400> SEQUENCE: 229

Leu Leu Leu Leu Leu Arg Leu Arg Leu Arg Leu Arg Leu Asp Leu Asp
1               5                   10                  15
```

<210> SEQ ID NO 230
<211> LENGTH: 16
<212> TYPE: PRT
<213> ORGANISM: Artificial Sequence
<220> FEATURE:
<223> OTHER INFORMATION: Peptide

<400> SEQUENCE: 230

Leu Leu Leu Leu Leu Arg Leu Arg Leu Arg Leu Asp Leu Asp Leu Asp
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Peptide

<400> SEQUENCE: 231

Leu Leu Leu Leu Leu His Leu Asp Leu His Leu Asp Leu His Leu Asp
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Peptide

<400> SEQUENCE: 232

Leu Leu Leu Leu Leu His Leu His Leu His Leu His Leu His Leu His
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Peptide

<400> SEQUENCE: 233

Leu Leu Leu Leu Leu His Leu Asp Leu Asp Leu His Leu Asp Leu Asp
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Peptide

<400> SEQUENCE: 234

Leu Leu Leu Leu Leu His Leu Glu Leu Glu Leu His Leu Glu Leu Glu
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Peptide

<400> SEQUENCE: 235

Ile Ile Ile Ile Ile Arg Ile Asp Ile Arg Ile Asp Ile Arg Ile Asp
1               5                   10                  15

```
<210> SEQ ID NO 236
<211> LENGTH: 16
<212> TYPE: PRT
<213> ORGANISM: Artificial Sequence
<220> FEATURE:
<223> OTHER INFORMATION: Peptide

<400> SEQUENCE: 236

Ile Ile Ile Ile Ile Arg Ile Arg Ile Asp Ile Asp Ile Arg Ile Arg
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Peptide

<400> SEQUENCE: 237

Ile Ile Ile Ile Ile Glu Ile Lys Ile Glu Ile Lys Ile Glu Ile Lys
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Peptide

<400> SEQUENCE: 238

Ile Ile Ile Ile Ile Glu Ile Glu Ile Lys Ile Lys Ile Glu Ile Glu
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Peptide

<400> SEQUENCE: 239

Ile Ile Ile Ile Ile Arg Ile Glu Ile Arg Ile Glu Ile Arg Ile Glu
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Peptide

<400> SEQUENCE: 240

Ile Ile Ile Ile Ile Arg Ile Arg Ile Glu Ile Glu Ile Arg Ile Glu
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Peptide

<400> SEQUENCE: 241

Ile Ile Ile Ile Ile Lys Ile Asp Ile Lys Ile Asp Ile Lys Ile Asp
1               5                   10                  15
```

```
<210> SEQ ID NO 242
<211> LENGTH: 16
<212> TYPE: PRT
<213> ORGANISM: Artificial Sequence
<220> FEATURE:
<223> OTHER INFORMATION: Peptide

<400> SEQUENCE: 242

Ile Ile Ile Ile Ile Glu Ile His Ile Glu Ile His Ile Glu Ile His
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Peptide

<400> SEQUENCE: 243

Ile Ile Ile Ile Ile Glu Ile Glu Ile His Ile His Ile Glu Ile Glu
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Peptide

<400> SEQUENCE: 244

Ile Ile Ile Ile Ile Arg Ile Arg Ile Arg Ile Arg Ile Arg Ile Arg
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Peptide

<400> SEQUENCE: 245

Ile Ile Ile Ile Ile Arg Ile Arg Ile Arg Ile Arg Ile Asp Ile Asp
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Peptide

<400> SEQUENCE: 246

Ile Ile Ile Ile Ile Arg Ile Arg Ile Arg Ile Asp Ile Asp Ile Asp
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Peptide

<400> SEQUENCE: 247

Ile Ile Ile Ile Ile His Ile Asp Ile His Ile Asp Ile His Ile Asp
1               5                   10                  15

<210> SEQ ID NO 248
```

```
<211> LENGTH: 16
<212> TYPE: PRT
<213> ORGANISM: Artificial Sequence
<220> FEATURE:
<223> OTHER INFORMATION: Peptide

<400> SEQUENCE: 248

Ile Ile Ile Ile Ile His Ile His Ile His Ile His Ile His
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Peptide

<400> SEQUENCE: 249

Ile Ile Ile Ile Ile His Ile Asp Ile Asp Ile His Ile Asp Ile Asp
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Peptide

<400> SEQUENCE: 250

Ile Ile Ile Ile Ile His Ile Glu Ile Glu Ile His Ile Glu Ile Glu
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Peptide

<400> SEQUENCE: 251

Met Met Met Met Met Arg Met Asp Met Arg Met Asp Met Arg Met Asp
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: Peptide

<400> SEQUENCE: 252

Met Met Met Met Met Arg Met Arg Met Asp Met Asp Met Arg Met Arg
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Peptide

<400> SEQUENCE: 253

Met Met Met Met Met Glu Met Lys Met Glu Met Lys Met Glu Met Lys
1               5                   10                  15

<210> SEQ ID NO 254
<211> LENGTH: 16
```

```
<212> TYPE: PRT
<213> ORGANISM: Artificial Sequence
<220> FEATURE:
<223> OTHER INFORMATION: Peptid

<400> SEQUENCE: 254

Met Met Met Met Met Glu Met Glu Met Lys Met Lys Met Glu Met Glu
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Peptide

<400> SEQUENCE: 255

Met Met Met Met Met Arg Met Glu Met Arg Met Glu Met Arg Met Glu
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Peptide

<400> SEQUENCE: 256

Met Met Met Met Met Arg Met Arg Met Glu Met Glu Met Arg Met Glu
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Peptide

<400> SEQUENCE: 257

Met Met Met Met Met Lys Met Asp Met Lys Met Asp Met Lys Met Asp
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Peptide

<400> SEQUENCE: 258

Met Met Met Met Met Glu Met His Met Glu Met His Met Glu Met His
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Peptide

<400> SEQUENCE: 259

Met Met Met Met Met Glu Met Glu Met His Met His Met Glu Met Glu
1               5                   10                  15

<210> SEQ ID NO 260
<211> LENGTH: 16
<212> TYPE: PRT
```

```
<213> ORGANISM: Artificial Sequence
<220> FEATURE:
<223> OTHER INFORMATION: Peptide

<400> SEQUENCE: 260

Met Met Met Met Met Arg Met Arg Met Arg Met Arg Met Arg Met Arg
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Peptide

<400> SEQUENCE: 261

Met Met Met Met Met Arg Met Arg Met Arg Met Arg Met Asp Met Asp
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Peptide

<400> SEQUENCE: 262

Met Met Met Met Met Arg Met Arg Met Arg Met Asp Met Asp Met Asp
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Peptide

<400> SEQUENCE: 263

Met Met Met Met Met His Met Asp Met His Met Asp Met His Met Asp
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: Peptide

<400> SEQUENCE: 264

Met Met Met Met Met His Met His Met His Met His Met His Met His
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Peptide

<400> SEQUENCE: 265

Met Met Met Met Met His Met Asp Met Asp Met His Met Asp Met Asp
1               5                   10                  15

<210> SEQ ID NO 266
<211> LENGTH: 16
<212> TYPE: PRT
<213> ORGANISM: Artificial Sequence
```

```
<220> FEATURE:
<223> OTHER INFORMATION: Peptide

<400> SEQUENCE: 266

Met Met Met Met Met His Met Glu Met Glu Met His Met Glu Met Glu
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Peptide

<400> SEQUENCE: 267

Phe Phe Phe Phe Phe Arg Phe Asp Phe Arg Phe Asp Phe Arg Phe Asp
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Peptide

<400> SEQUENCE: 268

Phe Phe Phe Phe Phe Arg Phe Arg Phe Asp Phe Asp Phe Arg Phe Arg
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Peptide

<400> SEQUENCE: 269

Phe Phe Phe Phe Phe Glu Phe Lys Phe Glu Phe Lys Phe Glu Phe Lys
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: Peptide

<400> SEQUENCE: 270

Phe Phe Phe Phe Phe Glu Phe Glu Phe Lys Phe Lys Phe Glu Phe Glu
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Peptide

<400> SEQUENCE: 271

Phe Phe Phe Phe Phe Arg Phe Glu Phe Arg Phe Glu Phe Arg Phe Glu
1               5                   10                  15

<210> SEQ ID NO 272
<211> LENGTH: 16
<212> TYPE: PRT
<213> ORGANISM: Artificial Sequence
<220> FEATURE:
```

<223> OTHER INFORMATION: Peptide

<400> SEQUENCE: 272

Phe Phe Phe Phe Phe Arg Phe Arg Phe Glu Phe Glu Phe Arg Phe Glu
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Peptide

<400> SEQUENCE: 273

Phe Phe Phe Phe Phe Lys Phe Asp Phe Lys Phe Asp Phe Lys Phe Asp
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Peptide

<400> SEQUENCE: 274

Phe Phe Phe Phe Phe Glu Phe His Phe Glu Phe His Phe Glu Phe His
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Peptide

<400> SEQUENCE: 275

Phe Phe Phe Phe Phe Glu Phe Glu Phe His Phe His Phe Glu Phe Glu
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Peptide

<400> SEQUENCE: 276

Phe Phe Phe Phe Phe Arg Phe Arg Phe Arg Phe Arg Phe Arg Phe Arg
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Peptide

<400> SEQUENCE: 277

Phe Phe Phe Phe Phe Arg Phe Arg Phe Arg Phe Arg Phe Asp Phe Asp
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Peptide

<400> SEQUENCE: 278

Phe Phe Phe Phe Phe Arg Phe Arg Phe Arg Phe Asp Phe Asp Phe Asp
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Peptide

<400> SEQUENCE: 279

Phe Phe Phe Phe Phe His Phe Asp Phe His Phe Asp Phe His Phe Asp
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Peptide

<400> SEQUENCE: 280

Phe Phe Phe Phe Phe His Phe His Phe His Phe His Phe His Phe His
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Peptide

<400> SEQUENCE: 281

Phe Phe Phe Phe Phe His Phe Asp Phe Asp Phe His Phe Asp Phe Asp
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Peptide

<400> SEQUENCE: 282

Phe Phe Phe Phe Phe His Phe Glu Phe Glu Phe His Phe Glu Phe Glu
1               5                   10                  15

<210> SEQ ID NO 283
<211> LENGTH: 16
<212> TYPE: PRT
<213> ORGANISM: Artificial Sequence
<220> FEATURE:
<223> OTHER INFORMATION: Peptide

<400> SEQUENCE: 283

Trp Trp Trp Trp Trp Arg Trp Asp Trp Arg Trp Asp Trp Arg Trp Asp
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Peptide

```
<400> SEQUENCE: 284

Trp Trp Trp Trp Trp Arg Trp Arg Trp Asp Trp Asp Trp Arg Trp Arg
1               5                   10                  15

<210> SEQ ID NO 285
<211> LENGTH: 16
<212> TYPE: PRT
<213> ORGANISM: Artificial Sequence
<220> FEATURE:
<223> OTHER INFORMATION: Peptide

<400> SEQUENCE: 285

Trp Trp Trp Trp Trp Glu Trp Lys Trp Glu Trp Lys Trp Glu Trp Lys
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Peptide

<400> SEQUENCE: 286

Trp Trp Trp Trp Trp Glu Trp Glu Trp Lys Trp Lys Trp Glu Trp Glu
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Peptide

<400> SEQUENCE: 287

Trp Trp Trp Trp Trp Arg Trp Glu Trp Arg Trp Glu Trp Arg Trp Glu
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Peptide

<400> SEQUENCE: 288

Trp Trp Trp Trp Trp Arg Trp Arg Trp Glu Trp Glu Trp Arg Trp Glu
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Peptide

<400> SEQUENCE: 289

Trp Trp Trp Trp Trp Lys Trp Asp Trp Lys Trp Asp Trp Lys Trp Asp
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Peptide

<400> SEQUENCE: 290
```

Trp Trp Trp Trp Trp Glu Trp His Trp Glu Trp His Trp Glu Trp His
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Peptide

<400> SEQUENCE: 291

Trp Trp Trp Trp Trp Glu Trp Glu Trp His Trp His Trp Glu Trp Glu
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Peptide

<400> SEQUENCE: 292

Trp Trp Trp Trp Trp Arg Trp Arg Trp Arg Trp Arg Trp Arg Trp Arg
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Peptide

<400> SEQUENCE: 293

Trp Trp Trp Trp Trp Arg Trp Arg Trp Arg Trp Arg Trp Asp Trp Asp
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Peptide

<400> SEQUENCE: 294

Trp Trp Trp Trp Trp Arg Trp Arg Trp Arg Trp Asp Trp Asp Trp Asp
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Peptide

<400> SEQUENCE: 295

Trp Trp Trp Trp Trp His Trp Asp Trp His Trp Asp Trp His Trp Asp
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Peptide

<400> SEQUENCE: 296

```
Trp Trp Trp Trp Trp His Trp His Trp His Trp His Trp His
1               5                   10                  15
```

<210> SEQ ID NO 297
<211> LENGTH: 16
<212> TYPE: PRT
<213> ORGANISM: Artificial Sequence
<220> FEATURE:
<223> OTHER INFORMATION: Peptide

<400> SEQUENCE: 297

```
Trp Trp Trp Trp Trp His Trp Asp Trp Asp Trp His Trp Asp Trp Asp
1               5                   10                  15
```

<210> SEQ ID NO 298
<211> LENGTH: 16
<212> TYPE: PRT
<213> ORGANISM: Artificial Sequence
<220> FEATURE:
<223> OTHER INFORMATION: Peptide

<400> SEQUENCE: 298

```
Trp Trp Trp Trp Trp His Trp Glu Trp Glu Trp His Trp Glu Trp Glu
1               5                   10                  15
```

<210> SEQ ID NO 299
<211> LENGTH: 16
<212> TYPE: PRT
<213> ORGANISM: Artificial Sequence
<220> FEATURE:
<223> OTHER INFORMATION: Peptide

<400> SEQUENCE: 299

```
Pro Pro Pro Pro Pro Arg Pro Asp Pro Arg Pro Asp Pro Arg Pro Asp
1               5                   10                  15
```

<210> SEQ ID NO 300
<211> LENGTH: 16
<212> TYPE: PRT
<213> ORGANISM: Artificial Sequence
<220> FEATURE:
<223> OTHER INFORMATION: Peptide

<400> SEQUENCE: 300

```
Pro Pro Pro Pro Pro Arg Pro Arg Pro Asp Pro Asp Pro Arg Pro Arg
1               5                   10                  15
```

<210> SEQ ID NO 301
<211> LENGTH: 16
<212> TYPE: PRT
<213> ORGANISM: Artificial Sequence
<220> FEATURE:
<223> OTHER INFORMATION: Peptide

<400> SEQUENCE: 301

```
Pro Pro Pro Pro Pro Glu Pro Lys Pro Glu Pro Lys Pro Glu Pro Lys
1               5                   10                  15
```

<210> SEQ ID NO 302
<211> LENGTH: 16
<212> TYPE: PRT
<213> ORGANISM: Artificial Sequence
<220> FEATURE:
<223> OTHER INFORMATION: Peptide

<400> SEQUENCE: 302

```
Pro Pro Pro Pro Pro Glu Pro Glu Pro Lys Pro Lys Pro Glu Pro Glu
```

-continued

<210> SEQ ID NO 303
<211> LENGTH: 16
<212> TYPE: PRT
<213> ORGANISM: Artificial Sequence
<220> FEATURE:
<223> OTHER INFORMATION: Peptide

<400> SEQUENCE: 303

Pro Pro Pro Pro Pro Arg Pro Glu Pro Arg Pro Glu Pro Arg Pro Glu
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Peptide

<400> SEQUENCE: 304

Pro Pro Pro Pro Pro Arg Pro Arg Pro Glu Pro Glu Pro Arg Pro Glu
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Peptide

<400> SEQUENCE: 305

Pro Pro Pro Pro Pro Lys Pro Asp Pro Lys Pro Asp Pro Lys Pro Asp
1               5                   10                  15

<210> SEQ ID NO 306
<211> LENGTH: 16
<212> TYPE: PRT
<213> ORGANISM: Artificial Sequence
<220> FEATURE:
<223> OTHER INFORMATION: Peptide

<400> SEQUENCE: 306

Pro Pro Pro Pro Pro Glu Pro His Pro Glu Pro His Pro Glu Pro His
1               5                   10                  15

<210> SEQ ID NO 307
<211> LENGTH: 16
<212> TYPE: PRT
<213> ORGANISM: Artificial Sequence
<220> FEATURE:
<223> OTHER INFORMATION: Peptide

<400> SEQUENCE: 307

Pro Pro Pro Pro Pro Glu Pro Glu Pro His Pro His Pro Glu Pro Glu
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Peptide

<400> SEQUENCE: 308

Pro Pro Pro Pro Pro Arg Pro Arg Pro Arg Pro Arg Pro Arg Pro Arg
1               5                   10                  15

<210> SEQ ID NO 309
<211> LENGTH: 16
<212> TYPE: PRT
<213> ORGANISM: Artificial Sequence
<220> FEATURE:
<223> OTHER INFORMATION: Peptide

<400> SEQUENCE: 309

Pro Pro Pro Pro Pro Arg Pro Arg Pro Arg Pro Arg Pro Asp Pro Asp
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Peptide

<400> SEQUENCE: 310

Pro Pro Pro Pro Pro Arg Pro Arg Pro Arg Pro Asp Pro Asp Pro Asp
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Peptide

<400> SEQUENCE: 311

Pro Pro Pro Pro Pro His Pro Asp Pro His Pro Asp Pro His Pro Asp
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: Peptide

<400> SEQUENCE: 312

Pro Pro Pro Pro Pro His Pro His Pro His Pro His Pro His Pro His
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Peptide

<400> SEQUENCE: 313

Pro Pro Pro Pro Pro His Pro Asp Pro Asp Pro His Pro Asp Pro Asp
1               5                   10                  15

<210> SEQ ID NO 314
<211> LENGTH: 16
<212> TYPE: PRT
<213> ORGANISM: Artificial Sequence
<220> FEATURE:
<223> OTHER INFORMATION: Peptide

<400> SEQUENCE: 314

Pro Pro Pro Pro Pro His Pro Glu Pro Glu Pro His Pro Glu Pro Glu
1               5                   10                  15

```
<210> SEQ ID NO 315
<211> LENGTH: 16
<212> TYPE: PRT
<213> ORGANISM: Artificial Sequence
<220> FEATURE:
<223> OTHER INFORMATION: Peptide

<400> SEQUENCE: 315

Ser Ser Ser Ser Ser Arg Ser Asp Ser Arg Ser Asp Ser Arg Ser Asp
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Peptide

<400> SEQUENCE: 316

Ser Ser Ser Ser Ser Arg Ser Arg Ser Asp Ser Asp Ser Arg Ser Arg
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Peptide

<400> SEQUENCE: 317

Ser Ser Ser Ser Ser Glu Ser Lys Ser Glu Ser Lys Ser Glu Ser Lys
1               5                   10                  15

<210> SEQ ID NO 318
<211> LENGTH: 16
<212> TYPE: PRT
<213> ORGANISM: Artificial Sequence
<220> FEATURE:
<223> OTHER INFORMATION: Peptide

<400> SEQUENCE: 318

Ser Ser Ser Ser Ser Glu Ser Glu Ser Lys Ser Lys Ser Glu Ser Glu
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Peptide

<400> SEQUENCE: 319

Ser Ser Ser Ser Ser Arg Ser Glu Ser Arg Ser Glu Ser Arg Ser Glu
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Peptide

<400> SEQUENCE: 320

Ser Ser Ser Ser Ser Arg Ser Arg Ser Glu Ser Glu Ser Arg Ser Glu
1               5                   10                  15
```

```
<210> SEQ ID NO 321
<211> LENGTH: 16
<212> TYPE: PRT
<213> ORGANISM: Artificial Sequence
<220> FEATURE:
<223> OTHER INFORMATION: Peptide

<400> SEQUENCE: 321

Ser Ser Ser Ser Ser Lys Ser Asp Ser Lys Ser Asp Ser Lys Ser Asp
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Peptide

<400> SEQUENCE: 322

Ser Ser Ser Ser Ser Glu Ser His Ser Glu Ser His Ser Glu Ser His
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Peptide

<400> SEQUENCE: 323

Ser Ser Ser Ser Ser Glu Ser Glu Ser His Ser His Ser Glu Ser Glu
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Peptide

<400> SEQUENCE: 324

Ser Ser Ser Ser Ser Arg Ser Arg Ser Arg Ser Arg Ser Arg Ser Arg
1               5                   10                  15

<210> SEQ ID NO 325
<211> LENGTH: 16
<212> TYPE: PRT
<213> ORGANISM: Artificial Sequence
<220> FEATURE:
<223> OTHER INFORMATION: Peptide

<400> SEQUENCE: 325

Ser Ser Ser Ser Ser Arg Ser Arg Ser Arg Ser Arg Ser Asp Ser Asp
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Peptide

<400> SEQUENCE: 326

Ser Ser Ser Ser Ser Arg Ser Arg Ser Arg Ser Asp Ser Asp Ser Asp
1               5                   10                  15

<210> SEQ ID NO 327
```

```
<211> LENGTH: 16
<212> TYPE: PRT
<213> ORGANISM: Artificial Sequence
<220> FEATURE:
<223> OTHER INFORMATION: Peptide

<400> SEQUENCE: 327

Ser Ser Ser Ser Ser His Ser Asp Ser His Ser Asp Ser His Ser Asp
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Peptide

<400> SEQUENCE: 328

Ser Ser Ser Ser Ser His Ser His Ser His Ser His Ser His Ser His
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Peptide

<400> SEQUENCE: 329

Ser Ser Ser Ser Ser His Ser Asp Ser Asp Ser His Ser Asp Ser Asp
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Peptide

<400> SEQUENCE: 330

Ser Ser Ser Ser Ser His Ser Glu Ser Glu Ser His Ser Glu Ser Glu
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Peptide

<400> SEQUENCE: 331

Thr Thr Thr Thr Thr Arg Thr Asp Thr Arg Thr Asp Thr Arg Thr Asp
1               5                   10                  15

<210> SEQ ID NO 332
<211> LENGTH: 16
<212> TYPE: PRT
<213> ORGANISM: Artificial Sequence
<220> FEATURE:
<223> OTHER INFORMATION: Peptide

<400> SEQUENCE: 332

Thr Thr Thr Thr Thr Arg Thr Arg Thr Asp Thr Asp Thr Arg Thr Arg
1               5                   10                  15

<210> SEQ ID NO 333
<211> LENGTH: 16
```

```
<212> TYPE: PRT
<213> ORGANISM: Artificial Sequence
<220> FEATURE:
<223> OTHER INFORMATION: Peptide

<400> SEQUENCE: 333

Thr Thr Thr Thr Thr Glu Thr Lys Thr Glu Thr Lys Thr Glu Thr Lys
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Peptide

<400> SEQUENCE: 334

Thr Thr Thr Thr Thr Glu Thr Glu Thr Lys Thr Lys Thr Glu Thr Glu
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Peptide

<400> SEQUENCE: 335

Thr Thr Thr Thr Thr Arg Thr Glu Thr Arg Thr Glu Thr Arg Thr Glu
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Peptide

<400> SEQUENCE: 336

Thr Thr Thr Thr Thr Arg Thr Arg Thr Glu Thr Glu Thr Arg Thr Glu
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Peptide

<400> SEQUENCE: 337

Thr Thr Thr Thr Thr Lys Thr Asp Thr Lys Thr Asp Thr Lys Thr Asp
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Peptide

<400> SEQUENCE: 338

Thr Thr Thr Thr Thr Glu Thr His Thr Glu Thr His Thr Glu Thr His
1               5                   10                  15

<210> SEQ ID NO 339
<211> LENGTH: 16
<212> TYPE: PRT
```

<213> ORGANISM: Artificial Sequence
<220> FEATURE:
<223> OTHER INFORMATION: Peptide

<400> SEQUENCE: 339

Thr Thr Thr Thr Thr Glu Thr Glu Thr His Thr His Thr Glu Thr Glu
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Peptide

<400> SEQUENCE: 340

Thr Thr Thr Thr Thr Arg Thr Arg Thr Arg Thr Arg Thr Arg Thr Arg
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Peptide

<400> SEQUENCE: 341

Thr Thr Thr Thr Thr Arg Thr Arg Thr Arg Thr Arg Thr Asp Thr Asp
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Peptide

<400> SEQUENCE: 342

Thr Thr Thr Thr Thr Arg Thr Arg Thr Arg Thr Asp Thr Asp Thr Asp
1               5                   10                  15

<210> SEQ ID NO 343
<211> LENGTH: 16
<212> TYPE: PRT
<213> ORGANISM: Artificial Sequence
<220> FEATURE:
<223> OTHER INFORMATION: Peptide

<400> SEQUENCE: 343

Thr Thr Thr Thr Thr His Thr Asp Thr His Thr Asp Thr His Thr Asp
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Peptide

<400> SEQUENCE: 344

Thr Thr Thr Thr Thr His Thr His Thr His Thr His Thr His Thr His
1               5                   10                  15

<210> SEQ ID NO 345
<211> LENGTH: 16
<212> TYPE: PRT
<213> ORGANISM: Artificial Sequence

```
<220> FEATURE:
<223> OTHER INFORMATION: Peptide

<400> SEQUENCE: 345

Thr Thr Thr Thr Thr His Thr Asp Thr Asp Thr His Thr Asp Thr Asp
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Peptide

<400> SEQUENCE: 346

Thr Thr Thr Thr Thr His Thr Glu Thr Glu Thr His Thr Glu Thr Glu
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Peptide

<400> SEQUENCE: 347

Cys Cys Cys Cys Cys Arg Cys Asp Cys Arg Cys Asp Cys Arg Cys Asp
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Peptide

<400> SEQUENCE: 348

Cys Cys Cys Cys Cys Arg Cys Arg Cys Asp Cys Asp Cys Arg Cys Arg
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: Peptide

<400> SEQUENCE: 349

Cys Cys Cys Cys Cys Glu Cys Lys Cys Glu Cys Lys Cys Glu Cys Lys
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Peptide

<400> SEQUENCE: 350

Cys Cys Cys Cys Cys Glu Cys Glu Cys Lys Cys Lys Cys Glu Cys Glu
1               5                   10                  15

<210> SEQ ID NO 351
<211> LENGTH: 16
<212> TYPE: PRT
<213> ORGANISM: Artificial Sequence
<220> FEATURE:
```

<223> OTHER INFORMATION: Peptide

<400> SEQUENCE: 351

Cys Cys Cys Cys Cys Arg Cys Glu Cys Arg Cys Glu Cys Arg Cys Glu
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Peptide

<400> SEQUENCE: 352

Cys Cys Cys Cys Cys Arg Cys Arg Cys Glu Cys Glu Cys Arg Cys Glu
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Peptide

<400> SEQUENCE: 353

Cys Cys Cys Cys Cys Lys Cys Asp Cys Lys Cys Asp Cys Lys Cys Asp
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Peptide

<400> SEQUENCE: 354

Cys Cys Cys Cys Cys Glu Cys His Cys Glu Cys His Cys Glu Cys His
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Peptide

<400> SEQUENCE: 355

Cys Cys Cys Cys Cys Glu Cys Glu Cys His Cys His Cys Glu Cys Glu
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Peptide

<400> SEQUENCE: 356

Cys Cys Cys Cys Cys Arg Cys Arg Cys Arg Cys Arg Cys Arg Cys Arg
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Peptide

```
<400> SEQUENCE: 357

Cys Cys Cys Cys Arg Cys Arg Cys Arg Cys Asp Cys Asp
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Peptide

<400> SEQUENCE: 358

Cys Cys Cys Cys Cys Arg Cys Arg Cys Arg Cys Asp Cys Asp Cys Asp
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Peptide

<400> SEQUENCE: 359

Cys Cys Cys Cys Cys His Cys Asp Cys His Cys Asp Cys His Cys Asp
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Peptide

<400> SEQUENCE: 360

Cys Cys Cys Cys Cys His Cys His Cys His Cys His Cys His Cys His
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Peptide

<400> SEQUENCE: 361

Cys Cys Cys Cys Cys His Cys Asp Cys Asp Cys His Cys Asp Cys Asp
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Peptide

<400> SEQUENCE: 362

Cys Cys Cys Cys Cys His Cys Glu Cys Glu Cys His Cys Glu Cys Glu
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Peptide
```

<400> SEQUENCE: 363

Tyr Tyr Tyr Tyr Tyr Arg Tyr Asp Tyr Arg Tyr Asp Tyr Arg Tyr Asp
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Peptide

<400> SEQUENCE: 364

Tyr Tyr Tyr Tyr Tyr Arg Tyr Arg Tyr Asp Tyr Asp Tyr Arg Tyr Arg
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Peptide

<400> SEQUENCE: 365

Tyr Tyr Tyr Tyr Tyr Glu Tyr Lys Tyr Glu Tyr Lys Tyr Glu Tyr Lys
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Peptide

<400> SEQUENCE: 366

Tyr Tyr Tyr Tyr Tyr Glu Tyr Glu Tyr Lys Tyr Lys Tyr Glu Tyr Glu
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Peptide

<400> SEQUENCE: 367

Tyr Tyr Tyr Tyr Tyr Arg Tyr Glu Tyr Arg Tyr Glu Tyr Arg Tyr Glu
1               5                   10                  15

<210> SEQ ID NO 368
<211> LENGTH: 16
<212> TYPE: PRT
<213> ORGANISM: Artificial Sequence
<220> FEATURE:
<223> OTHER INFORMATION: Peptide

<400> SEQUENCE: 368

Tyr Tyr Tyr Tyr Tyr Arg Tyr Arg Tyr Glu Tyr Glu Tyr Arg Tyr Glu
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Peptide

<400> SEQUENCE: 369

Tyr Tyr Tyr Tyr Tyr Glu Tyr His Tyr Glu Tyr His Tyr Glu Tyr His
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: Peptide

<400> SEQUENCE: 370

Tyr Tyr Tyr Tyr Tyr Glu Tyr Glu Tyr His Tyr His Tyr Glu Tyr Glu
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Peptide

<400> SEQUENCE: 371

Tyr Tyr Tyr Tyr Tyr Arg Tyr Arg Tyr Arg Tyr Arg Tyr Arg Tyr Arg
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Peptide

<400> SEQUENCE: 372

Tyr Tyr Tyr Tyr Tyr Arg Tyr Arg Tyr Arg Tyr Arg Tyr Asp Tyr Asp
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Peptide

<400> SEQUENCE: 373

Tyr Tyr Tyr Tyr Tyr Arg Tyr Arg Tyr Arg Tyr Asp Tyr Asp Tyr Asp
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Peptide

<400> SEQUENCE: 374

Tyr Tyr Tyr Tyr Tyr His Tyr Asp Tyr His Tyr Asp Tyr His Tyr Asp
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Peptide

<400> SEQUENCE: 375

Tyr Tyr Tyr Tyr Tyr His Tyr His Tyr His Tyr His Tyr His Tyr His
1               5                   10                  15

<210> SEQ ID NO 376
<211> LENGTH: 16
<212> TYPE: PRT
<213> ORGANISM: Artificial Sequence
<220> FEATURE:
<223> OTHER INFORMATION: Peptide

<400> SEQUENCE: 376

Tyr Tyr Tyr Tyr Tyr His Tyr Asp Tyr Asp Tyr His Tyr Asp Tyr Asp
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Peptide

<400> SEQUENCE: 377

Tyr Tyr Tyr Tyr Tyr His Tyr Glu Tyr Glu Tyr His Tyr Glu Tyr Glu
1               5                   10                  15

<210> SEQ ID NO 378
<211> LENGTH: 16
<212> TYPE: PRT
<213> ORGANISM: Artificial Sequence
<220> FEATURE:
<223> OTHER INFORMATION: Peptide

<400> SEQUENCE: 378

Asn Asn Asn Asn Asn Arg Asn Asp Asn Arg Asn Asp Asn Arg Asn Asp
1               5                   10                  15

<210> SEQ ID NO 379
<211> LENGTH: 16
<212> TYPE: PRT
<213> ORGANISM: Artificial Sequence
<220> FEATURE:
<223> OTHER INFORMATION: Peptide

<400> SEQUENCE: 379

Asn Asn Asn Asn Asn Arg Asn Arg Asn Asp Asn Asp Asn Arg Asn Arg
1               5                   10                  15

<210> SEQ ID NO 380
<211> LENGTH: 16
<212> TYPE: PRT
<213> ORGANISM: Artificial Sequence
<220> FEATURE:
<223> OTHER INFORMATION: Peptide

<400> SEQUENCE: 380

Asn Asn Asn Asn Asn Glu Asn Lys Asn Glu Asn Lys Asn Glu Asn Lys
1               5                   10                  15

<210> SEQ ID NO 381
<211> LENGTH: 16
<212> TYPE: PRT
<213> ORGANISM: Artificial Sequence
<220> FEATURE:
<223> OTHER INFORMATION: Peptide

<400> SEQUENCE: 381

Asn Asn Asn Asn Asn Glu Asn Glu Asn Lys Asn Lys Asn Glu Asn Glu

<210> SEQ ID NO 382
<211> LENGTH: 16
<212> TYPE: PRT
<213> ORGANISM: Artificial Sequence
<220> FEATURE:
<223> OTHER INFORMATION: Peptide

<400> SEQUENCE: 382

Asn Asn Asn Asn Asn Arg Asn Glu Asn Arg Asn Glu Asn Arg Asn Glu
1               5                   10                  15

<210> SEQ ID NO 383
<211> LENGTH: 16
<212> TYPE: PRT
<213> ORGANISM: Artificial Sequence
<220> FEATURE:
<223> OTHER INFORMATION: Peptide

<400> SEQUENCE: 383

Asn Asn Asn Asn Asn Arg Asn Arg Asn Glu Asn Glu Asn Arg Asn Glu
1               5                   10                  15

<210> SEQ ID NO 384
<211> LENGTH: 16
<212> TYPE: PRT
<213> ORGANISM: Artificial Sequence
<220> FEATURE:
<223> OTHER INFORMATION: Peptide

<400> SEQUENCE: 384

Asn Asn Asn Asn Asn Lys Asn Asp Asn Lys Asn Asp Asn Lys Asn Asp
1               5                   10                  15

<210> SEQ ID NO 385
<211> LENGTH: 16
<212> TYPE: PRT
<213> ORGANISM: Artificial Sequence
<220> FEATURE:
<223> OTHER INFORMATION: Peptide

<400> SEQUENCE: 385

Asn Asn Asn Asn Asn Glu Asn His Asn Glu Asn His Asn Glu Asn His
1               5                   10                  15

<210> SEQ ID NO 386
<211> LENGTH: 16
<212> TYPE: PRT
<213> ORGANISM: Artificial Sequence
<220> FEATURE:
<223> OTHER INFORMATION: Peptide

<400> SEQUENCE: 386

Asn Asn Asn Asn Asn Glu Asn Glu Asn His Asn His Asn Glu Asn Glu
1               5                   10                  15

<210> SEQ ID NO 387
<211> LENGTH: 16
<212> TYPE: PRT
<213> ORGANISM: Artificial Sequence
<220> FEATURE:
<223> OTHER INFORMATION: Peptide

<400> SEQUENCE: 387

Asn Asn Asn Asn Asn Arg Asn Arg Asn Arg Asn Arg Asn Arg Asn Arg
1               5                   10                  15

<210> SEQ ID NO 388
<211> LENGTH: 16
<212> TYPE: PRT
<213> ORGANISM: Artificial Sequence
<220> FEATURE:
<223> OTHER INFORMATION: Peptide

<400> SEQUENCE: 388

Asn Asn Asn Asn Asn Arg Asn Arg Asn Arg Asn Arg Asn Asp Asn Asp
1               5                   10                  15

<210> SEQ ID NO 389
<211> LENGTH: 16
<212> TYPE: PRT
<213> ORGANISM: Artificial Sequence
<220> FEATURE:
<223> OTHER INFORMATION: Peptide

<400> SEQUENCE: 389

Asn Asn Asn Asn Asn Arg Asn Arg Asn Arg Asn Asp Asn Asp Asn Asp
1               5                   10                  15

<210> SEQ ID NO 390
<211> LENGTH: 16
<212> TYPE: PRT
<213> ORGANISM: Artificial Sequence
<220> FEATURE:
<223> OTHER INFORMATION: Peptide

<400> SEQUENCE: 390

Asn Asn Asn Asn Asn His Asn Asp Asn His Asn Asp Asn His Asn Asp
1               5                   10                  15

<210> SEQ ID NO 391
<211> LENGTH: 16
<212> TYPE: PRT
<213> ORGANISM: Artificial Sequence
<220> FEATURE:
<223> OTHER INFORMATION: Peptide

<400> SEQUENCE: 391

Asn Asn Asn Asn Asn His Asn His Asn His Asn His Asn His Asn His
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Peptide

<400> SEQUENCE: 392

Asn Asn Asn Asn Asn His Asn Asp Asn Asp Asn His Asn Asp Asn Asp
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: Peptide

<400> SEQUENCE: 393

Asn Asn Asn Asn Asn His Asn Glu Asn Glu Asn His Asn Glu Asn Glu
1               5                   10                  15

```
<210> SEQ ID NO 394
<211> LENGTH: 16
<212> TYPE: PRT
<213> ORGANISM: Artificial Sequence
<220> FEATURE:
<223> OTHER INFORMATION: Peptide

<400> SEQUENCE: 394

Gln Gln Gln Gln Gln Arg Gln Asp Gln Arg Gln Asp Gln Arg Gln Asp
1               5                   10                  15

<210> SEQ ID NO 395
<211> LENGTH: 16
<212> TYPE: PRT
<213> ORGANISM: Artificial Sequence
<220> FEATURE:
<223> OTHER INFORMATION: Peptide

<400> SEQUENCE: 395

Gln Gln Gln Gln Gln Arg Gln Arg Gln Asp Gln Asp Gln Arg Gln Arg
1               5                   10                  15

<210> SEQ ID NO 396
<211> LENGTH: 16
<212> TYPE: PRT
<213> ORGANISM: Artificial Sequence
<220> FEATURE:
<223> OTHER INFORMATION: Peptide

<400> SEQUENCE: 396

Gln Gln Gln Gln Gln Glu Gln Lys Gln Glu Gln Lys Gln Glu Gln Lys
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: Peptide

<400> SEQUENCE: 397

Gln Gln Gln Gln Gln Glu Gln Glu Gln Lys Gln Lys Gln Glu Gln Glu
1               5                   10                  15

<210> SEQ ID NO 398
<211> LENGTH: 16
<212> TYPE: PRT
<213> ORGANISM: Artificial Sequence
<220> FEATURE:
<223> OTHER INFORMATION: Peptide

<400> SEQUENCE: 398

Gln Gln Gln Gln Gln Arg Gln Glu Gln Arg Gln Glu Gln Arg Gln Glu
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Peptide

<400> SEQUENCE: 399

Gln Gln Gln Gln Gln Arg Gln Arg Gln Glu Gln Glu Gln Arg Gln Glu
1               5                   10                  15
```

```
<210> SEQ ID NO 400
<211> LENGTH: 16
<212> TYPE: PRT
<213> ORGANISM: Artificial Sequence
<220> FEATURE:
<223> OTHER INFORMATION: Peptide

<400> SEQUENCE: 400

Gln Gln Gln Gln Gln Lys Gln Asp Gln Lys Gln Asp Gln Lys Gln Asp
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: Peptide

<400> SEQUENCE: 401

Gln Gln Gln Gln Gln Glu Gln His Gln Glu Gln His Gln Glu Gln His
1               5                   10                  15

<210> SEQ ID NO 402
<211> LENGTH: 16
<212> TYPE: PRT
<213> ORGANISM: Artificial Sequence
<220> FEATURE:
<223> OTHER INFORMATION: Peptide

<400> SEQUENCE: 402

Gln Gln Gln Gln Gln Glu Gln Glu Gln His Gln His Gln Glu Gln Glu
1               5                   10                  15

<210> SEQ ID NO 403
<211> LENGTH: 16
<212> TYPE: PRT
<213> ORGANISM: Artificial Sequence
<220> FEATURE:
<223> OTHER INFORMATION: Peptide

<400> SEQUENCE: 403

Gln Gln Gln Gln Gln Arg Gln Arg Gln Arg Gln Arg Gln Arg Gln Arg
1               5                   10                  15

<210> SEQ ID NO 404
<211> LENGTH: 16
<212> TYPE: PRT
<213> ORGANISM: Artificial Sequence
<220> FEATURE:
<223> OTHER INFORMATION: Peptide

<400> SEQUENCE: 404

Gln Gln Gln Gln Gln Arg Gln Arg Gln Arg Gln Arg Gln Asp Gln Asp
1               5                   10                  15

<210> SEQ ID NO 405
<211> LENGTH: 16
<212> TYPE: PRT
<213> ORGANISM: Artificial Sequence
<220> FEATURE:
<223> OTHER INFORMATION: Peptide

<400> SEQUENCE: 405

Gln Gln Gln Gln Gln Arg Gln Arg Gln Arg Gln Asp Gln Asp Gln Asp
1               5                   10                  15

<210> SEQ ID NO 406
```

```
<211> LENGTH: 16
<212> TYPE: PRT
<213> ORGANISM: Artificial Sequence
<220> FEATURE:
<223> OTHER INFORMATION: Peptide

<400> SEQUENCE: 406

Gln Gln Gln Gln Gln His Gln Asp Gln His Gln Asp Gln His Gln Asp
1               5                   10                  15

<210> SEQ ID NO 407
<211> LENGTH: 16
<212> TYPE: PRT
<213> ORGANISM: Artificial Sequence
<220> FEATURE:
<223> OTHER INFORMATION: Peptide

<400> SEQUENCE: 407

Gln Gln Gln Gln Gln His Gln His Gln His Gln His Gln His Gln His
1               5                   10                  15

<210> SEQ ID NO 408
<211> LENGTH: 16
<212> TYPE: PRT
<213> ORGANISM: Artificial Sequence
<220> FEATURE:
<223> OTHER INFORMATION: Peptide

<400> SEQUENCE: 408

Gln Gln Gln Gln Gln His Gln Asp Gln Asp Gln His Gln Asp Gln Asp
1               5                   10                  15

<210> SEQ ID NO 409
<211> LENGTH: 16
<212> TYPE: PRT
<213> ORGANISM: Artificial Sequence
<220> FEATURE:
<223> OTHER INFORMATION: Peptide

<400> SEQUENCE: 409

Gln Gln Gln Gln Gln His Gln Glu Gln Glu Gln His Gln Glu Gln Glu
1               5                   10                  15

<210> SEQ ID NO 410
<211> LENGTH: 16
<212> TYPE: PRT
<213> ORGANISM: Artificial Sequence
<220> FEATURE:
<223> OTHER INFORMATION: Peptide

<400> SEQUENCE: 410

Glu Ala Lys Ala Glu Ala Lys Ala Glu Ala Lys Ala Glu Ala Lys Ala
1               5                   10                  15
```